US011911122B2

United States Patent
Beckman et al.

(10) Patent No.: US 11,911,122 B2
(45) Date of Patent: Feb. 27, 2024

(54) INSTRUMENT INSERTION CARRIAGE FOR ROBOTIC SURGICAL TOOLS

(71) Applicant: Cilag GmbH International, Zug (CH)

(72) Inventors: Andrew T. Beckman, Cincinnati, OH (US); Charles J. Scheib, Loveland, OH (US); Benjamin D. Dickerson, Cincinnati, OH (US); Jason A. Hill, Loveland, OH (US)

(73) Assignee: Cilag GmbH International, Zug (CH)

( * ) Notice: Subject to any disclaimer, the term of this patent is extended or adjusted under 35 U.S.C. 154(b) by 756 days.

(21) Appl. No.: 16/946,428

(22) Filed: Jun. 22, 2020

(65) Prior Publication Data

US 2021/0393342 A1 Dec. 23, 2021

(51) Int. Cl.
*A61B 34/30* (2016.01)
*A61G 13/10* (2006.01)
(Continued)

(52) U.S. Cl.
CPC ............ *A61B 34/30* (2016.02); *A61G 13/101* (2013.01); *B25J 9/102* (2013.01); *B25J 15/0019* (2013.01);
(Continued)

(58) Field of Classification Search
CPC .............. A61B 34/30; A61B 2034/301; A61B 2034/302; A61B 2034/303;
(Continued)

(56) References Cited

U.S. PATENT DOCUMENTS 6,264,665 B1 7/2001 Yu et al.
6,988,425 B2 * 1/2006 Nagai .................... F16H 7/023
74/89.32

(Continued)

FOREIGN PATENT DOCUMENTS

WO 2015167808 A1 11/2015
WO 2016043845 A1 3/2016
(Continued)

OTHER PUBLICATIONS

Written Opinion and International Search Report from corresponding PCT Application No. PCT/EP2021/066792 dated Feb. 7, 2022.

*Primary Examiner* — Randell J Krug
(74) *Attorney, Agent, or Firm* — Vorys, Sater, Seymour and Pease, LLP

(57) ABSTRACT

A robotic surgical tool for a robotic instrument driver that includes a handle having a first end, at least one spline rotatably coupled to the handle and extending proximally from the first end, a carriage movably mounted to the at least one spline and including a first layer and a second layer operatively coupled to the first layer. At least one spline extends through a portion of at least one of the first and second layers and the carriage translates along the at least one spline. The robotic surgical tool also includes an elongate shaft extending from the carriage and penetrating the first end, the shaft having an end effector arranged at a distal end thereof and an activating mechanism coupled to one or both of the first and second layers and actuatable to operate a function of the end effector.

21 Claims, 26 Drawing Sheets

(51) Int. Cl.
*B25J 9/10* (2006.01)
*B25J 15/00* (2006.01)
*B25J 15/04* (2006.01)
*F16H 25/20* (2006.01)
*F16H 57/00* (2012.01)

(52) U.S. Cl.
CPC ....... *B25J 15/0028* (2013.01); *B25J 15/0052* (2013.01); *B25J 15/0061* (2013.01); *B25J 15/045* (2013.01); *F16H 25/20* (2013.01); *F16H 57/0025* (2013.01); *A61B 2034/301* (2016.02); *A61B 2034/302* (2016.02); *A61B 2034/303* (2016.02); *A61B 2034/305* (2016.02); *F16H 2025/2081* (2013.01)

(58) Field of Classification Search
CPC .. A61B 2034/305; A61G 13/101; B25J 9/102; B25J 15/0019; B25J 15/0028; B25J 15/0052; B25J 15/0061; B25J 15/045; F16H 25/20; F16H 57/0025; F16H 2025/2081

See application file for complete search history.

(56) References Cited

U.S. PATENT DOCUMENTS

| | | | |
|---|---|---|---|
| 10,321,964 B2* | 6/2019 | Grover | A61B 34/35 |
| 2018/0228557 A1 | 8/2018 | Darisse et al. | |
| 2019/0298464 A1* | 10/2019 | Abbott | A61B 34/70 |
| 2021/0015572 A1 | 1/2021 | Gomez et al. | |
| 2021/0022815 A1 | 1/2021 | Abbott | |

FOREIGN PATENT DOCUMENTS

| | | |
|---|---|---|
| WO | 2018053305 A1 | 3/2018 |
| WO | 2019191420 A1 | 10/2019 |

* cited by examiner

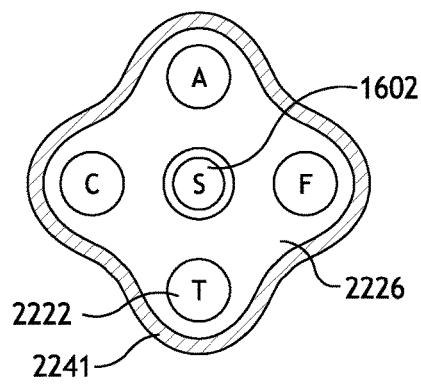
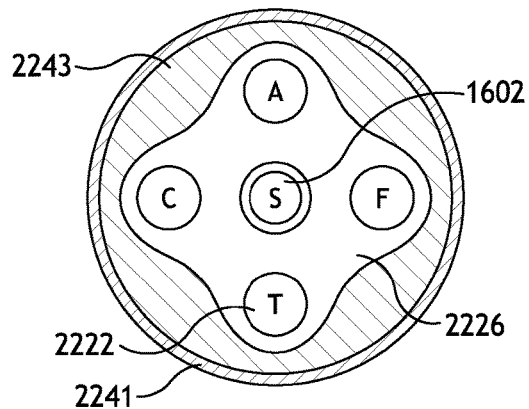
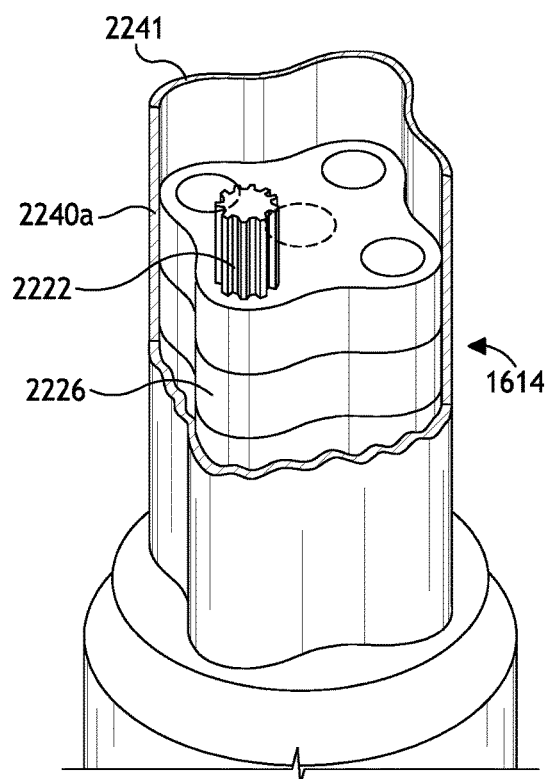
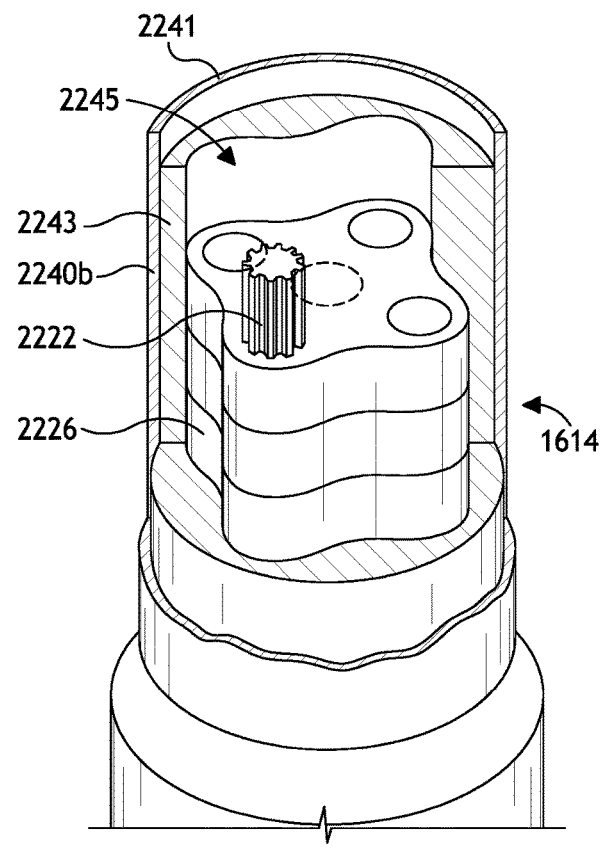
FIG. 22A
FIG. 22B

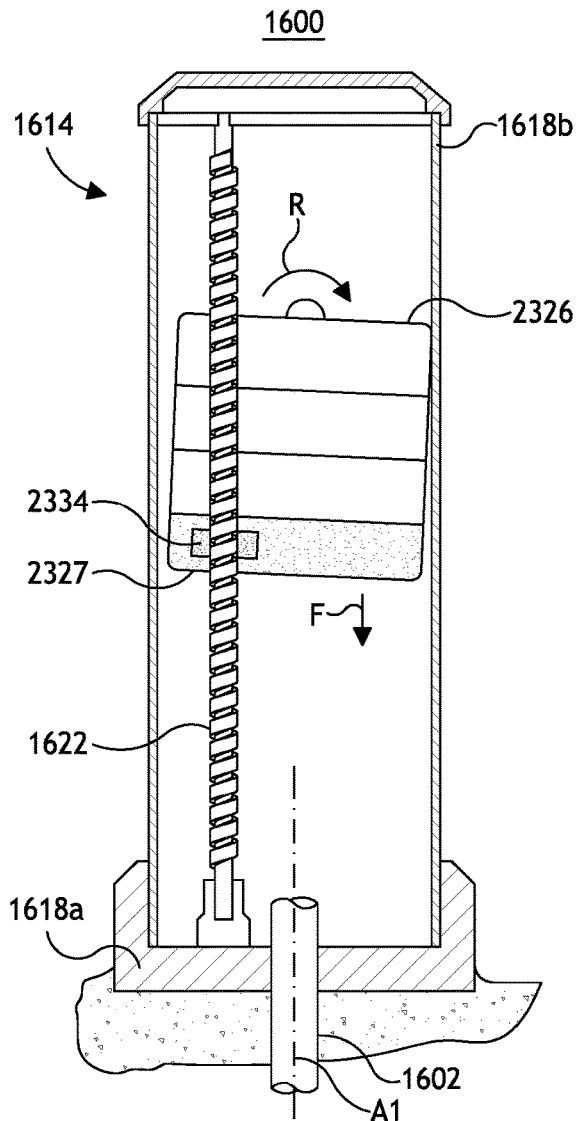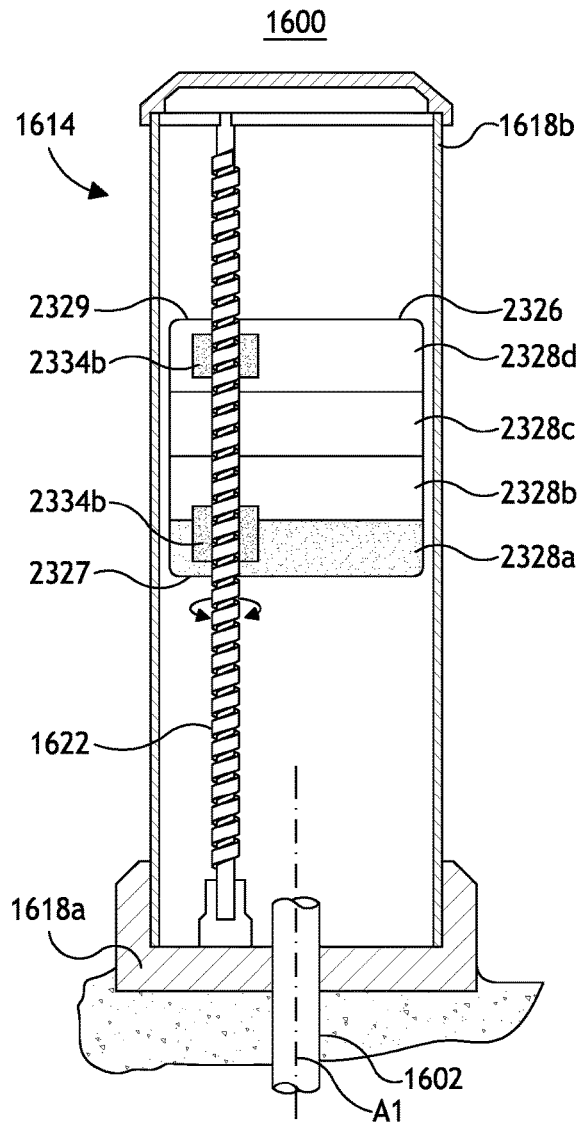

INSTRUMENT INSERTION CARRIAGE FOR ROBOTIC SURGICAL TOOLS

TECHNICAL FIELD

The systems and methods disclosed herein are directed to robotic surgical systems and, more particularly to, robotic surgical tools including a carriage movably mounted to the tool having a layered architecture configured to support at least one activating mechanism to operate various functions of the robotic tool

BACKGROUND

Minimally invasive surgical (MIS) instruments are often preferred over traditional open surgical devices due to the reduced post-operative recovery time and minimal scarring. The most common MIS procedure may be endoscopy, and the most common form of endoscopy is laparoscopy, in which one or more small incisions are formed in the abdomen of a patient and a trocar is inserted through the incision to form a pathway that provides access to the abdominal cavity. The cannula and sealing system of the trocar is used to introduce various instruments and tools into the abdominal cavity, as well as to provide insufflation to elevate the abdominal wall above the organs. The instruments can be used to engage and/or treat tissue in a number of ways to achieve a diagnostic or therapeutic effect.

Each surgical tool typically includes an end effector arranged at its distal end. Example end effectors include clamps, graspers, scissors, staplers, suction irrigators, blades (i.e., RF) and needle holders, and are similar to those used in conventional (open) surgery except that the end effector of each tool is separated from its handle by an approximately 12-inch long shaft. A camera or image capture device, such as an endoscope, is also commonly introduced into the abdominal cavity to enable the surgeon to view the surgical field and the operation of the end effectors during operation. The surgeon is able to view the procedure in real-time by means of a visual display in communication with the image capture device.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint that creates a more natural hand-like articulation and allows for access to hard to reach spaces. The instrument's end effector can be articulated (moved) using motors and actuators forming part of a computerized motion system. A user (e.g., a surgeon) is able to remotely operate an instrument's end effector by grasping and manipulating in space one or more controllers that communicate with an instrument driver coupled to the surgical instrument. User inputs are processed by a computer system incorporated into the robotic surgical system and the instrument driver responds by actuating the motors and actuators of the motion system. Moving the drive cables and/or other mechanical mechanisms to manipulate the end effector to desired positions and configurations.

Improvements to robotically-enabled medical systems will provide physicians with the ability to perform endoscopic and laparoscopic procedures more effectively and with improved ease.

SUMMARY OF DISCLOSURE

Various details of the present disclosure are hereinafter summarized to provide a basic understanding. This summary is not an extensive overview of the disclosure and is neither intended to identify certain elements of the disclosure, nor to delineate the scope thereof. Rather, the primary purpose of this summary is to present some concepts of the disclosure in a simplified form prior to the more detailed description that is presented hereinafter.

Embodiments disclosed herein include a robotic surgical tool for a robotic instrument driver that includes a handle having a first end, at least one spline rotatably coupled to the handle and extending proximally from the first end, a carriage movably mounted to the at least one spline and including a first layer and a second layer operatively coupled to the first layer. At least one spline extends through a portion of at least one of the first and second layers and the carriage translates along the at least one spline. The robotic surgical tool also includes an elongate shaft extending from the carriage and penetrating the first end, the shaft having an end effector arranged at a distal end thereof and an activating mechanism coupled to one or both of the first and second layers and actuatable to operate a function of the end effector. In a further embodiment, the robotic surgical tool further includes a drive input arranged at the first end and operatively coupled to the at least one spline such that rotation of the drive input correspondingly rotates the at least one spline and an instrument driver arranged at an end of a robotic arm and matable with the handle at the first end, the instrument driver providing a drive output matable with the drive input such that rotation of the drive output correspondingly rotates the drive input and thereby actuates the activating mechanism. In another further embodiment, the at least one spline forms part of a plurality of splines, and wherein each spline is rotationally attached to the first end of the handle and configured to mechanically communicate with a drive output of a robotic instrument driver, each spline being coupled to a separate activating mechanism, and wherein rotation of the spline drives an associated function of the end effector. In another further embodiment, the activating mechanism includes a drive gear coupled to or forming part of the at least one spline, and wherein rotation of the at least one spline correspondingly rotates the drive gear. In another further embodiment, the drive gear defines a passage complementary in shape to a cross-section of the at least one spline, and wherein the at least one spline extends through the passage. In another further embodiment, the activating mechanism includes a drive gear arranged adjacent to and in sliding contact with the at least one spline, and wherein rotation of the associated spline rotates the gear of the activating mechanism. In another further embodiment, the drive gear defines gear teeth that intermesh with gear teeth defined by the at least one spline. In another further embodiment, the carriage comprises three or more layers. In another further embodiment, the robotic surgical tool further includes a guide rail extending proximally from the first end and one or more notches defined in the carriage and sized to receive the guide rail. The guide rail slides within the one or more notches as the carriage moves along the at least one spline. In another further embodiment, the guide rail assumes torsional loading of the carriage and thereby minimizes rotation of the carriage with respect to the handle. In another further embodiment, the one or more notches are defined on an outer periphery of one or both of the first and second layers. In another further embodiment, the one or more notches comprises a first notch and a second notch, and wherein the first notch and the second notch are located on circumferentially opposite sides of the carriage. In another further embodiment, the robotic surgical tool further includes a lead screw extending from the first end, wherein the carriage is movably mounted to the lead screw at a carriage nut secured to the carriage, and wherein rotation of the lead screw moves the carriage and the carriage nut axially toward and away from the first end and thereby moves the end effector distally or proximally. In another further embodiment, the first and second layers are removably secured to each other using one or more mechanical fasteners. In another further embodiment, the first and second layers each include coaxially aligned holes that receive the one or more mechanical fasteners. In another further embodiment, the function of the end effector is selected from the group consisting of articulation of the end effector, clamping of jaws of the end effector, displacing a cutting element of the end effector, displacing the end effector, and any combination thereof. In another further embodiment, the robotic surgical tool further includes a second end opposite the first end of the handle, wherein the at least one spline extends between the first and second ends and wherein the carriage is configured to translate between the first and second ends.

Embodiments disclosed herein may further include a method that includes locating a robotic surgical tool adjacent a patient, the robotic surgical tool comprising a handle having a first end, at least one spline rotatably coupled to the handle and extending proximally from the first end, a carriage movably mounted to the at least one spline and including a first layer and a second layer operatively coupled to the first layer, wherein the at least one spline extends through a portion of at least one of the first and second layers, an elongate shaft extending from the carriage and penetrating the first end, the shaft having an end effector arranged at a distal end thereof, and an activating mechanism coupled to one or both of the first and second layers. The method including rotating the at least one spline by actuating a drive input arranged at the first end and operatively coupled to the at least one spline and actuating the activating mechanism as the at least one spline rotates and thereby operating a function of the end effector. In further embodiments, the method further includes removably securing the first and second layers to each other using one or more mechanical fasteners. In another further embodiment, the method further includes advancing the carriage distally and proximally along the at least one spline. In another further embodiment, the method further includes guiding the carriage toward and away from the first end with at least a guide rail extending from the first end.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 22A illustrates an isometric side view of an example carriage and shroud that may incorporate some or all of the principles of the present disclosure.

FIG. 22B illustrates an isometric side view of another example carriage and shroud that may incorporate some or all of the principles of the present disclosure FIG. 23A illustrates a cross-sectional view of an example carriage mounted to a lead screw that may incorporate some or all of the principles of the present disclosure.

FIG. 23B illustrates a cross-sectional view of another example carriage mounted to a lead screw that may incorporate some or all of the principles of the present disclosure.

DETAILED DESCRIPTION

1. Overview.

Aspects of the present disclosure may be integrated into a robotically-enabled medical system capable of performing a variety of medical procedures, including both minimally invasive (e.g., laparoscopy) and non-invasive (e.g., endoscopy) procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
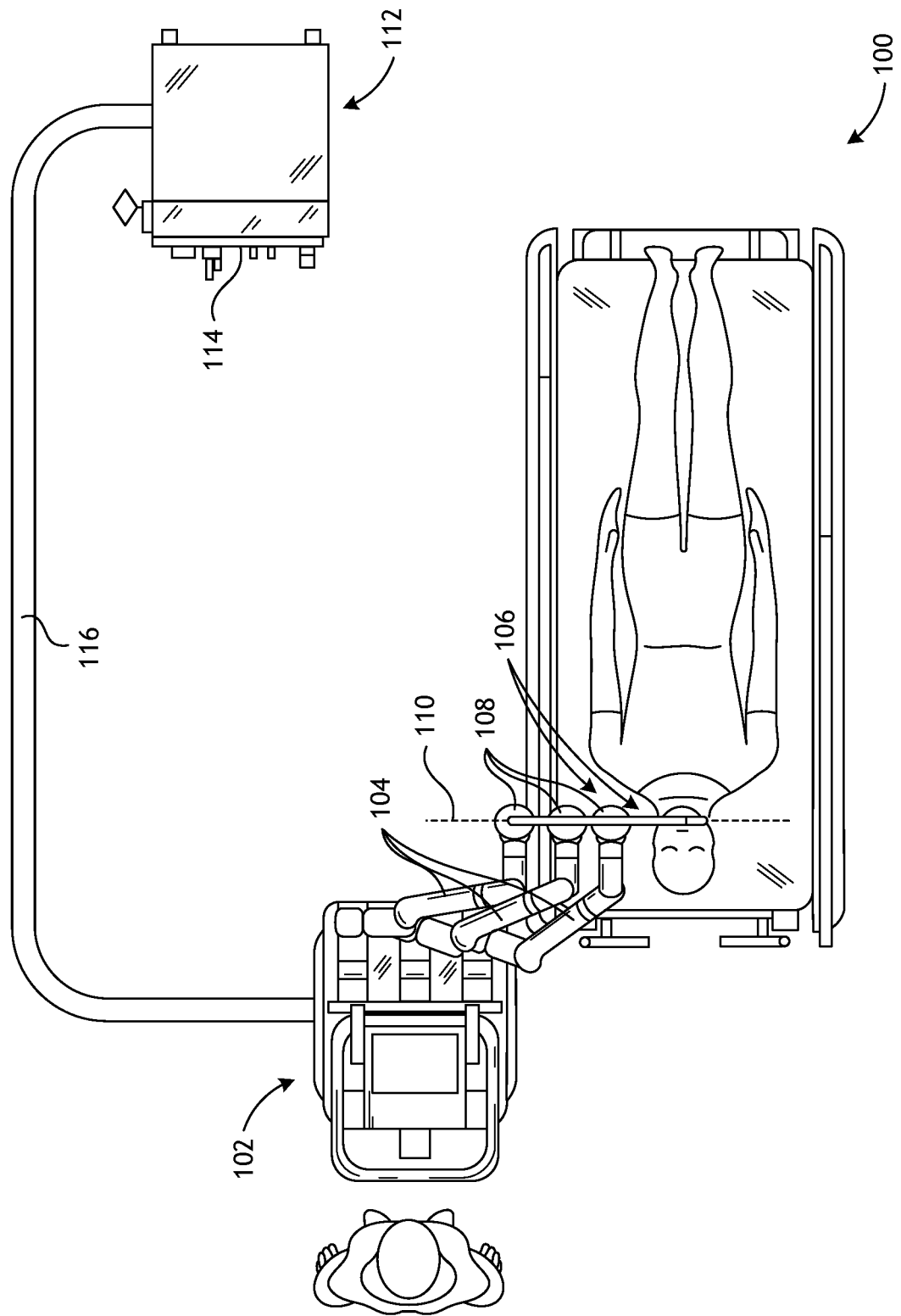
FIG. 1 illustrates an embodiment of a cart-based robotic system arranged for diagnostic and/or therapeutic bronchoscopy procedure(s).

The robotically-enabled medical system may be configured in a variety of ways depending on the particular procedure. FIG. 1 illustrates an embodiment of a cart-based robotically-enabled system 100 arranged for a diagnostic and/or therapeutic bronchoscopy procedure. For a bronchoscopy procedure, the robotic system 100 may include a cart 102 having one or more robotic arms 104 (three shown) to deliver a medical instrument (alternately referred to as a "surgical tool"), such as a steerable endoscope 106 (e.g., a procedure-specific bronchoscope for bronchoscopy), to a natural orifice access point (i.e., the mouth of the patient) to deliver diagnostic and/or therapeutic tools. As shown, the cart 102 may be positioned proximate to the patient's upper torso in order to provide access to the access point. Similarly, the robotic arms 104 may be actuated to position the bronchoscope relative to the access point. The arrangement in FIG. 1 may also be utilized when performing a gastrointestinal (GI) procedure with a gastroscope, a specialized endoscope for GI procedures.

Once the cart 102 is properly positioned adjacent the patient, the robotic arms 104 are operated to insert the steerable endoscope 106 into the patient robotically, manually, or a combination thereof. The steerable endoscope 106 may comprise at least two telescoping parts, such as an inner leader portion and an outer sheath portion, where each portion is coupled to a separate instrument driver of a set of instrument drivers 108. As illustrated, each instrument driver 108 is coupled to the distal end of a corresponding one of the robotic arms 104. This linear arrangement of the instrument drivers 108, which facilitates coaxially aligning the leader portion with the sheath portion, creates a "virtual rail" 110 that may be repositioned in space by manipulating the robotic arms 104 into different angles and/or positions. Translation of the instrument drivers 108 along the virtual rail 110 telescopes the inner leader portion relative to the outer sheath portion, thus effectively advancing or retracting the endoscope 106 relative to the patient.

As illustrated, the virtual rail 110 (and other virtual rails described herein) is depicted in the drawings using dashed lines, thus not constituting any physical structure of the system 100. The angle of the virtual rail 110 may be adjusted, translated, and pivoted based on clinical application or physician preference. For example, in bronchoscopy, the angle and position of the virtual rail 110 as shown represents a compromise between providing physician access to the endoscope 106 while minimizing friction that results from bending the endoscope 106 into the patient's mouth.

After insertion into the patient's mouth, the endoscope 106 may be directed down the patient's trachea and lungs using precise commands from the robotic system 100 until reaching a target destination or operative site. In order to enhance navigation through the patient's lung network and/or reach the desired target, the endoscope 106 may be manipulated to telescopically extend the inner leader portion from the outer sheath portion to obtain enhanced articulation and greater bend radius. The use of separate instrument drivers 108 also allows the leader portion and sheath portion to be driven independent of each other.

For example, the endoscope 106 may be directed to deliver a biopsy needle to a target, such as, for example, a lesion or nodule within the lungs of a patient. The needle may be deployed down a working channel that runs the length of the endoscope 106 to obtain a tissue sample to be analyzed by a pathologist. Depending on the pathology results, additional tools may be deployed down the working channel of the endoscope for additional biopsies. After identifying a tissue sample to be malignant, the endoscope 106 may endoscopically deliver tools to resect the potentially cancerous tissue. In some instances, diagnostic and therapeutic treatments can be delivered in separate procedures. In those circumstances, the endoscope 106 may also be used to deliver a fiducial marker to "mark" the location of a target nodule as well. In other instances, diagnostic and therapeutic treatments may be delivered during the same procedure.

The system 100 may also include a movable tower 112, which may be connected via support cables to the cart 102 to provide support for controls, electronics, fluidics, optics, sensors, and/or power to the cart 102. Placing such functionality in the tower 112 allows for a smaller form factor cart 102 that may be more easily adjusted and/or re-positioned by an operating physician and his/her staff. Additionally, the division of functionality between the cart/table and the support tower 112 reduces operating room clutter and facilitates improving clinical workflow. While the cart 102 may be positioned close to the patient, the tower 112 may alternatively be stowed in a remote location to stay out of the way during a procedure.

In support of the robotic systems described above, the tower 112 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 112 or the cart 102, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, motors in the joints of the robotic arms 104 may position the arms into a certain posture or angular orientation.

The tower 112 may also include one or more of a pump, flow meter, valve control, and/or fluid access in order to provide controlled irrigation and aspiration capabilities to the system 100 that may be deployed through the endoscope 106. These components may also be controlled using the computer system of the tower 112. In some embodiments, irrigation and aspiration capabilities may be delivered directly to the endoscope 106 through separate cable(s).

The tower 112 may include a voltage and surge protector designed to provide filtered and protected electrical power to the cart 102, thereby avoiding placement of a power transformer and other auxiliary power components in the cart 102, resulting in a smaller, more moveable cart 102.

The tower 112 may also include support equipment for sensors deployed throughout the robotic system 100. For example, the tower 112 may include opto-electronics equipment for detecting, receiving, and processing data received from optical sensors or cameras throughout the robotic system 100. In combination with the control system, such opto-electronics equipment may be used to generate real-time images for display in any number of consoles deployed throughout the system, including in the tower 112. Similarly, the tower 112 may also include an electronic subsystem for receiving and processing signals received from deployed electromagnetic (EM) sensors. The tower 112 may also be used to house and position an EM field generator for detection by EM sensors in or on the medical instrument.

The tower 112 may also include a console 114 in addition to other consoles available in the rest of the system, e.g., a console mounted to the cart 102. The console 114 may include a user interface and a display screen (e.g., a touchscreen) for the physician operator. Consoles in the system 100 are generally designed to provide both robotic controls as well as pre-operative and real-time information of the procedure, such as navigational and localization information of the endoscope 106. When the console 114 is not the only console available to the physician, it may be used by a second operator, such as a nurse, to monitor the health or vitals of the patient and the operation of system, as well as provide procedure-specific data, such as navigational and localization information. In other embodiments, the console 114 may be housed in a body separate from the tower 112.

The tower 112 may be coupled to the cart 102 and endoscope 106 through one or more cables 116 connections. In some embodiments, support functionality from the tower 112 may be provided through a single cable 116 extending to the cart 102, thus simplifying and de-cluttering the operating room. In other embodiments, specific functionality may be coupled in separate cabling and connections. For example, while power may be provided through a single power cable to the cart 102, support for controls, optics, fluidics, and/or navigation may be provided through one or more separate cables.

Figure 2:
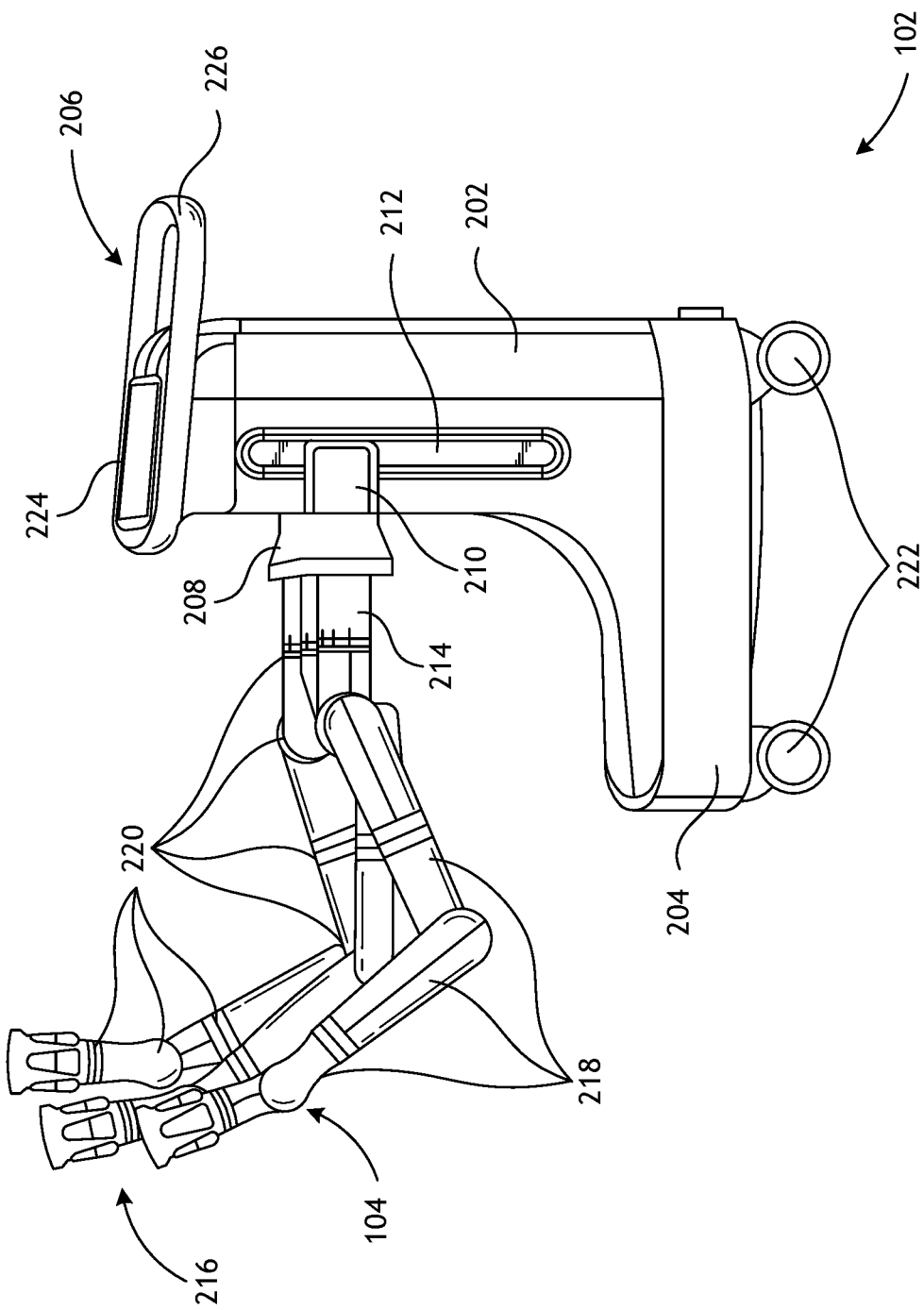
FIG. 2 depicts further aspects of the robotic system of FIG. 1.

FIG. 2 provides a detailed illustration of an embodiment of the cart 102 from the cart-based robotically-enabled system 100 of FIG. 1. The cart 102 generally includes an elongated support structure 202 (also referred to as a "column"), a cart base 204, and a console 206 at the top of the column 202. The column 202 may include one or more carriages, such as a carriage 208 (alternatively "arm support") for supporting the deployment of the robotic arms 104. The carriage 208 may include individually configurable arm mounts that rotate along a perpendicular axis to adjust the base 214 of the robotic arms 104 for better positioning relative to the patient. The carriage 208 also includes a carriage interface 210 that allows the carriage 208 to vertically translate along the column 202.

The carriage interface 210 is connected to the column 202 through slots, such as slot 212, that are positioned on opposite sides of the column 202 to guide the vertical translation of the carriage 208. The slot 212 contains a vertical translation interface to position and hold the carriage 208 at various vertical heights relative to the cart base 204. Vertical translation of the carriage 208 allows the cart 102 to adjust the reach of the robotic arms 104 to meet a variety of table heights, patient sizes, and physician preferences. Similarly, the individually configurable arm mounts on the carriage 208 allow a base 214 of the robotic arms 104 to be angled in a variety of configurations.

In some embodiments, the slot 212 may be supplemented with slot covers (not shown) that are flush and parallel to the slot surface to prevent dirt and fluid ingress into the internal chambers of the column 202 and the vertical translation interface as the carriage 208 vertically translates. The slot covers may be deployed through pairs of spring spools positioned near the vertical top and bottom of the slot 212. The covers are coiled within the spools until deployed to extend and retract from their coiled state as the carriage 208 vertically translates up and down. The spring-loading of the spools provides force to retract the cover into a spool when carriage 208 translates towards the spool, while also maintaining a tight seal when the carriage 208 translates away from the spool. The covers may be connected to the carriage 208 using, for example, brackets in the carriage interface 210 to ensure proper extension and retraction of the cover as the carriage 208 translates.

The column 202 may internally comprise mechanisms, such as gears and motors, that are designed to use a vertically aligned lead screw to translate the carriage 208 in a mechanized fashion in response to control signals generated in response to user inputs, e.g., inputs from the console 206.

The robotic arms 104 may generally comprise robotic arm bases 214 and end effectors 216 (three shown), separated by a series of linkages 218 connected by a corresponding series of joints 220, each joint 220 including an independent actuator, and each actuator including an independently controllable motor. Each independently controllable joint 220 represents an independent degree of freedom available to the corresponding robotic arm 104. In the illustrated embodiment, each arm 104 has seven joints 220, thus providing seven degrees of freedom. A multitude of joints 220 result in a multitude of degrees of freedom, allowing for "redundant" degrees of freedom. Redundant degrees of freedom allow the robotic arms 104 to position their respective end effectors 216 at a specific position, orientation, and trajectory in space using different linkage positions and joint angles. This allows for the system 100 to position and direct a medical instrument from a desired point in space while allowing the physician to move the arm joints 220 into a clinically advantageous position away from the patient to create greater access, while avoiding arm collisions.

The cart base 204 balances the weight of the column 202, carriage 208, and arms 104 over the floor. Accordingly, the cart base 204 houses heavier components, such as electronics, motors, power supply, as well as components that either enable movement and/or immobilize the cart. For example, the cart base 204 includes rolling casters 222 that allow for the cart to easily move around the room prior to a procedure. After reaching an appropriate position, the casters 222 may be immobilized using wheel locks to hold the cart 102 in place during the procedure.

Positioned at the vertical end of the column 202, the console 206 allows for both a user interface for receiving user input and a display screen (or a dual-purpose device such as, for example, a touchscreen 224) to provide the physician user with both pre-operative and intra-operative data. Potential pre-operative data on the touchscreen 224 may include pre-operative plans, navigation and mapping data derived from pre-operative computerized tomography (CT) scans, and/or notes from pre-operative patient interviews. Intra-operative data on the touchscreen 224 may include optical information provided from the tool, sensor and coordinate information from sensors, as well as vital patient statistics, such as respiration, heart rate, and/or pulse. The console 206 may be positioned and tilted to allow a physician to access the console from the side of the column 202 opposite carriage 208. From this position, the physician may view the console 206, the robotic arms 104, and the patient while operating the console 206 from behind the cart 102. As shown, the console 206 also includes a handle 226 to assist with maneuvering and stabilizing cart 102.

Figure 3A:
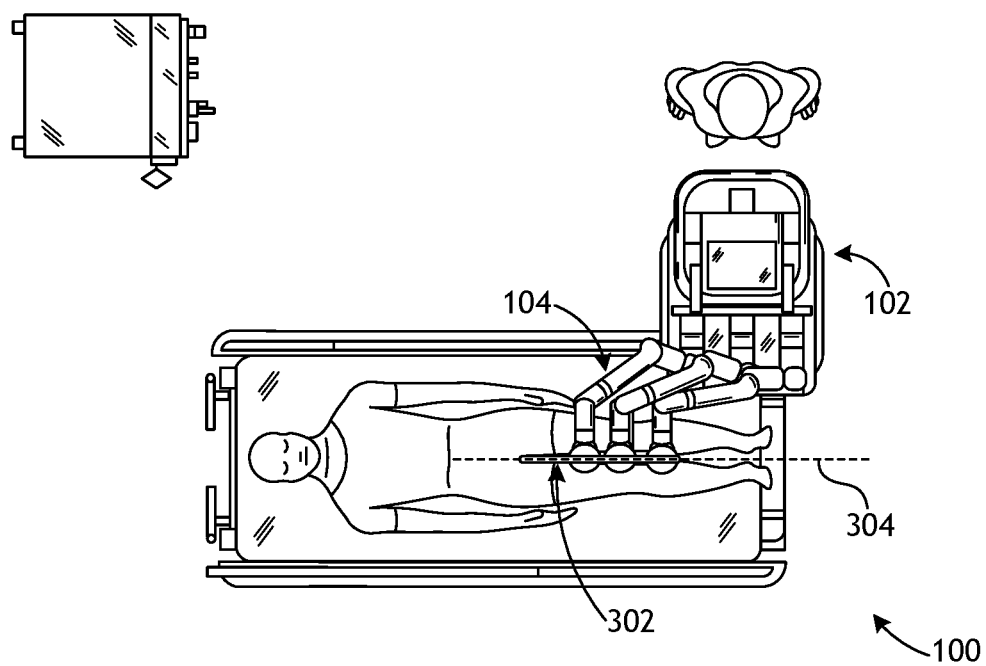
FIG. 3A illustrates an embodiment of the robotic system of FIG. 1 arranged for ureteroscopy.

FIG. 3A illustrates an embodiment of the system 100 of FIG. 1 arranged for ureteroscopy. In a ureteroscopic procedure, the cart 102 may be positioned to deliver a ureteroscope 302, a procedure-specific endoscope designed to traverse a patient's urethra and ureter, to the lower abdominal area of the patient. In ureteroscopy, it may be desirable for the ureteroscope 302 to be directly aligned with the patient's urethra to reduce friction and forces on the sensitive anatomy. As shown, the cart 102 may be aligned at the foot of the table to allow the robotic arms 104 to position the ureteroscope 302 for direct linear access to the patient's urethra. From the foot of the table, the robotic arms 104 may insert the ureteroscope 302 along a virtual rail 304 directly into the patient's lower abdomen through the urethra.

After insertion into the urethra, using similar control techniques as in bronchoscopy, the ureteroscope 302 may be navigated into the bladder, ureters, and/or kidneys for diagnostic and/or therapeutic applications. For example, the ureteroscope 302 may be directed into the ureter and kidneys to break up kidney stone build-up using a laser or ultrasonic lithotripsy device deployed down a working channel of the ureteroscope 302. After lithotripsy is complete, the resulting stone fragments may be removed using baskets deployed down the working channel of the ureteroscope 302.

Figure 3B:
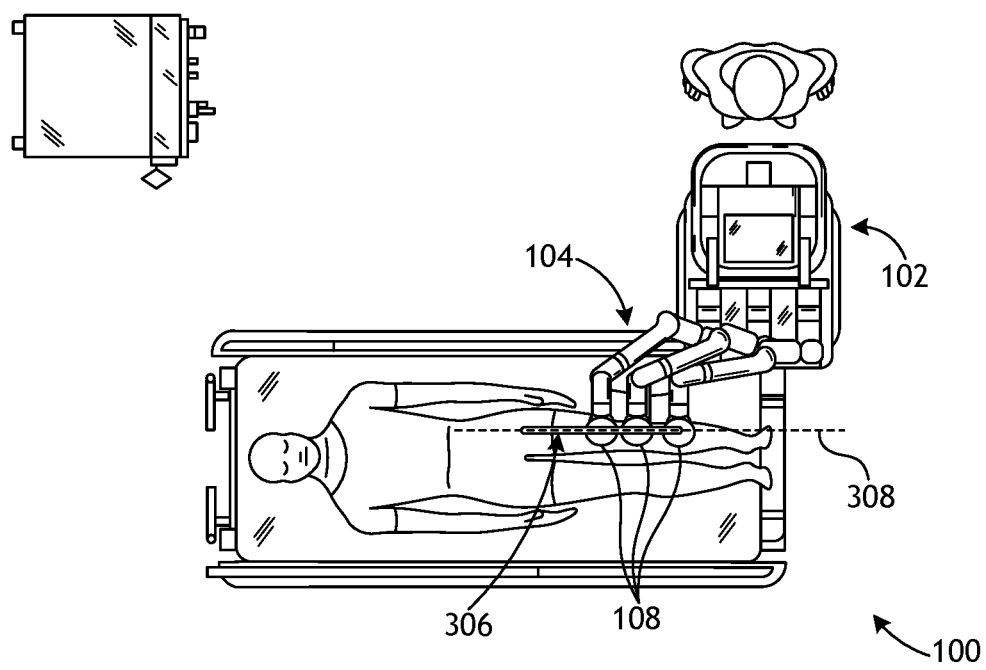
FIG. 3B illustrates an embodiment of the robotic system of FIG. 1 arranged for a vascular procedure.

FIG. 3B illustrates another embodiment of the system 100 of FIG. 1 arranged for a vascular procedure. In a vascular procedure, the system 100 may be configured such that the cart 102 may deliver a medical instrument 306, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 102 may be positioned towards the patient's legs and lower abdomen to allow the robotic arms 104 to provide a virtual rail 308 with direct linear access to the femoral artery access point in the patient's thigh/hip region. After insertion into the artery, the medical instrument 306 may be directed and advanced by translating the instrument drivers 108. Alternatively, the cart 102 may be positioned around the patient's upper abdomen in order to reach alternative vascular access points, such as, for example, the carotid and brachial arteries near the patient's shoulder and wrist.

B. Robotic System—Table.

Figure 4:
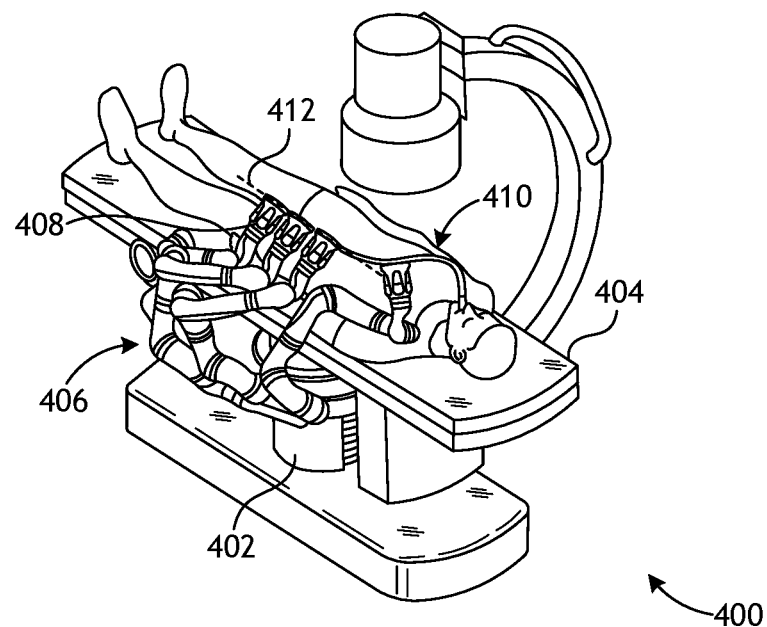
FIG. 4 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 4 illustrates an embodiment of such a robotically-enabled system 400 arranged for a bronchoscopy procedure. As illustrated, the system 400 includes a support structure or column 402 for supporting platform 404 (shown as a "table" or "bed") over the floor. Much like in the cart-based systems, the end effectors of the robotic arms 406 of the system 400 comprise instrument drivers 408 that are designed to manipulate an elongated medical instrument, such as a bronchoscope 410, through or along a virtual rail 412 formed from the linear alignment of the instrument drivers 408. In practice, a C-arm for providing fluoroscopic imaging may be positioned over the patient's upper abdominal area by placing the emitter and detector around the table 404.

Figure 5:
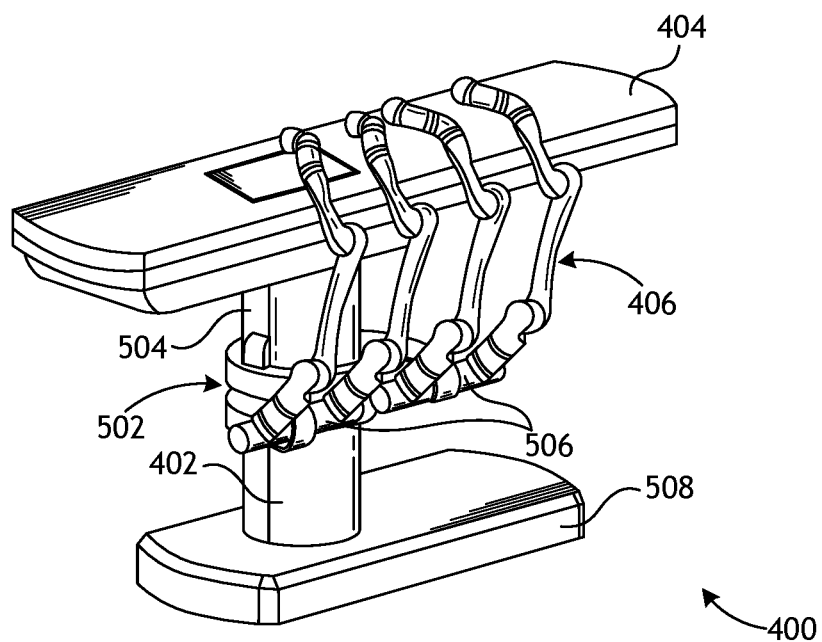
FIG. 5 provides an alternative view of the robotic system of FIG. 4.

FIG. 5 provides an alternative view of the system 400 without the patient and medical instrument for discussion purposes. As shown, the column 402 may include one or more carriages 502 shown as ring-shaped in the system 400, from which the one or more robotic arms 406 may be based. The carriages 502 may translate along a vertical column interface 504 that runs the length (height) of the column 402 to provide different vantage points from which the robotic arms 406 may be positioned to reach the patient. The carriage(s) 502 may rotate around the column 402 using a mechanical motor positioned within the column 402 to allow the robotic arms 406 to have access to multiples sides of the table 404, such as, for example, both sides of the patient. In embodiments with multiple carriages 502, the carriages 502 may be individually positioned on the column 402 and may translate and/or rotate independent of the other carriages 502. While carriages 502 need not surround the column 402 or even be circular, the ring-shape as shown facilitates rotation of the carriages 502 around the column 402 while maintaining structural balance. Rotation and translation of the carriages 502 allows the system 400 to align medical instruments, such as endoscopes and laparoscopes, into different access points on the patient.

In other embodiments (discussed in greater detail below with respect to FIG. 9A), the system 400 can include a patient table or bed with adjustable arm supports in the form of bars or rails extending alongside it. One or more robotic arms 406 (e.g., via a shoulder with an elbow joint) can be attached to the adjustable arm supports, which can be vertically adjusted. By providing vertical adjustment, the robotic arms 406 are advantageously capable of being stowed compactly beneath the patient table or bed, and subsequently raised during a procedure.

The arms 406 may be mounted on the carriages 502 through a set of arm mounts 506 comprising a series of joints that may individually rotate and/or telescopically extend to provide additional configurability to the robotic arms 406. Additionally, the arm mounts 506 may be positioned on the carriages 502 such that when the carriages 502 are appropriately rotated, the arm mounts 506 may be positioned on either the same side of the table 404 (as shown in FIG. 5), on opposite sides of table 404 (as shown in FIG. 7B), or on adjacent sides of the table 404 (not shown).

The column 402 structurally provides support for the table 404, and a path for vertical translation of the carriages 502. Internally, the column 402 may be equipped with lead screws for guiding vertical translation of the carriages, and motors to mechanize the translation of said carriages based the lead screws. The column 402 may also convey power and control signals to the carriage 502 and robotic arms 406 mounted thereon.

A table base 508 serves a similar function as the cart base 204 of the cart 102 shown in FIG. 2, housing heavier components to balance the table/bed 404, the column 402, the carriages 502, and the robotic arms 406. The table base 508 may also incorporate rigid casters to provide stability during procedures. Deployed from the bottom of the table base 508, the casters may extend in opposite directions on both sides of the base 508 and retract when the system 400 needs to be moved.

In some embodiments, the system 400 may also include a tower (not shown) that divides the functionality of system 400 between table and tower to reduce the form factor and bulk of the table 404. As in earlier disclosed embodiments, the tower may provide a variety of support functionalities to the table 404, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 508 for potential stowage of the robotic arms 406. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 6:
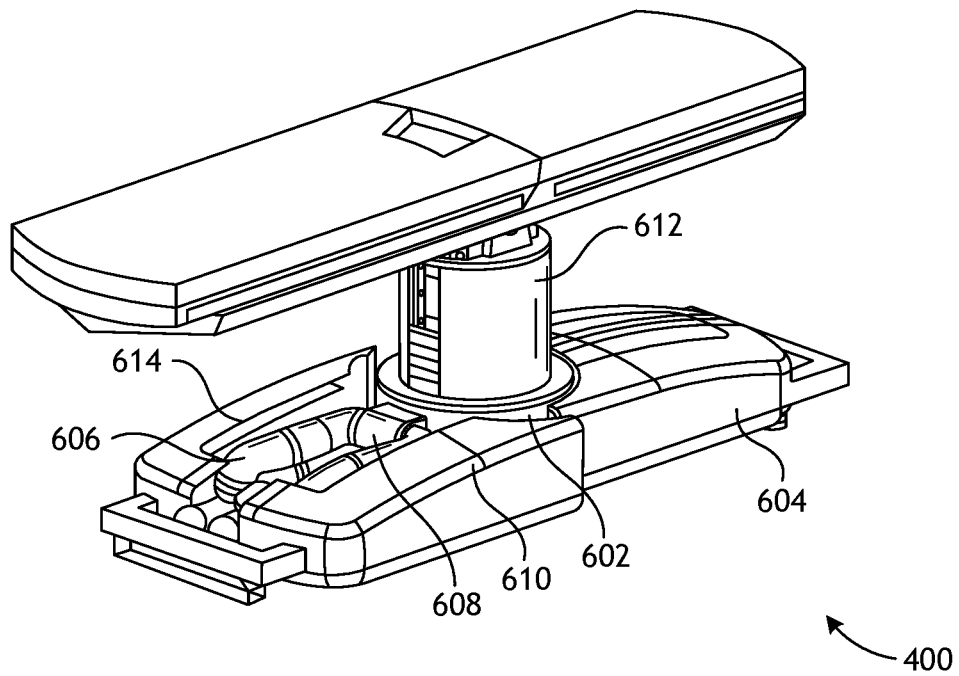
FIG. 6 illustrates an example system configured to stow robotic arm(s).

In some embodiments, a table base may stow and store the robotic arms when not in use. FIG. 6 illustrates an embodiment of the system 400 that is configured to stow robotic arms in an embodiment of the table-based system. In the system 400, one or more carriages 602 (one shown) may be vertically translated into a base 604 to stow one or more robotic arms 606, one or more arm mounts 608, and the carriages 602 within the base 604. Base covers 610 may be translated and retracted open to deploy the carriages 602, the arm mounts 608, and the arms 606 around the column 612, and closed to stow and protect them when not in use. The base covers 610 may be sealed with a membrane 614 along the edges of its opening to prevent dirt and fluid ingress when closed.

Figure 7A:
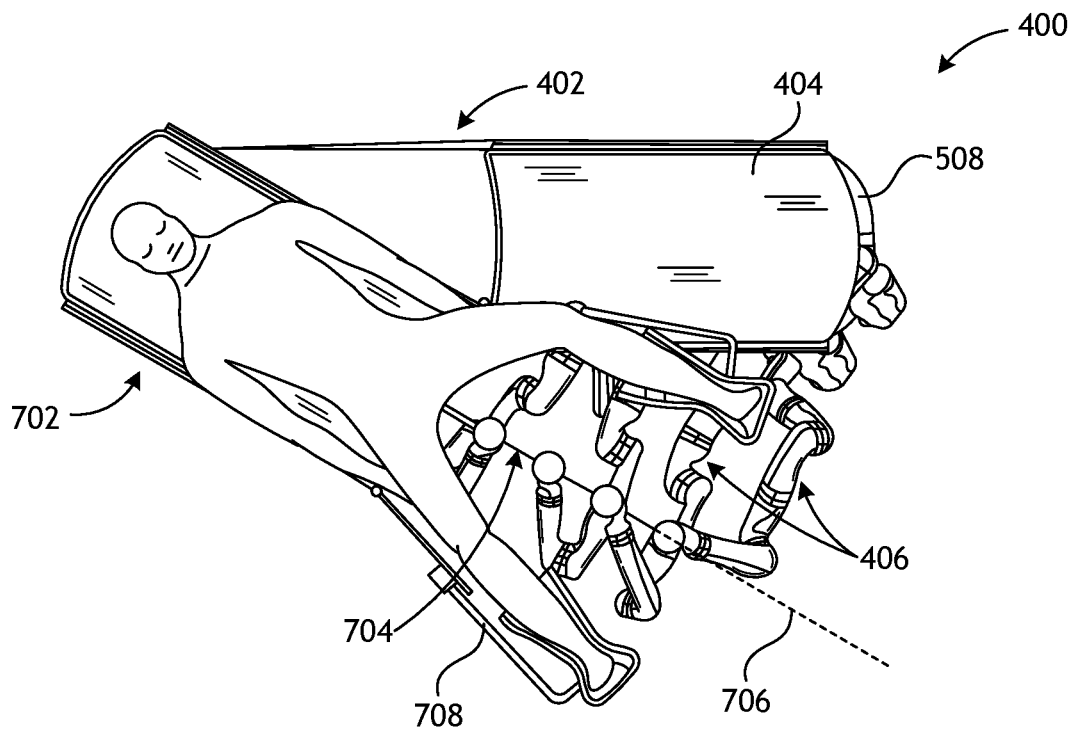
FIG. 7A illustrates an embodiment of a table-based robotic system configured for an ureteroscopy procedure.
Figure 7B:
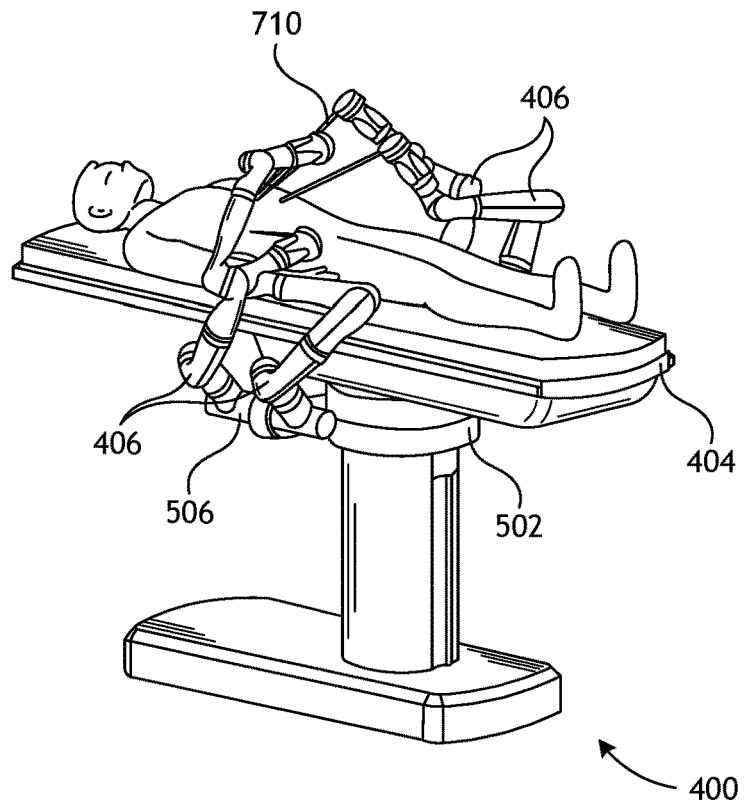
FIG. 7B illustrates an embodiment of a table-based robotic system configured for a laparoscopic procedure.

FIG. 7A illustrates an embodiment of the robotically-enabled table-based system 400 configured for a ureteroscopy procedure. In ureteroscopy, the table 404 may include a swivel portion 702 for positioning a patient off-angle from the column 402 and the table base 508. The swivel portion 702 may rotate or pivot around a pivot point (e.g., located below the patient's head) in order to position the bottom portion of the swivel portion 702 away from the column 402. For example, the pivoting of the swivel portion 702 allows a C-arm (not shown) to be positioned over the patient's lower abdomen without competing for space with the column (not shown) below table 404. By rotating the carriage (not shown) around the column 402, the robotic arms 406 may directly insert a ureteroscope 704 along a virtual rail 706 into the patient's groin area to reach the urethra. In ureteroscopy, stirrups 708 may also be fixed to the swivel portion 702 of the table 404 to support the position of the patient's legs during the procedure and allow clear access to the patient's groin area.

FIG. 7B illustrates an embodiment of the system 400 configured for a laparoscopic procedure. In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. As shown in FIG. 7B, the carriages 502 of the system 400 may be rotated and vertically adjusted to position pairs of the robotic arms 406 on opposite sides of the table 404, such that an instrument 710 may be positioned using the arm mounts 506 to be passed through minimal incisions on both sides of the patient to reach his/her abdominal cavity.

Figure 7C:
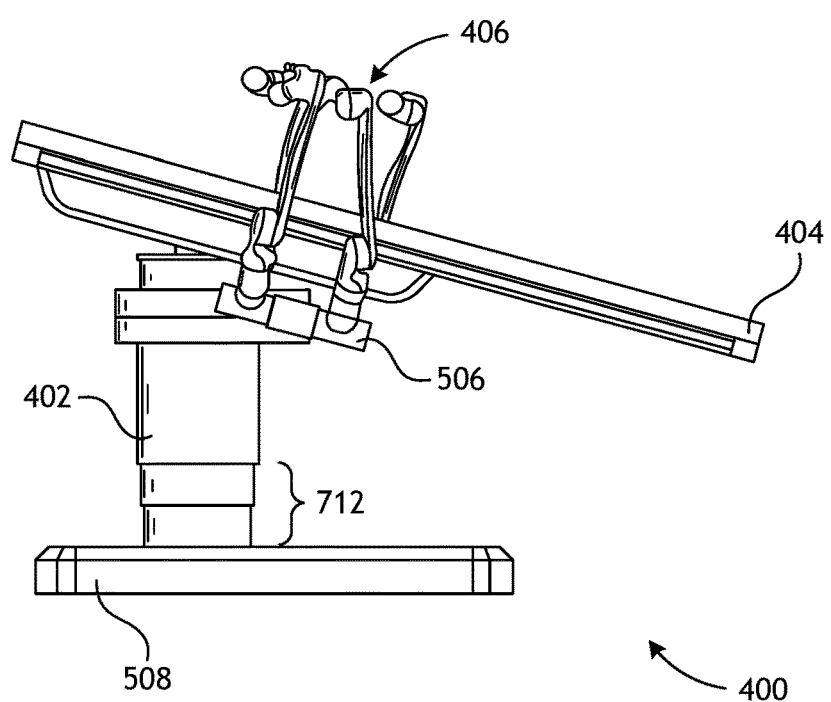
FIG. 7C illustrates an embodiment of the table-based robotic system of FIGS. 4-7B with pitch or tilt adjustment.

To accommodate laparoscopic procedures, the system 400 may also tilt the platform to a desired angle. FIG. 7C illustrates an embodiment of the system 400 with pitch or tilt adjustment. As shown in FIG. 7C, the system 400 may accommodate tilt of the table 404 to position one portion of the table 404 at a greater distance from the floor than the other. Additionally, the arm mounts 506 may rotate to match the tilt such that the arms 406 maintain the same planar relationship with table 404. To accommodate steeper angles, the column 402 may also include telescoping portions 712 that allow vertical extension of the column 402 to keep the table 404 from touching the floor or colliding with the base 508.

Figure 8:
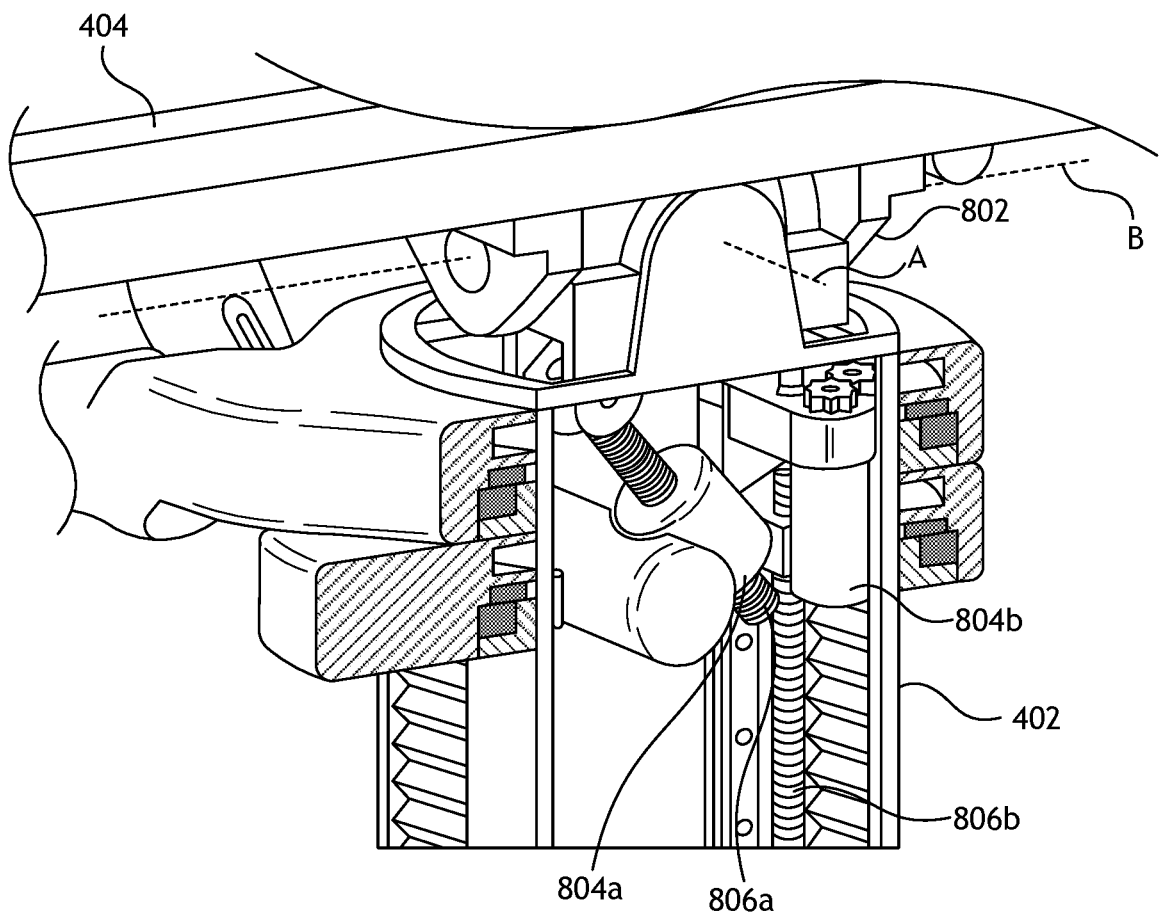
FIG. 8 provides a detailed illustration of the interface between the table and the column of the table-based robotic system of FIGS. 4-7.

FIG. 8 provides a detailed illustration of the interface between the table 404 and the column 402. Pitch rotation mechanism 802 may be configured to alter the pitch angle of the table 404 relative to the column 402 in multiple degrees of freedom. The pitch rotation mechanism 802 may be enabled by the positioning of orthogonal axes A and B at the column-table interface, each axis actuated by a separate motor 804a and 804b responsive to an electrical pitch angle command. Rotation along one screw 806a would enable tilt adjustments in one axis A, while rotation along another screw 806b would enable tilt adjustments along the other axis B. In some embodiments, a ball joint can be used to alter the pitch angle of the table 404 relative to the column 402 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery.

The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 9A:
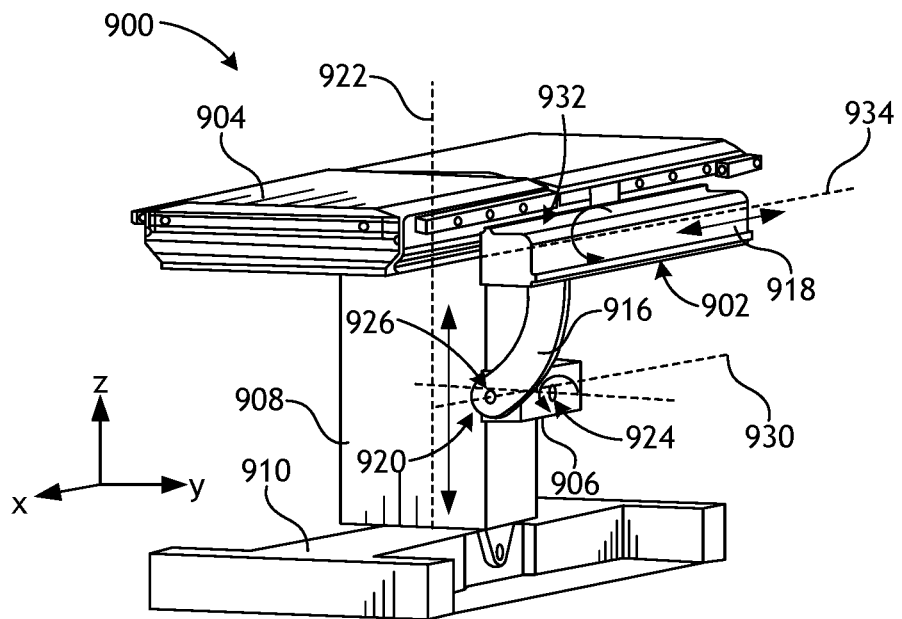
FIG. 9A illustrates an alternative embodiment of a table-based robotic system.
Figure 9B:
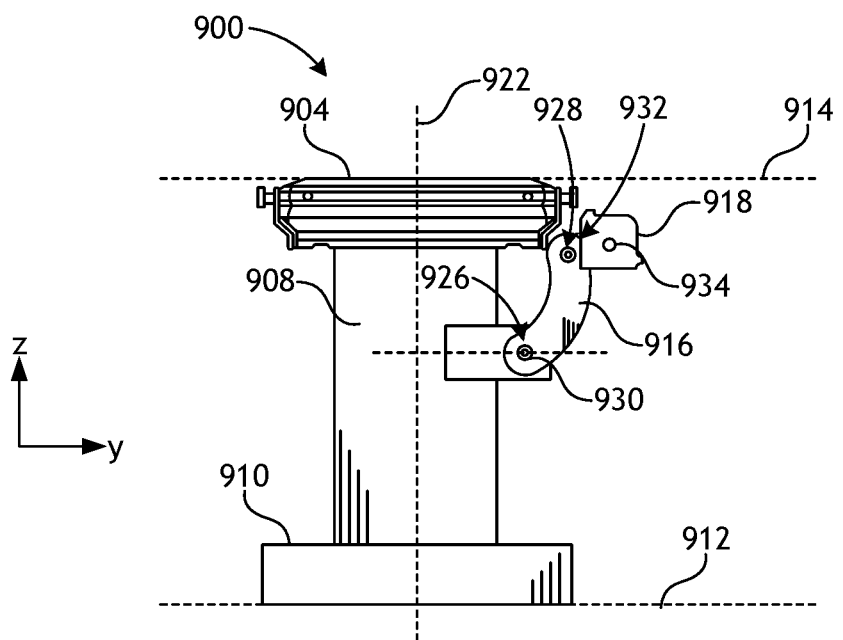
FIG. 9B illustrates an end view of the table-based robotic system of FIG. 9A.

FIGS. 9A and 9B illustrate isometric and end views, respectively, of an alternative embodiment of a table-based surgical robotics system 900. The surgical robotics system 900 includes one or more adjustable arm supports 902 that can be configured to support one or more robotic arms (see, for example, FIG. 9C) relative to a table 904. In the illustrated embodiment, a single adjustable arm support 902 is shown, though an additional arm support can be provided on an opposite side of the table 904. The adjustable arm support 902 can be configured so that it can move relative to the table 904 to adjust and/or vary the position of the adjustable arm support 902 and/or any robotic arms mounted thereto relative to the table 904. For example, the adjustable arm support 902 may be adjusted in one or more degrees of freedom relative to the table 904. The adjustable arm support 902 provides high versatility to the system 900, including the ability to easily stow the one or more adjustable arm supports 902 and any robotics arms attached thereto beneath the table 904. The adjustable arm support 902 can be elevated from the stowed position to a position below an upper surface of the table 904. In other embodiments, the adjustable arm support 902 can be elevated from the stowed position to a position above an upper surface of the table 904.

The adjustable arm support 902 can provide several degrees of freedom, including lift, lateral translation, tilt, etc. In the illustrated embodiment of FIGS. 9A and 9B, the arm support 902 is configured with four degrees of freedom, which are illustrated with arrows in FIG. 9A. A first degree of freedom allows for adjustment of the adjustable arm support 902 in the z-direction ("Z-lift"). For example, the adjustable arm support 902 can include a carriage 906 configured to move up or down along or relative to a column 908 supporting the table 904. A second degree of freedom can allow the adjustable arm support 902 to tilt. For example, the adjustable arm support 902 can include a rotary joint, which can allow the adjustable arm support 902 to be aligned with the bed in a Trendelenburg position. A third degree of freedom can allow the adjustable arm support 902 to "pivot up," which can be used to adjust a distance between a side of the table 904 and the adjustable arm support 902. A fourth degree of freedom can permit translation of the adjustable arm support 902 along a longitudinal length of the table.

The surgical robotics system 900 in FIGS. 9A and 9B can comprise a table 904 supported by a column 908 that is mounted to a base 910. The base 910 and the column 908 support the table 904 relative to a support surface. A floor axis 912 and a support axis 914 are shown in FIG. 9B.

The adjustable arm support 902 can be mounted to the column 908. In other embodiments, the arm support 902 can be mounted to the table 904 or the base 910. The adjustable arm support 902 can include a carriage 906, a bar or rail connector 916 and a bar or rail 918. In some embodiments, one or more robotic arms mounted to the rail 918 can translate and move relative to one another.

The carriage 906 can be attached to the column 908 by a first joint 920, which allows the carriage 906 to move relative to the column 908 (e.g., such as up and down a first or vertical axis 922). The first joint 920 can provide the first degree of freedom ("Z-lift") to the adjustable arm support 902. The adjustable arm support 902 can include a second joint 924, which provides the second degree of freedom (tilt) for the adjustable arm support 902. The adjustable arm support 902 can include a third joint 926, which can provide the third degree of freedom ("pivot up") for the adjustable arm support 902. An additional joint 928 (shown in FIG. 9B) can be provided that mechanically constrains the third joint 926 to maintain an orientation of the rail 918 as the rail connector 916 is rotated about a third axis 930. The adjustable arm support 902 can include a fourth joint 932, which can provide a fourth degree of freedom (translation) for the adjustable arm support 902 along a fourth axis 934.

Figure 9C:
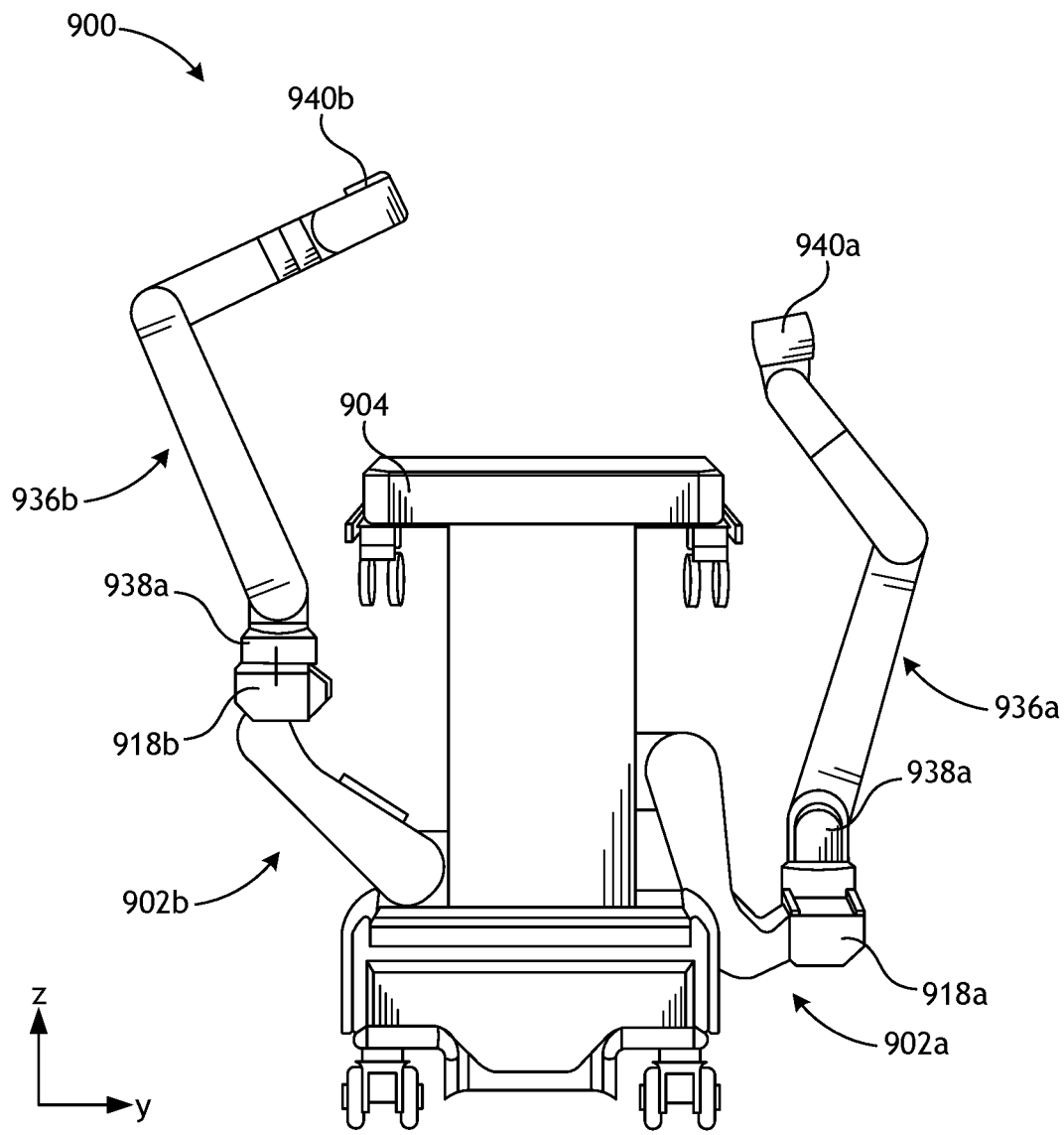
FIG. 9C illustrates an end view of a table-based robotic system with robotic arms attached thereto.

FIG. 9C illustrates an end view of the surgical robotics system 900 with two adjustable arm supports 902a and 902b mounted on opposite sides of the table 904. A first robotic arm 936a is attached to the first bar or rail 918a of the first adjustable arm support 902a. The first robotic arm 936a includes a base 938a attached to the first rail 918a. The distal end of the first robotic arm 936a includes an instrument drive mechanism or input 940a that can attach to one or more robotic medical instruments or tools. Similarly, the second robotic arm 936b includes a base 938a attached to the second rail 918b. The distal end of the second robotic arm 936b includes an instrument drive mechanism or input 940b configured to attach to one or more robotic medical instruments or tools.

In some embodiments, one or more of the robotic arms 936a,b comprises an arm with seven or more degrees of freedom. In some embodiments, one or more of the robotic arms 936a,b can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 938a,b (1-degree of freedom including translation). In some embodiments, the insertion degree of freedom can be provided by the robotic arm 936a,b, while in other embodiments, the instrument itself provides insertion via an instrument-based insertion architecture.

C. Instrument Driver & Interface.

The end effectors of a system's robotic arms comprise (i) an instrument driver (alternatively referred to as "instrument drive mechanism," "instrument device manipulator," and "drive input") that incorporate electro-mechanical means for actuating the medical instrument, and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 10:
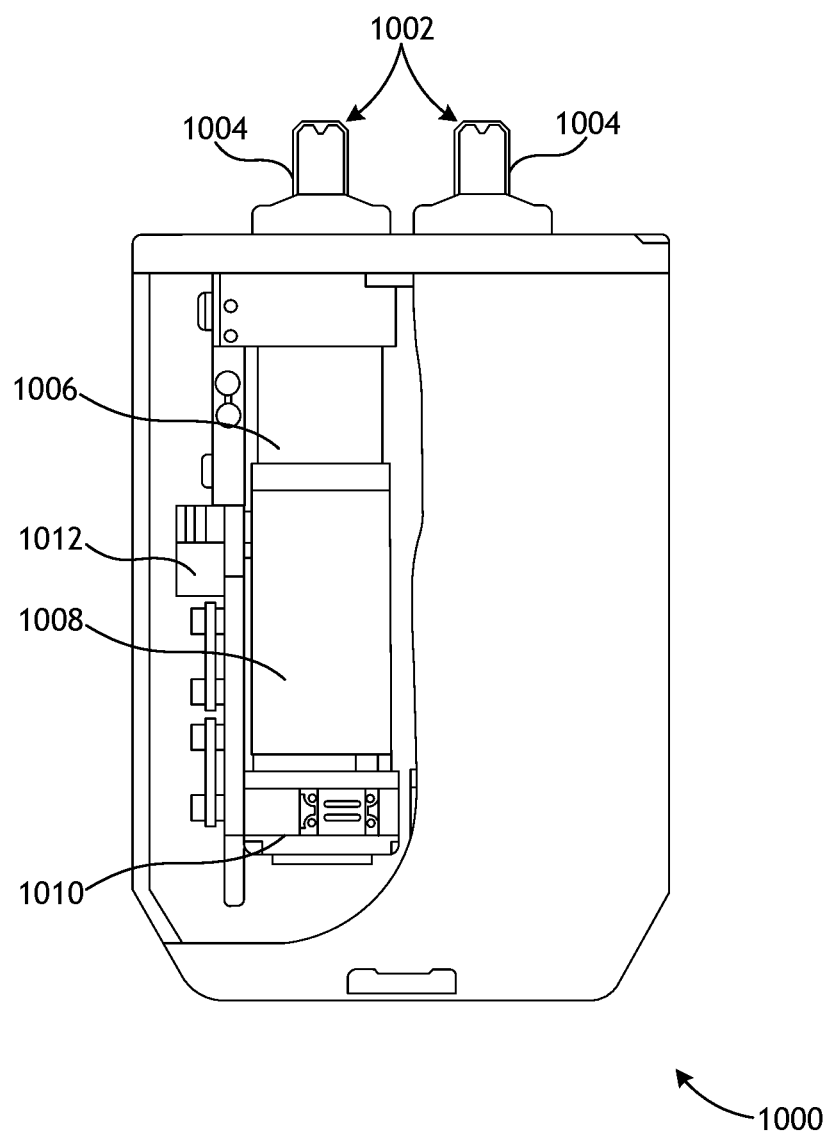
FIG. 10 illustrates an exemplary instrument driver.

FIG. 10 illustrates an example instrument driver 1000, according to one or more embodiments. Positioned at the distal end of a robotic arm, the instrument driver 1000 comprises of one or more drive outputs 1002 arranged with parallel axes to provide controlled torque to a medical instrument via corresponding drive shafts 1004. Each drive output 1002 comprises an individual drive shaft 1004 for interacting with the instrument, a gear head 1006 for converting the motor shaft rotation to a desired torque, a motor 1008 for generating the drive torque, and an encoder 1010 to measure the speed of the motor shaft and provide feedback to control circuitry 1012, which can also be used for receiving control signals and actuating the drive output 1002. Each drive output 1002 being independent controlled and motorized, the instrument driver 1000 may provide multiple (at least two shown in FIG. 10) independent drive outputs to the medical instrument. In operation, the control circuitry 1012 receives a control signal, transmits a motor signal to the motor 1008, compares the resulting motor speed as measured by the encoder 1010 with the desired speed, and modulates the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 11:
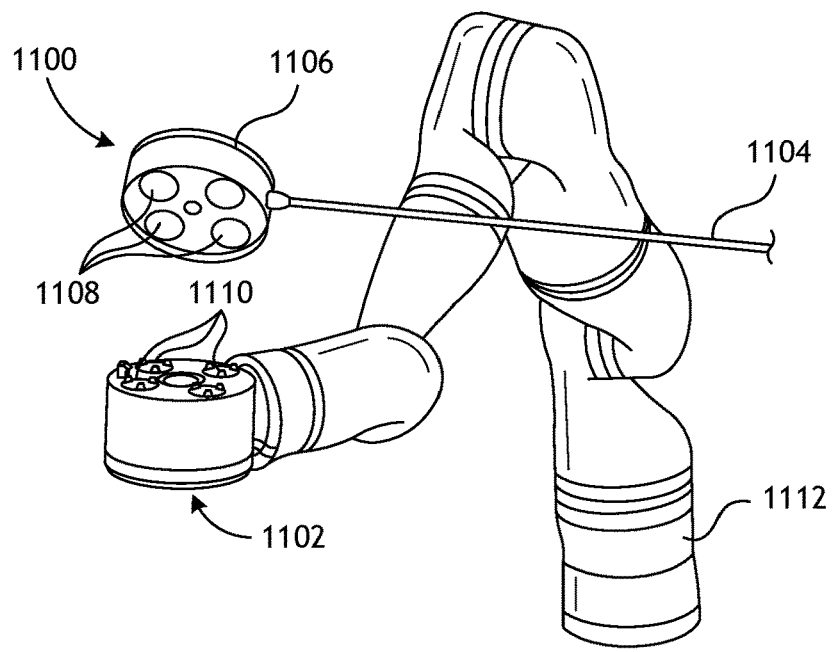
FIG. 11 illustrates an exemplary medical instrument with a paired instrument driver.

FIG. 11 illustrates an example medical instrument 1100 with a paired instrument driver 1102. Like other instruments designed for use with a robotic system, the medical instrument 1100 (alternately referred to as a "surgical tool") comprises an elongated shaft 1104 (or elongate body) and an instrument base 1106. The instrument base 1106, also referred to as an "instrument handle" due to its intended design for manual interaction by the physician, may generally comprise rotatable drive inputs 1108, e.g., receptacles, pulleys or spools, that are designed to be mated with drive outputs 1110 that extend through a drive interface on the instrument driver 1102 at the distal end of a robotic arm 1112. When physically connected, latched, and/or coupled, the mated drive inputs 1108 of the instrument base 1106 may share axes of rotation with the drive outputs 1110 in the instrument driver 1102 to allow the transfer of torque from the drive outputs 1110 to the drive inputs 1108. In some embodiments, the drive outputs 1110 may comprise splines that are designed to mate with receptacles on the drive inputs 1108.

The elongated shaft 1104 is designed to be delivered through either an anatomical opening or lumen, e.g., as in endoscopy, or a minimally invasive incision, e.g., as in laparoscopy. The elongated shaft 1104 may be either flexible (e.g., having properties similar to an endoscope) or rigid (e.g., having properties similar to a laparoscope) or contain a customized combination of both flexible and rigid portions. When designed for laparoscopy, the distal end of the shaft 1104 may be connected to an end effector extending from a jointed wrist formed from a clevis with at least one degree of freedom and a surgical tool or medical instrument, such as, for example, a grasper or scissors, that may be actuated based on force from the tendons as the drive inputs 1008 rotate in response to torque received from the drive outputs 1110 of the instrument driver 1102. When designed for endoscopy, the distal end of the flexible elongated shaft 1104 may include a steerable or controllable bending section that may be articulated and bent based on torque received from the drive outputs 1110 of the instrument driver 1102.

In some embodiments, torque from the instrument driver 1102 is transmitted down the elongated shaft 1104 using tendons along the shaft 1104. These individual tendons, such as pull wires, may be individually anchored to individual drive inputs 1108 within the instrument handle 1106. From the handle 1106, the tendons are directed down one or more pull lumens along the elongated shaft 1104 and anchored at the distal portion of the elongated shaft 1104, or in the wrist at the distal portion of the elongated shaft. During a surgical procedure, such as a laparoscopic, endoscopic, or a hybrid procedure, these tendons may be coupled to a distally mounted end effector, such as a wrist, a grasper, or scissors. Under such an arrangement, torque exerted on the drive inputs 1108 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 1104, where tension from the tendon cause the grasper to close.

In endoscopy, the tendons may be coupled to a bending or articulating section positioned along the elongated shaft 1104 (e.g., at the distal end) via adhesive, control ring, or other mechanical fixation. When fixedly attached to the distal end of a bending section, torque exerted on drive inputs 1108 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 1104 to allow for controlled articulation in the desired bending or articulable sections.

In endoscopy, the elongated shaft 1104 houses a number of components to assist with the robotic procedure. The shaft may comprise of a working channel for deploying surgical tools (or medical instruments), irrigation, and/or aspiration to the operative region at the distal end of the shaft 1104. The shaft 1104 may also accommodate wires and/or optical fibers to transfer signals to/from an optical assembly at the distal tip, which may include of an optical camera. The shaft 1104 may also accommodate optical fibers to carry light from proximally-located light sources, such as light emitting diodes, to the distal end of the shaft.

At the distal end of the instrument 1100, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 11, the drive shaft axes, and thus the drive input axes, are orthogonal to the axis of the elongated shaft. This arrangement, however, complicates roll capabilities for the elongated shaft 1104. Rolling the elongated shaft 1104 along its axis while keeping the drive inputs 1108 static results in undesirable tangling of the tendons as they extend off the drive inputs 1108 and enter pull lumens within the elongated shaft 1104. The resulting entanglement of such tendons may disrupt any control algorithms intended to predict movement of the flexible elongated shaft during an endoscopic procedure.

Figure 12:
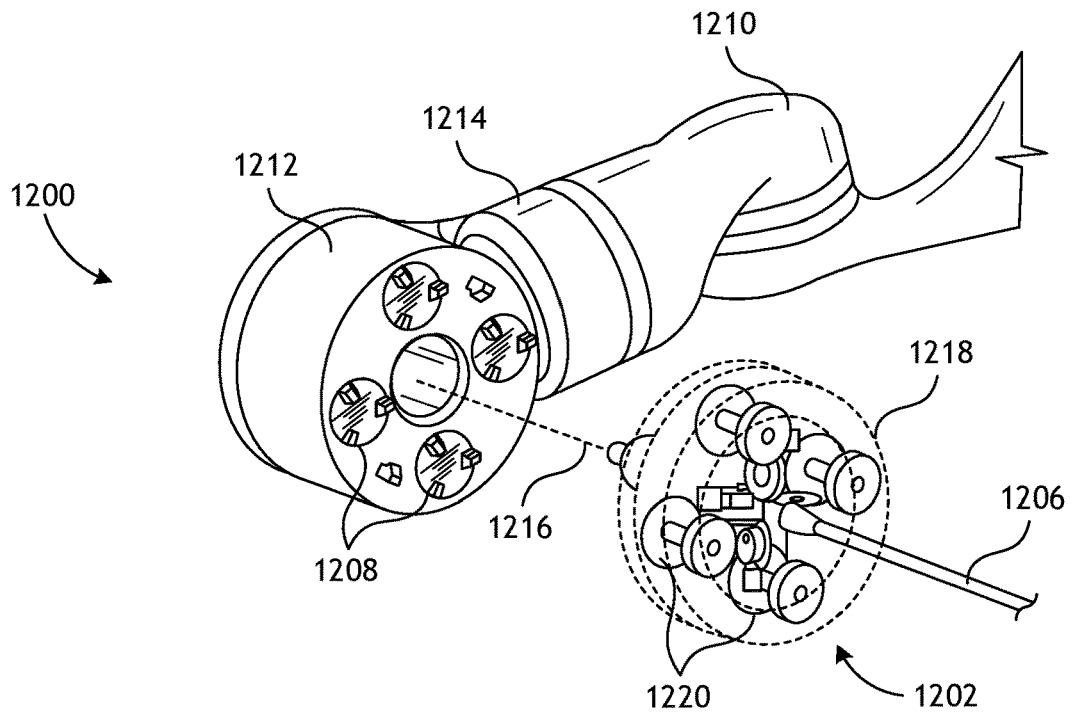
FIG. 12 illustrates an alternative design for an instrument driver and instrument where the axes of the drive units are parallel to the axis of the elongated shaft of the instrument.

FIG. 12 illustrates an alternative design for a circular instrument driver 1200 and corresponding instrument 1202 (alternately referred to as a "surgical tool") where the axes of the drive units are parallel to the axis of the elongated shaft 1206 of the instrument 1202.

As shown, the instrument driver 1200 comprises four drive units with corresponding drive outputs 1208 aligned in parallel at the end of a robotic arm 1210. The drive units and their respective drive outputs 1208 are housed in a rotational assembly 1212 of the instrument driver 1200 that is driven by one of the drive units within the assembly 1212. In response to torque provided by the rotational drive unit, the rotational assembly 1212 rotates along a circular bearing that connects the rotational assembly 1212 to a non-rotational portion 1214 of the instrument driver 1200. Power and control signals may be communicated from the non-rotational portion 1214 of the instrument driver 1200 to the rotational assembly 1212 through electrical contacts maintained through rotation by a brushed slip ring connection (not shown). In other embodiments, the rotational assembly 1212 may be responsive to a separate drive unit that is integrated into the non-rotatable portion 1214, and thus not in parallel with the other drive units. The rotational assembly 1212 allows the instrument driver 1200 to rotate the drive units and their respective drive outputs 1208 as a single unit around an instrument driver axis 1216.

Like earlier disclosed embodiments, the instrument 1202 may include an elongated shaft 1206 and an instrument base 1218 (shown in phantom) including a plurality of drive inputs 1220 (such as receptacles, pulleys, and spools) that are configured to mate with the drive outputs 1208 of the instrument driver 1200. Unlike prior disclosed embodiments, the instrument shaft 1206 extends from the center of the instrument base 1218 with an axis substantially parallel to the axes of the drive inputs 1220, rather than orthogonal as in the design of FIG. 11.

When coupled to the rotational assembly 1212 of the instrument driver 1200, the medical instrument 1202, comprising instrument base 1218 and instrument shaft 1206, rotates in combination with the rotational assembly 1212 about the instrument driver axis 1216. Since the instrument shaft 1206 is positioned at the center of the instrument base 1218, the instrument shaft 1206 is coaxial with the instrument driver axis 1216 when attached. Thus, rotation of the rotational assembly 1212 causes the instrument shaft 1206 to rotate about its own longitudinal axis. Moreover, as the instrument base 1218 rotates with the instrument shaft 1206, any tendons connected to the drive inputs 1220 in the instrument base 1218 are not tangled during rotation. Accordingly, the parallelism of the axes of the drive outputs 1208, the drive inputs 1220, and the instrument shaft 1206 allows for the shaft rotation without tangling any control tendons.

Figure 13:
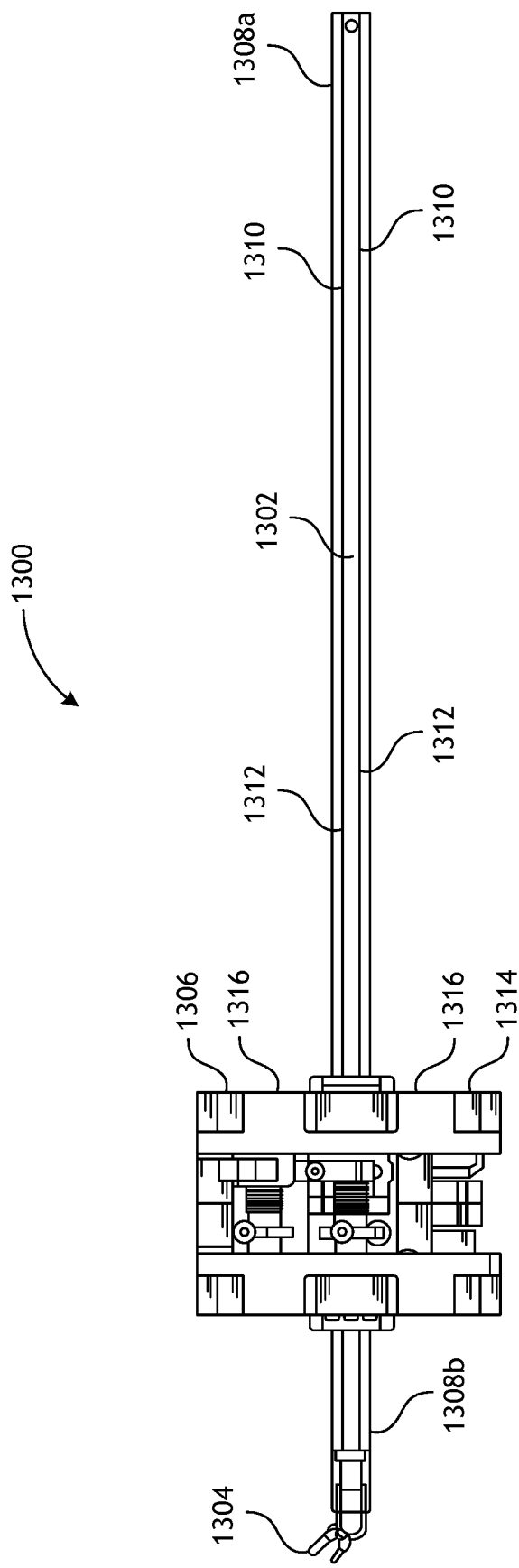
FIG. 13 illustrates an instrument having an instrument-based insertion architecture.

FIG. 13 illustrates a medical instrument 1300 having an instrument based insertion architecture in accordance with some embodiments. The instrument 1300 (alternately referred to as a "surgical tool") can be coupled to any of the instrument drivers discussed herein above and, as illustrated, can include an elongated shaft 1302, an end effector 1304 connected to the shaft 1302, and a handle 1306 coupled to the shaft 1302. The elongated shaft 1302 comprises a tubular member having a proximal portion 1308a and a distal portion 1308b. The elongated shaft 1302 comprises one or more channels or grooves 1310 along its outer surface and configured to receive one or more wires or cables 1312 therethrough. One or more cables 1312 thus run along an outer surface of the elongated shaft 1302. In other embodiments, the cables 1312 can also run through the elongated shaft 1302. Manipulation of the cables 1312 (e.g., via an instrument driver) results in actuation of the end effector 1304.

The instrument handle 1306, which may also be referred to as an instrument base, may generally comprise an attachment interface 1314 having one or more mechanical inputs 1316, e.g., receptacles, pulleys or spools, that are designed to be reciprocally mated with one or more drive outputs on an attachment surface of an instrument driver.

In some embodiments, the instrument 1300 comprises a series of pulleys or cables that enable the elongated shaft 1302 to translate relative to the handle 1306. In other words, the instrument 1300 itself comprises an instrument-based insertion architecture that accommodates insertion of the instrument, thereby minimizing the reliance on a robot arm to provide insertion of the instrument 1300. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 14:
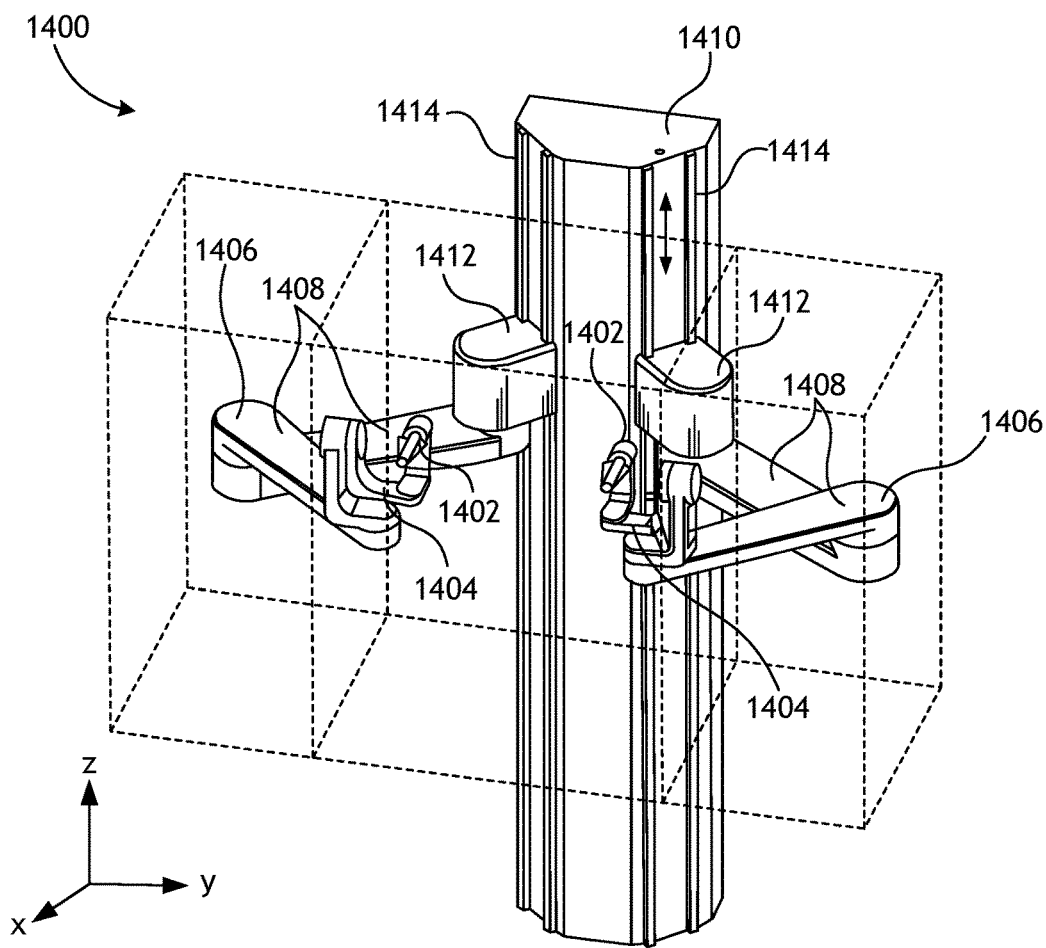
FIG. 14 illustrates an exemplary controller.

FIG. 14 is a perspective view of an embodiment of a controller 1400. In the present embodiment, the controller 1400 comprises a hybrid controller that can have both impedance and admittance control. In other embodiments, the controller 1400 can utilize just impedance or passive control. In other embodiments, the controller 1400 can utilize just admittance control. By being a hybrid controller, the controller 1400 advantageously can have a lower perceived inertia while in use.

In the illustrated embodiment, the controller 1400 is configured to allow manipulation of two medical instruments, and includes two handles 1402. Each of the handles 1402 is connected to a gimbal 1404, and each gimbal 1404 is connected to a positioning platform 1406.

As shown in FIG. 14, each positioning platform 1406 includes a selective compliance assembly robot arm (SCARA) 1408 coupled to a column 1410 by a prismatic joint 1412. The prismatic joints 1412 are configured to translate along the column 1410 (e.g., along rails 1414) to allow each of the handles 1402 to be translated in the z-direction, providing a first degree of freedom. The SCARA arm 1408 is configured to allow motion of the handle 1402 in an x-y plane, providing two additional degrees of freedom.

In some embodiments, one or more load cells are positioned in the controller 1400. For example, in some embodiments, a load cell (not shown) is positioned in the body of each of the gimbals 1404. By providing a load cell, portions of the controller 1400 are capable of operating under admittance control, thereby advantageously reducing the perceived inertia of the controller 1400 while in use. In some embodiments, the positioning platform 1406 is configured for admittance control, while the gimbal 1404 is configured for impedance control. In other embodiments, the gimbal 1404 is configured for admittance control, while the positioning platform 1406 is configured for impedance control. Accordingly, for some embodiments, the translational or positional degrees of freedom of the positioning platform 1406 can rely on admittance control, while the rotational degrees of freedom of the gimbal 1404 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
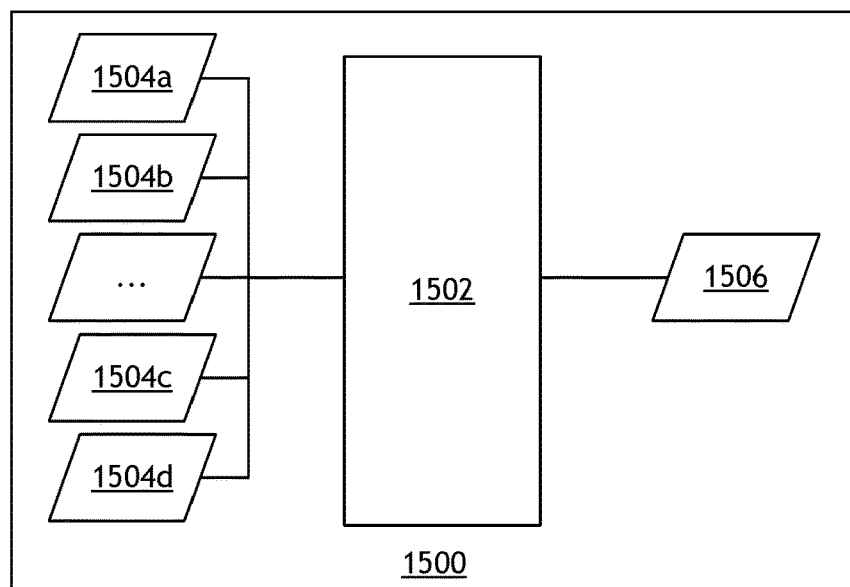
FIG. 15 depicts a block diagram illustrating a localization system that estimates a location of one or more elements of the robotic systems of FIGS. 1-7C, such as the location of the instrument of FIGS. 11-13, in accordance to an example embodiment.

FIG. 15 is a block diagram illustrating a localization system 1500 that estimates a location of one or more elements of the robotic system, such as the location of the instrument, in accordance to an example embodiment. The localization system 1500 may be a set of one or more computer devices configured to execute one or more instructions. The computer devices may be embodied by a processor (or processors) and computer-readable memory in one or more components discussed above. By way of example and not limitation, the computer devices may be in the tower 112 shown in FIG. 1, the cart 102 shown in FIGS. 1-3B, the beds shown in FIGS. 4-9, etc.

As shown in FIG. 15, the localization system 1500 may include a localization module 1502 that processes input data 1504*a*, 1504*b*, 1504*c*, and 1504*d* to generate location data 1506 for the distal tip of a medical instrument. The location data 1506 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 1504*a-d* are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 1504*a* (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 1504*b*. The localization module 1502 may process the vision data 1504*b* to enable one or more vision-based location tracking. For example, the preoperative model data may be used in conjunction with the vision data 1504*b* to enable computer vision-based tracking of the medical instrument (e.g., an endoscope or an instrument advance through a working channel of the endoscope). For example, using the preoperative model data 1504*a*, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 1502 may identify circular geometries in the preoperative model data 1504*a* that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 1504*b* to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 1502 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 1504*c*. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 1504*d* may also be used by the localization module 1502 to provide localization data 1506 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 1502. For example, although not shown in FIG. 15, an instrument utilizing shape-sensing fiber can provide shape data that the localization module 1502 can use to determine the location and shape of the instrument.

The localization module 1502 may use the input data 1504*a-d* in combination(s). In some cases, such a combination may use a probabilistic approach where the localization module 1502 assigns a confidence weight to the location determined from each of the input data 1504*a-d*. Thus, where the EM data 1504*c* may not be reliable (as may be the case where there is EM interference) the confidence of the location determined by the EM data 1504*c* can be decrease and the localization module 1502 may rely more heavily on the vision data 1504*b* and/or the robotic command and kinematics data 1504*d*.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction.

Embodiments of this disclosure relate to structural considerations and techniques for robotic surgical tools for a robotic instrument driver. The robotic surgical tool may include a handle having a first end, at least one spline rotatably coupled to the handle and extending proximally from the first end. The robotic surgical tool includes a layered carriage architecture. That is, the carriage is movably mounted to the at least one spline and includes a first layer and a second layer operatively coupled to the first layer. At least one spline extends through a portion of at least one of the first and second layers and the carriage translates along the at least one spline. The robotic surgical tool also includes an elongate shaft extending from the carriage and penetrating the first end, the shaft having an end effector arranged at a distal end thereof and an activating mechanism coupled to one or both of the first and second layers and actuatable to operate a function of the end effector.

3. Description.

Figure 16A:
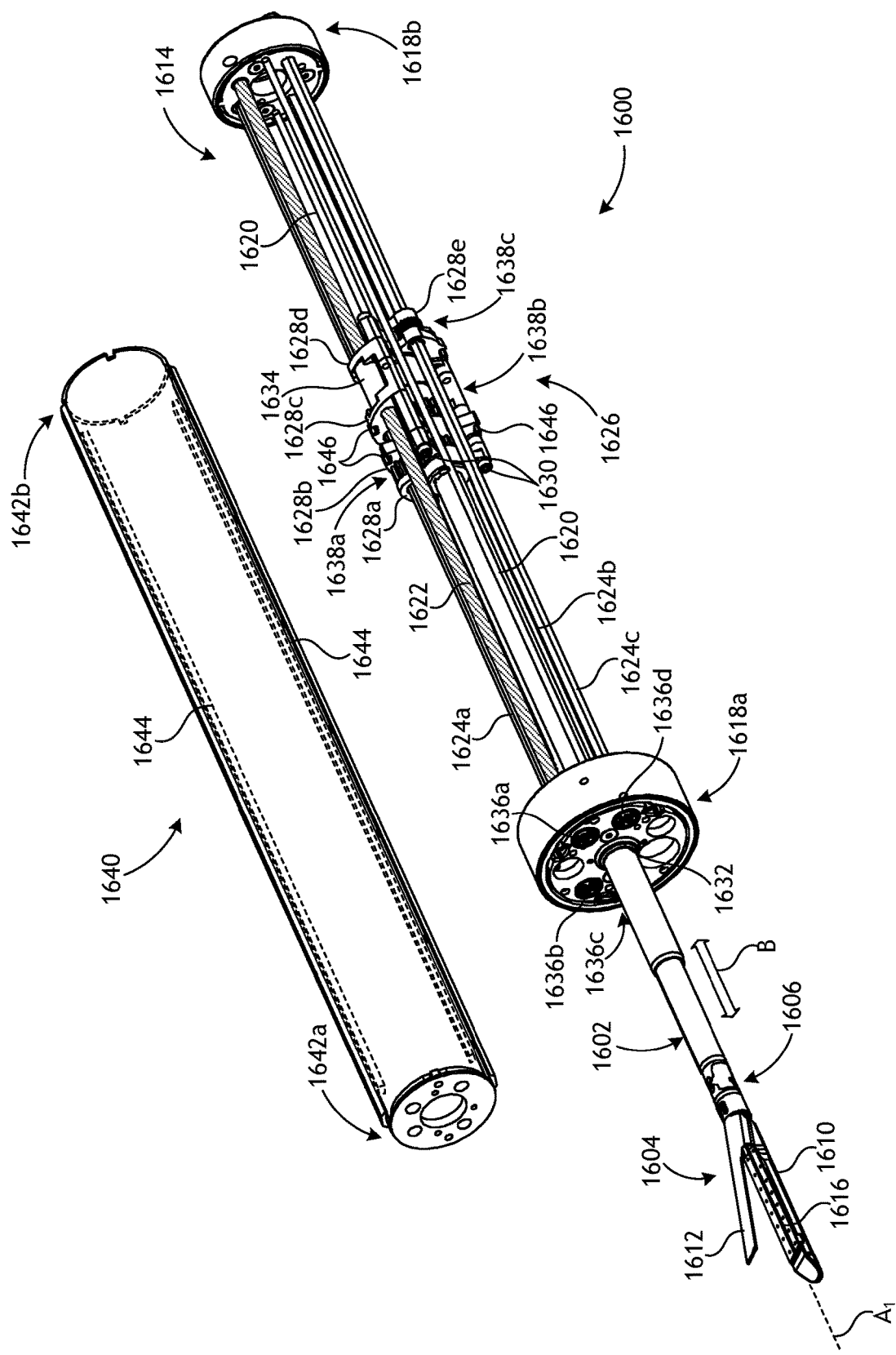
FIG. 16A is an isometric side view of an example surgical tool that may incorporate some or all of the principles of the present disclosure.

FIG. 16A is an isometric side view of an example surgical tool 1600 that may incorporate some or all of the principles of the present disclosure. The surgical tool 1600 may be similar in some respects to any of the medical instruments described above with reference to FIGS. 11-13 and, therefore, may be used in conjunction with a robotic surgical system, such as the robotically-enabled systems 100, 400, and 900 of FIGS. 1-13. As illustrated, the surgical tool 1600 includes an elongated shaft 1602, an end effector 1604 arranged at the distal end of the shaft 1602, and an articulable wrist 1606 (alternately referred to as a "wrist joint") that interposes and couples the end effector 1604 to the distal end of the shaft 1602.

The terms "proximal" and "distal" are defined herein relative to a robotic surgical system having an interface configured to mechanically and electrically couple the surgical tool 1600 to a robotic manipulator. The term "proximal" refers to the position of an element closer to the robotic manipulator and the term "distal" refers to the position of an element closer to the end effector 1604 and thus closer to the patient during operation. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

The surgical tool 1600 can have any of a variety of configurations capable of performing one or more surgical functions. In the illustrated embodiment, the end effector 1604 comprises a surgical stapler, alternately referred to as an "endocutter," configured to cut and staple (fasten) tissue. As illustrated, the end effector 1604 includes opposing jaws 1610, 1612 configured to move (articulate) between open and closed positions. Alternatively, the end effector 1604 may comprise other types of instruments requiring opposing jaws such as, but not limited to, tissue graspers, surgical scissors, advanced energy vessel sealers, clip appliers, needle drivers, a babcock including a pair of opposed grasping jaws, bipolar jaws (e.g., bipolar Maryland grasper, forceps, a fenestrated grasper, etc.), etc. In other embodiments, the end effector 1604 may instead comprise any end effector or instrument capable of being operated in conjunction with the presently disclosed robotic surgical systems and methods. Such end effectors or instruments include, but are not limited to, a suction irrigator, an endoscope (e.g., a camera), or any combination thereof One or both of the jaws 1610, 1612 may be configured to pivot to actuate the end effector 1604 between open and closed positions. In the illustrated example, the second jaw 1612 is rotatable (pivotable) relative to the first jaw 1610 to move between an open, unclamped position and a closed, clamped position. In other embodiments, however, the first jaw 1610 may move (rotate) relative to the second jaw 1612, without departing from the scope of the disclosure. In yet other embodiments, both jaws 1610, 1612 may move to actuate the end effector 1604 between open and closed positions.

In the illustrated example, the first jaw 1610 is referred to as a "cartridge" or "channel" jaw, and the second jaw 1612 is referred to as an "anvil" jaw. The first jaw 1610 may include a frame that houses or supports a staple cartridge, and the second jaw 1612 is pivotally supported relative to the first jaw 1610 and defines a surface that operates as an anvil to deform staples ejected from the staple cartridge during operation.

The wrist 1606 enables the end effector 1604 to articulate (pivot) relative to the shaft 1602 and thereby position the end effector 1604 at various desired orientations and locations relative to a surgical site. In the illustrated embodiment, the wrist 1606 is designed to allow the end effector 1604 to pivot (swivel) left and right relative to a longitudinal axis $A_1$ of the shaft 1602. In other embodiments, however, the wrist 1606 may be designed to provide multiple degrees of freedom, including one or more translational variables (i.e., surge, heave, and sway) and/or one or more rotational variables (i.e., Euler angles or roll, pitch, and yaw). The translational and rotational variables describe the position and orientation of a component of a surgical system (e.g., the end effector 1604) with respect to a given reference Cartesian frame. "Surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

In the illustrated embodiment, the pivoting motion at the wrist 1606 is limited to movement in a single plane, e.g., only yaw movement relative to the longitudinal axis $A_1$. The end effector 1604 is depicted in FIG. 16A in the unarticulated position where the longitudinal axis of the end effector 1604 is substantially aligned with the longitudinal axis $A_1$ of the shaft 1602, such that the end effector 1604 is at a substantially zero angle relative to the shaft 1602. In the articulated position, the longitudinal axis of the end effector 1604 would be angularly offset from the longitudinal axis $A_1$ such that the end effector 1604 would be oriented at a non-zero angle relative to the shaft 1602.

Still referring to FIG. 16A, the surgical tool 1600 may include a drive housing or "handle" 1614 that operates as an actuation system designed to facilitate articulation of the wrist 1606 and actuation (operation) of the end effector 1604 (e.g., clamping, firing, rotation, articulation, energy delivery, etc.). As described in more detail below, the handle 1614 provides various coupling features that releasably couple the surgical tool 1600 to an instrument driver of a robotic surgical system.

The handle 1614 includes a plurality of drive members (obscured in FIG. 16A) that extend to the wrist 1606 and the end effector 1604. Selective actuation of one or more of the drive members causes the end effector 1604 to articulate (pivot) relative to the shaft 1602 at the wrist 1606. Selective actuation of one or more other drive members causes the end effector 1604 to actuate (operate). Actuating the end effector 1604 may include closing and/or opening the jaws, 1610, 1612, and thereby enabling the end effector 1604 to grasp (clamp) onto tissue. Once tissue is grasped or clamped between the opposing jaws 1610, 1612, actuating the end effector 1604 may further include "firing" the end effector 1604, which may refer to causing a cutting element or knife (not visible) to advance distally within a slot 1616 defined in the first jaw 1610. As it moves distally, the cutting element transects any tissue grasped between the opposing jaws 1610, 1612. Moreover, as the cutting element advances distally, a plurality of staples contained within the staple cartridge (e.g., housed within the first jaw 1610) are urged (cammed) into deforming contact with corresponding anvil surfaces (e.g., pockets) provided on the second jaw 1612. The deployed staples may form multiple rows of staples that seal opposing sides of the transected tissue.

As illustrated, the handle 1614 has a first or "distal" end 1618a and a second or "proximal" end 1618b opposite the first end 1618a. In some embodiments, one or more struts 1620 (two shown) extend longitudinally between the first and second ends 1618a,b to help fix the distance between the first and second ends 1618a,b, provide structural stability to the handle 1614, and secure the first end 1618a to the second end 1618b. In other embodiments, however, the struts 1620 may be omitted, without departing from the scope of the disclosure.

The handle 1614 may also include a lead screw 1622 and one or more splines 1624, which also extend longitudinally between the first and second ends 1618a,b. In the illustrated embodiment, the handle 1614 includes a first spline 1624a, a second spline 1624b, and a third spline 1624c. While three splines 1624a-c are depicted in the handle 1614, more or less than three may be included, without departing from the scope of the disclosure. Unlike the struts 1620, the lead screw 1622 and the splines 1624a-c are rotatably mounted to the first and second ends 1618a,b. As described in more detail below, selective rotation of the lead screw 1622 and the splines 1624a-c causes various functions of the handle 1614 to transpire, such as translating the end effector 1604 along the longitudinal axis $A_1$ (e.g., z-axis translation) causing the end effector 1604 to articulate (pivot) at the wrist 1606, causing the jaws 1610, 1612 to open and close, and causing the end effector 1604 to fire (operate).

The handle 1614 further includes a carriage 1626 movably mounted along the lead screw 1622 and the splines 1624a-c and housing various activating mechanisms configured to cause operation of specific functions of the end effector 1604. The carriage 1626 may comprise two or more layers, shown in FIG. 16A as a first layer 1628a, a second layer 1628b, a third layer 1628c, a fourth layer 1628d, and a fifth layer 1628e. The lead screw 1622 and the splines 1624a-c each extend through portions of one or more of the layers 1628a-e to allow the carriage 1626 to translate along the longitudinal axis $A_1$ with respect to the lead screw 1622 and the splines 1624a-c. In some embodiments, the layers 1628a-e may be secured to each other in series using one or more mechanical fasteners 1630 (two visible) extending between the first layer 1628a and the fifth layer 1628e and through coaxially aligned holes defined in some or all of the layers 1628a-e. While five layers 1628a-e are depicted, more or less than five may be included in the carriage 1626, without departing from the scope of the disclosure.

The shaft 1602 is coupled to and extends distally from the carriage 1626 through the first end 1618a of the handle 1614. In the illustrated embodiment, for example, the shaft 1602 penetrates the first end 1618a at a central aperture 1632 defined through the first end 1618a. The carriage 1626 is movable between the first and second ends 1618a,b along the longitudinal axis $A_1$ (e.g., z-axis translation) and is thereby able to advance or retract the end effector 1604 relative to the handle 1614, as indicated by the arrows B. More specifically, in some embodiments, the carriage 1626 includes a carriage nut 1634 mounted to the lead screw 1622 and secured between the third and fourth layers 1628c,d. The outer surface of the lead screw 1622 defines outer helical threading and the carriage nut 1634 defines corresponding internal helical threading (not shown) matable with the outer helical threading of the lead screw 1622. As a result, rotation of the lead screw 1622 causes the carriage nut 1634 to advance or retract the carriage 1626 along the longitudinal axis $A_1$ and correspondingly advance or retract the end effector 1604 relative to the handle 1614.

As indicated above, the lead screw 1622 and the splines 1624a-c are rotatably mounted to the first and second ends 1618a,b. More specifically, the first end 1618a of the handle 1614 may include one or more rotatable drive inputs actuatable to independently drive (rotate) the lead screw 1622 and the splines 1624a-c. In the illustrated embodiment, the handle 1614 includes a first drive input 1636a, a second drive input 1636b, a third drive input 1636c (occluded by the shaft 1602, see FIG. 17B), and a fourth drive input 1636d. As described below, each drive input 1636a-d may be matable with a corresponding drive output of an instrument driver such that movement (rotation) of a given drive output correspondingly moves (rotates) the associated drive input 1636a-d and thereby rotates the mated lead screw 1622 or spline 1624a-c. While only four drive inputs 1636a-d are depicted, more or less than four may be included in the handle 1614, depending on the application.

The first drive input 1636a may be operatively coupled to the lead screw 1622 such that rotation of the first drive input 1636a correspondingly rotates the lead screw 1622, which causes the carriage nut 1634 and the carriage 1626 to advance or retract along the longitudinal axis $A_1$, depending on the rotational direction of the lead screw 1622. As used herein the phrase "operatively coupled" refers to a coupled engagement, either directly or indirectly, where movement of one component causes corresponding movement of another component. With respect to the first drive input 1636a being operatively coupled to the lead screw 1622, such operative coupling may be facilitated through intermeshed gears (not shown) arranged within the second end 1618a, but could alternatively be facilitated through other mechanical means, such as cables, pulleys, drive rods, direct couplings, etc., without departing from the scope of the disclosure.

The second drive input 1636b may be operatively coupled to the first spline 1624a such that rotation of the second drive input 1636b correspondingly rotates the first spline 1624a. In some embodiments, the first spline 1624a may be operatively coupled to a first activating mechanism 1638a of the carriage 1626, and the first activating mechanism 1638a may be operable to open and close the jaws 1610, 1612. Accordingly, rotating the second drive input 1636b will correspondingly actuate the first activating mechanism 1638a and thereby open or close the jaws 1610, 1612, depending on the rotational direction of the first spline 1624a.

The third drive input 1636c may be operatively coupled to the second spline 1624b such that rotation of the third drive input 1636c correspondingly rotates the second spline 1624b. In some embodiments, the second spline 1624b may be operatively coupled to a second activating mechanism 1638b of the carriage 1626, and the second activating mechanism 1638b may be operable to articulate the end effector 1604 at the wrist 1606. Accordingly, rotating the third drive input 1636c will correspondingly actuate the second activating mechanism 1638b and thereby cause the wrist 1606 to articulate in at least one degree of freedom, depending on the rotational direction of the second spline 1624b.

The fourth drive input 1636d may be operatively coupled to the third spline 1624c such that rotation of the fourth drive input 1636d correspondingly rotates the third spline 1624c. In some embodiments, the third spline 1624c may be operatively coupled to a third activating mechanism 1638c of the carriage 1626, and the third activating mechanism 1638c may be operable to fire the cutting element (knife) at the end effector 1604. Accordingly, rotating the fourth drive input 1636d will correspondingly actuate the third activating mechanism 1638c and thereby cause the knife to advance or retract, depending on the rotational direction of the third spline 1624c.

In the illustrated embodiment, and as described in more detail below, the activating mechanisms 1838a-c comprise intermeshed gearing assemblies including one or more drive gears driven by rotation of the corresponding spline 1624a-c and configured to drive one or more corresponding driven gears that cause operation of specific functions of the end effector 1604.

In some embodiments, the handle 1614 may include a shroud 1640 sized to receive and otherwise surround the carriage 1626, the lead screw 1622, and the splines 1624a-c. In the illustrated embodiment, the shroud 1640 comprises a tubular or cylindrical structure having a first end 1642a matable with the first end 1618a of the handle 1614, and a second end 1642b matable with the second end 1618b of the handle 1614. The carriage 1626, the lead screw 1622, and the splines 1624a-c can all be accommodated within the interior of the shroud 1640, and the carriage 1626 may engage and traverse (ride on) one or more rails 1644 (shown in phantom) fixed to the shroud 1640. The rails 1644 extend longitudinally and parallel to the lead screw 1622 and are sized to be received within corresponding notches 1646 defined on the outer periphery of the carriage 1626 and, more particularly, on the outer periphery of one or more of the carriage layers 1628a-e. As the carriage 1626 translates along the longitudinal axis A1, the rails 1644 help maintain the angular position of the carriage 1626 and assume any torsional loading that might otherwise adversely affect movement or operation of the carriage 1626.

Figure 16B:
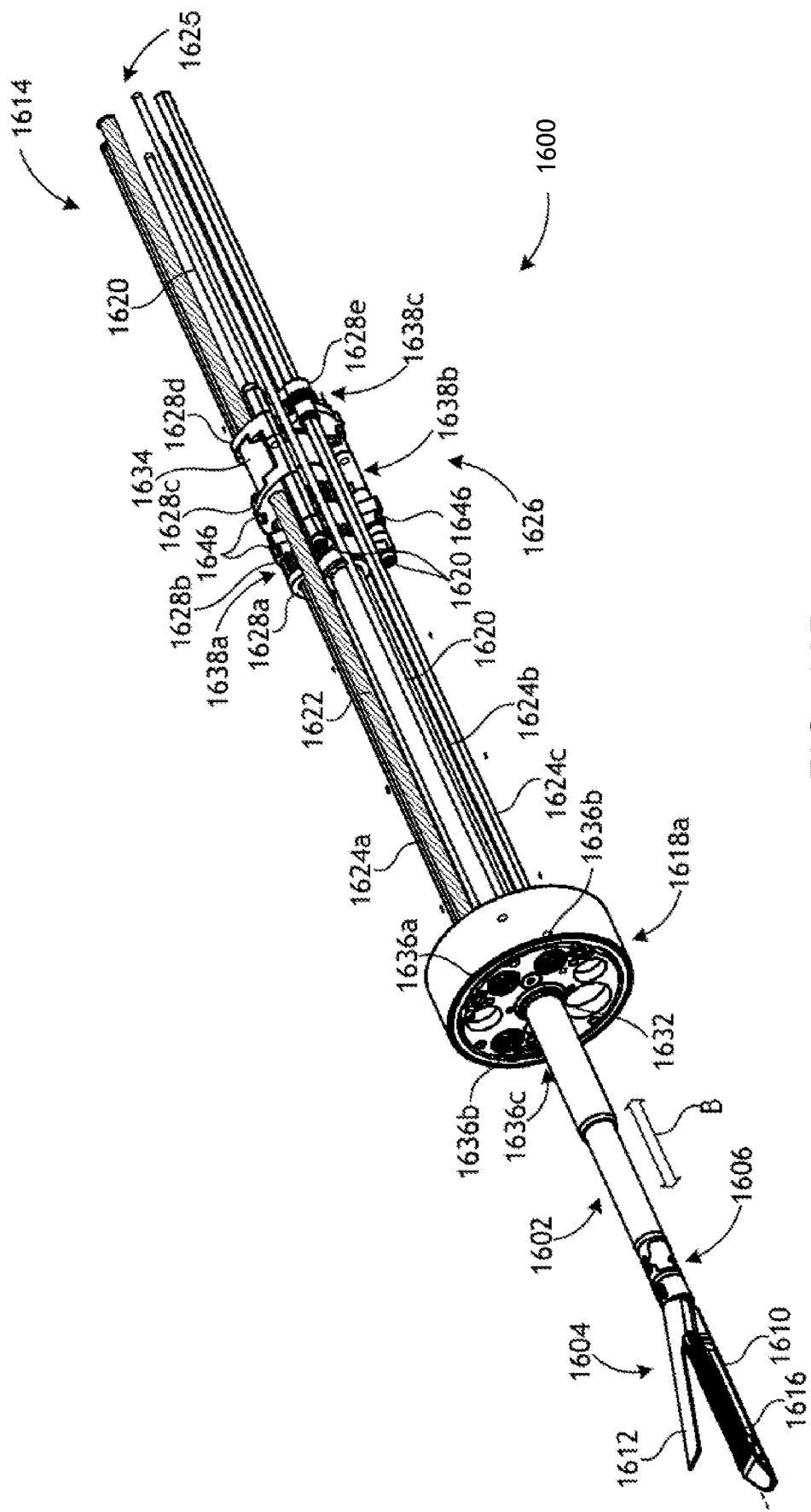
FIG. 16B is an isometric side view of an example surgical tool that may incorporate some or all of the principles of the present disclosure.

FIG. 16B is an isometric view of another exemplary embodiment of the surgical tool 1600, according to one or more additional embodiments. The surgical tool 1600 of FIG. 16B is substantially similar to the surgical tool 1600 of FIG. 16A, except the handle 1614 only has a first or "distal" end 1618a to which the lead screw 1622 and the one or more splines 1624 are rotatably mounted and extend longitudinally therefrom. That is, there is no second end 1618b to which the splines 1624 and lead screw 1622 also rotatably mount. Rather, the splines 1624 and lead screw 1622 are cantilevered into the air having a cantilevered proximal portion 1625.

The carriage 1626 is movably mounted along the lead screw 1622 and the splines 1624a-c and houses the various activating mechanisms configured to cause operation of specific functions of the end effector 1604. The lead screw 1622 and the splines 1624a-c each extend through portions of one or more of the layers 1628a-e to allow the carriage 1626 to translate along the longitudinal axis $A_1$ with respect to the lead screw 1622 and the splines 1624a-c. The carriage 1626 may translate from the distal end 1618a of the handle to the cantilevered proximal portion 1625. Without the added mass of the second end 1618b the distribution of mass of the surgical tool 1600 is optimized more toward the first end 1618a compared to the surgical tool 1600.

Figure 17A:
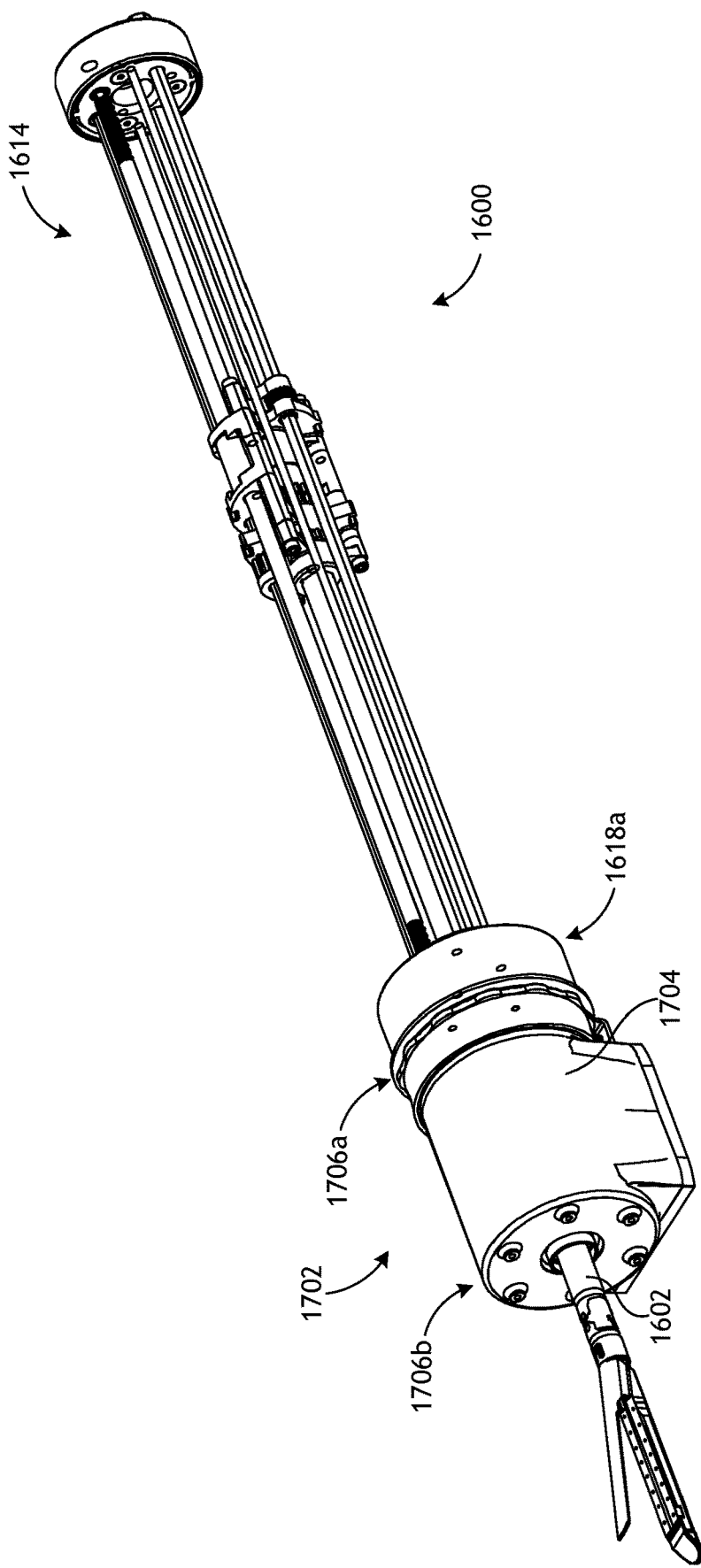
FIG. 17A is an isometric view of the surgical tool of FIG. 16A releasably coupled to an example instrument driver, according to one or more embodiments.

FIG. 17A is an isometric view of the surgical tool 1600 of FIG. 16A releasably coupled to an example instrument driver 1702 according to one or more embodiments. The instrument driver 1702 may be similar in some respects to the instrument drivers 1102, 1200 of FIGS. 11 and 12, respectively, and therefore may be best understood with reference thereto. Similar to the instrument drivers 1102, 1200, for example, the instrument driver 1702 may be mounted to or otherwise positioned at the end of a robotic arm (not shown) and is designed to provide the motive forces required to operate the surgical tool 1600. Unlike the instrument drivers 1102, 1200, however, the shaft 1602 of the surgical tool 1600 extends through and penetrates the instrument driver 1702.

The instrument driver 1702 has a body 1704 having a first or "proximal" end 1706a and a second or "distal" end 1706b opposite the first end 1706a. In the illustrated embodiment, the first end 1706a of the instrument driver 1702 is matable with and releasably coupled to the first end 1618a of the handle 1614, and the shaft 1602 of the surgical tool 1600 extends through the body 1704 and distally from the second end 1706b.

Figure 17B:
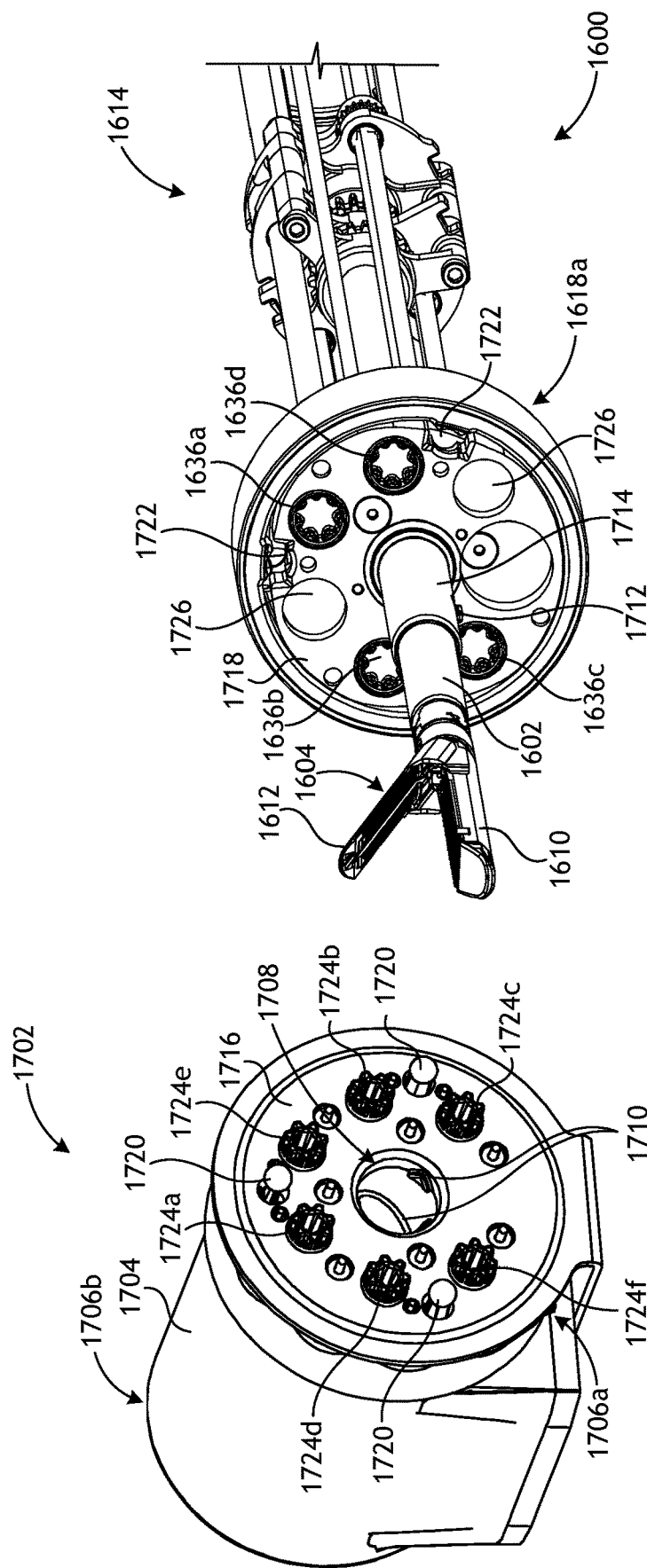
FIG. 17B provides separated isometric end views of the instrument driver of FIG. 17A and the surgical tool of FIG. 16A.

FIG. 17B depicts separated isometric end views of the instrument driver 1702 and the surgical tool 1600 of FIG. 17A. With the jaws 1610, 1612 closed, the shaft 1602 and the end effector 1604 can penetrate the instrument driver 1702 by extending through a central aperture 1708 defined longitudinally through the body 1704 between the first and second ends 1706a,b. To align the surgical tool 1600 with the instrument driver 1702 in a proper angular orientation, one or more alignment guides 1710 may be provided or otherwise defined within the central aperture 1708 and configured to engage one or more corresponding alignment features 1712 provided on the surgical tool 1600. In the illustrated embodiment, the alignment feature 1712 comprises a protrusion or projection defined on or otherwise provided by an alignment nozzle 1714 extending distally from the first end 1618a of the handle 1614. In one or more embodiments, the alignment guide 1710 may comprise a curved or arcuate shoulder or lip configured to receive and guide the alignment feature 1712 as the alignment nozzle 1714 enters the central aperture 1708. As a result, the surgical tool 1600 is oriented to a proper angular alignment with the instrument driver 1702 as the alignment nozzle 1714 is advanced distally through the central aperture 1708. In other embodiments, the alignment nozzle 1714 may be omitted and the alignment feature 1712 may alternatively be provided on the shaft 1602, without departing from the scope of the disclosure.

As illustrated, a drive interface 1716 is provided at the first end 1706a of the instrument driver 1702, and a driven interface 1718 is provided at the first end 1618a of the handle 1614. The drive and driven interfaces 1716, 1718 may be configured to mechanically, magnetically, and/or electrically couple the handle 1614 to the instrument driver 1702. To accomplish this, the drive and driven interfaces 1716, 1718 may provide one or more matable locating features configured to secure the handle 1614 to the instrument driver 1702. In the illustrated embodiment, for example, the drive interface 1716 provides one or more interlocking features 1720 (three shown) configured to locate and mate with one or more complementary-shaped pockets 1722 (two shown, one occluded) provided on the driven interface 1718. In some embodiments, the features 1720 may be configured to align and mate with the pockets 1722 via an interference or snap fit engagement, for example.

The instrument driver 1702 also includes one or more drive outputs that extend through the drive interface 1716 to mate with the drive inputs 1636a-d provided at the first end 1618a of the handle 1614. More specifically, the instrument driver 1702 includes a first drive output 1724a matable with the first drive input 1636a, a second drive output 1724b matable with the second drive input 1636b, a third drive output 1724b matable with the third drive input 1636c, and a fourth drive output 1724d matable with the fourth drive input 1636d. In some embodiments, as illustrated, the drive outputs 1724a-d may define splines or features designed to mate with corresponding splined receptacles of the drive inputs 1636a-d. Once properly mated, the drive inputs 1636a-d will share axes of rotation with the corresponding drive outputs 1724a-d to allow the transfer of rotational torque from the drive outputs 1724a-d to the corresponding drive inputs 1636a-d. In some embodiments, each drive output 1724a-d may be spring loaded and otherwise biased to spring outwards away from the drive interface 1716. Each drive output 1724a-d may be capable of partially or fully retracting into the drive interface 1716.

In some embodiments, the instrument driver 1702 may include additional drive outputs, depicted in FIG. 17B as a fifth drive output 1724e and a sixth drive output 1724f. The fifth and sixth drive outputs 1724e,f may be configured to mate with additional drive inputs (not shown) of the handle 1614 to help undertake one or more additional functions of the surgical tool 1600. In the illustrated embodiment, however, the handle 1614 does not include additional drive inputs matable with the fifth and sixth drive outputs 1724e,f. Instead, the driven interface 1718 defines corresponding recesses 1726 configured to receive the fifth and sixth drive outputs 1724e,f. In other applications, however, fifth and/or sixth drive inputs (not shown) could be included in the handle 1614 to mate with the fifth and sixth drive outputs 1724e,f, or the surgical tool 1600 might be replaced with another surgical tool having fifth and/or sixth drive inputs, which would be driven by the fifth and/or sixth drive outputs 1724e,f.

While not shown, in some embodiments, an instrument sterile adapter (ISA) may be placed at the interface between the instrument driver 1702 and the surgical tool 1600. In such applications, the interlocking features 1720 may operate as alignment features and possible latches for the ISA to be placed, stabilized, and secured. Stability of the ISA may be accomplished by a nose cone feature provided by the ISA and extending into the central aperture 1708 of the instrument driver 1702. Latching can occur either with the interlocking features 1720 or at other locations at the interface. In some cases, the ISA will provide the means to help align and facilitate the latching of the surgical tool 1600 to the ISA and simultaneously to the instrument driver 1702.

Layered Carriage

Figure 18:
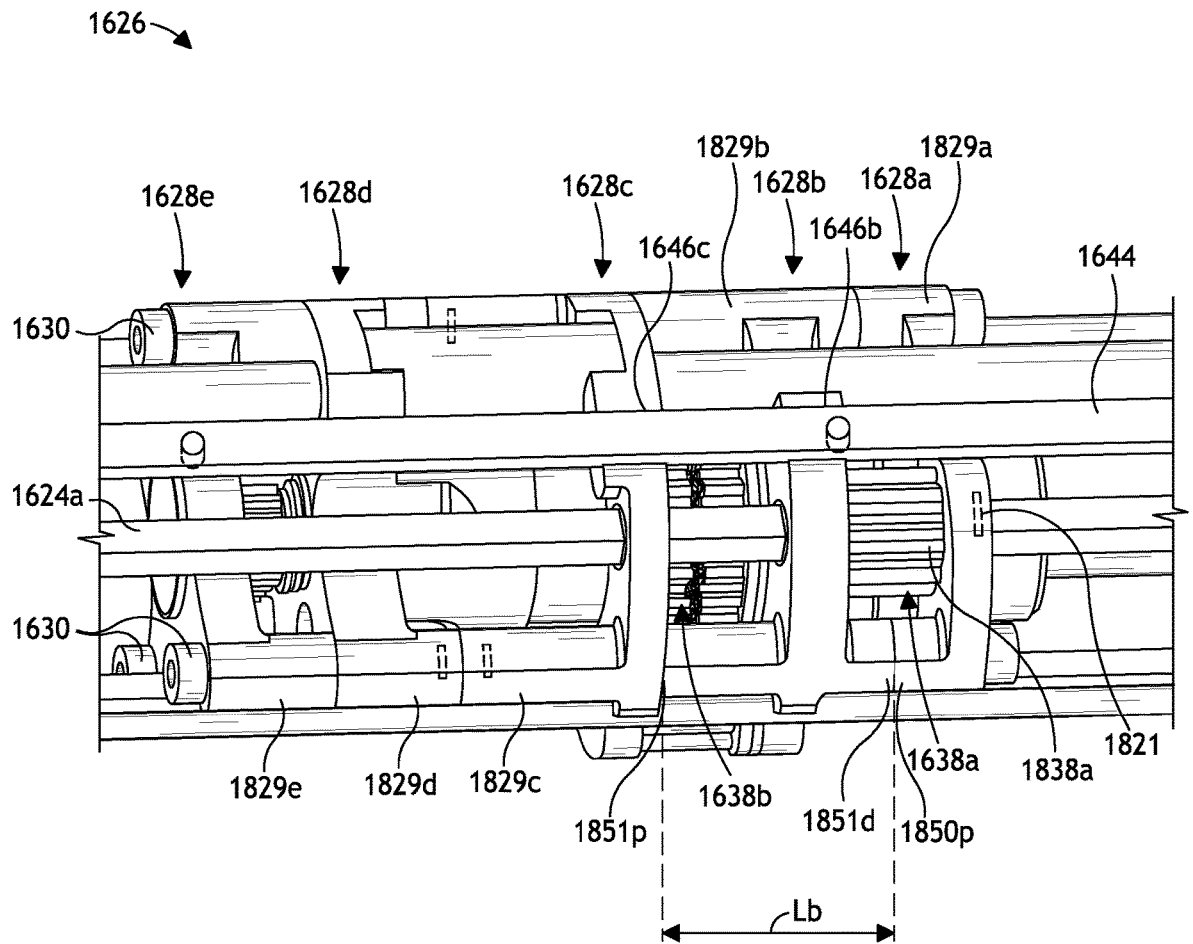
FIG. 18 is an isometric side view of an example carriage that may incorporate some or all of the principles of the present disclosure.

FIG. 18 is an enlarged side view of an exemplary embodiment of the carriage 1626 of FIG. 16A, according to one or more embodiments. In accordance with some aspects of the present disclosure, the carriage 1626 is configured to house various instrument specific functions that are independent of the insertion function (z-axis translation of the carriage 1626). As discussed above, the carriage 1626 may comprise two or more structural layers, operatively coupled to one another in series for cooperative z-axis translation, wherein each layer is associated with at least one function of the surgical tool 1600. In other words, the two or more structural layers operate functions of the end effector 1604 (FIG. 16A) decoupled from and translatable along the insertion axis of the surgical tool 1600.

The carriage 1626 includes structural layers 1628a-e that are stacked together to form the carriage framework. The layers 1628a-e contain or house one or more activating mechanisms that are operatively coupled to corresponding splines that extend through portions of the layers 1628a-e for performing separate functions of an end effector distally located on a tool shaft. The carriage 1626 and the structural layers 1628a-e are able to axially traverse the drive splines during instrument insertion (z-translation) without impacting the end effector functions (e.g., wristed motion, grasping, etc.). While the illustrated embodiment illustrates five structural layers 1628a-e, it is to be understood that the number of layers is non-limiting and that the number of layers can vary, e.g., in relation to the number of functions desired for the associated surgical tool. For example, the number of layers 1628a-e may equal the number of desired tool functions.

Each structural layer 1628a-e includes a layer body 1829a-e, respectively, having a distal surface and a spaced apart proximal surface. As illustrated in the exemplary embodiment of FIG. 18, each layer body 1829a-e includes a substantially planar distal surface and a substantially planar proximal surface. For example, the second structural layer 1628b having second layer body 1829b includes a substantially planar distal surface 1851d and a substantially planar proximal surface 1851p opposite the distal surface 1851d. The second layer body 1829b has a length Lb defined as the distance between the two spaced apart surfaces 1851d, 1851p, and in the direction of the insertion axis of the surgical tool. In some embodiments, the second layer body 1829b houses or otherwise helps secure a corresponding activating mechanism 1638b within the length Lb.

The distal and proximal surfaces of each layer body 1829a-e facilitate a stacking arrangement of the layers 1628a-e. That is, the proximal surface of one layer, e.g., proximal surface 1850p of layer 1628a, is complementary in shape to abut the distal surface 1851d of adjacent layer 1628b. While substantially flat planar surfaces are illustrated in FIG. 18, it is to be appreciated that other complementary surface configurations may be employed, e.g., adjacent convex and concave surfaces. In other words, each structural layer is configured to abut at least one surface of an adjacent layer. For example, the first structural layer 1628a includes a proximal abutment surface 1850p that abuts a distal abutment surface 1851d of the adjacent second structural layer 1628b. While not illustrated, it is contemplated that a spacer or washer may be present between the entire surface and/or portions of the surface of adjacent layers, e.g., between surface 1850p and 1851d, wherein the layers are arranged in series and in substantial alignment along a shaft of the surgical tool.

As briefly mentioned above, the layers 1628a-e can be removably secured to each other in series using one or more mechanical fasteners 1630 (three visible). Since each layer 1628a-e houses or helps contain an activating mechanism, generally corresponding to a specific function of the associated surgical tool, functions of the surgical tool can be disabled by disconnecting the related layer and associated activating mechanism. The disabling feature may be advantageous in bailout situations, wherein the tool or certain functions need to be disabled. For example, if the robotic system is unable to perform a specific function, disconnecting the related layer allows the instrument to be removed from the instrument driver.

In FIG. 18, some or all of the layers 1628a-e include coaxially aligned holes in each layer body 1829a-e that are configured to receive the mechanical fastener 1630. The mechanical fastener 1630 may couple two or more layers together in series, by extending through the coaxially aligned holes in each layer 1628a-e. In this way, individual layers 1628a-e may be disconnected from the carriage assembly 1626 by removing the corresponding fasteners 1630. In other embodiments, the carriage 1626 is configured such that each individual layer 1628a-e is mechanically coupled to adjacent layers via discrete fasteners. In this way, individual layers 1628a-e may be disconnected piecewise. The mechanical fasteners 1630 may include any conventional fastener including, but not limited to, screws, bolts, nuts, or by snap fit connectors and the like.

As briefly mentioned above, the carriage 1626 may define or otherwise provide one or more notches configured to engage the guide rails 1644 of the handle 1614 (FIG. 16A). Each guide rail 1644 may comprise an elongated structure that extends in a substantially longitudinal manner along the axial length of the handle 1614, and may be configured to help maintain an angular position of the carriage 1626. In the illustrated embodiment, the guide rail 1644 is received within notches 1646b,c defined in the second and third layers 1628b,c, respectively. More specifically, the notches 1646b and 1646c are defined in the outer periphery of the bodies 1829b,c of the second and third structural layers 1628b,c, respectively. The notches 1646b,c are complementary in shape to the cross-section of the guide rail 1644 allowing for a sliding relationship between the carriage 1626 and guide rail 1644.

In some embodiments, the carriage 1626 transverses the length of the handle 1614 guided by at least two carriage rails 1644 received within corresponding notches, which provide resistance to torsional loads experienced by the carriage 1626. In some cases, a single layer includes two notches, each configured to engage a separate guide rail. In other cases, at least one layer includes a notch configured to engage a first rail and another connected layer includes a notch configured to engage a second rail, wherein the second rail opposes the first rail. For example, the third layer 1628c includes a notch 1646c capable of engaging the first rail 1644 while another connected layer, e.g., one or more of layers 1628a,b,d,e includes a notch on an opposing side (occluded by carriage 1626) configured to slidably traverse a second rail (not illustrated).

The bodies 1829a-e are configured to secure and support one or more activating mechanisms. The activating mechanisms described herein are powered or otherwise actuated through the rotation of one or more drive outputs, which correspondingly drive one or more mechanical functions of the surgical tool. For example, and without limitation, an activating mechanism can include intermeshed gearing or a cabling system that causes actuation of a surgical tool function. In the exemplary embodiment of FIG. 18, activating mechanisms are embodied as intermeshed gearing that rotate together with a drive spline coupled to a drive output, as generally described above. More specifically, the first spline 1624a may be operatively coupled to the first activating mechanism 1638a such that rotating the first spline 1624a (via rotation of the second drive input 1636b of FIGS. 16 and 17B) will correspondingly actuate the first activating mechanism 1638a and thereby perform a function, such as opening or closing the jaws 1610, 1612 (FIG. 16A) of the end effector 1604 (FIG. 16A), depending on the rotational direction of the first spline 1624a.

As illustrated, the first spline 1624a extends longitudinally through coaxially aligned apertures 1821 (only one visible) defined in the first and second layers 1628a,b of the carriage 1626. A drive gear 1838a may be included with the first spline 1624a and located between adjacent portions of the first and second layers 1628a,b. The first spline 1624a may exhibit a cross-sectional shape matable with a corresponding inner shape passage (described in greater detail below) that extends through the entirety of the body of the drive gear 1838a. Rotation of the first spline 1624a correspondingly drives the drive gear 1838a in rotation. In such embodiments, as the carriage 1626 moves along the longitudinal axis $A_1$ (FIG. 16A), the drive gear 1838a will correspondingly move along the length of the first spline 1624a as captured between the first and second layers 1628a,b. In other embodiments, however, the first spline 1624a may be shaped and otherwise configured to operate as a drive gear. In such embodiments, the drive gear 1838a may be omitted to advantageously reduce the number of component parts.

The first activating mechanism 1638a may include at least one additional gear, e.g., a driven gear (described below as driven gear 2048 of FIG. 20), and the drive gear 1838a may be positioned on the carriage 1626 to engage or otherwise intermesh with the driven gear. Accordingly, as the first spline 1624a is rotated, the drive gear 1838a is able to drive the driven gear in rotation and thereby actuate the first activating mechanism 1638a.

Figure 19A:
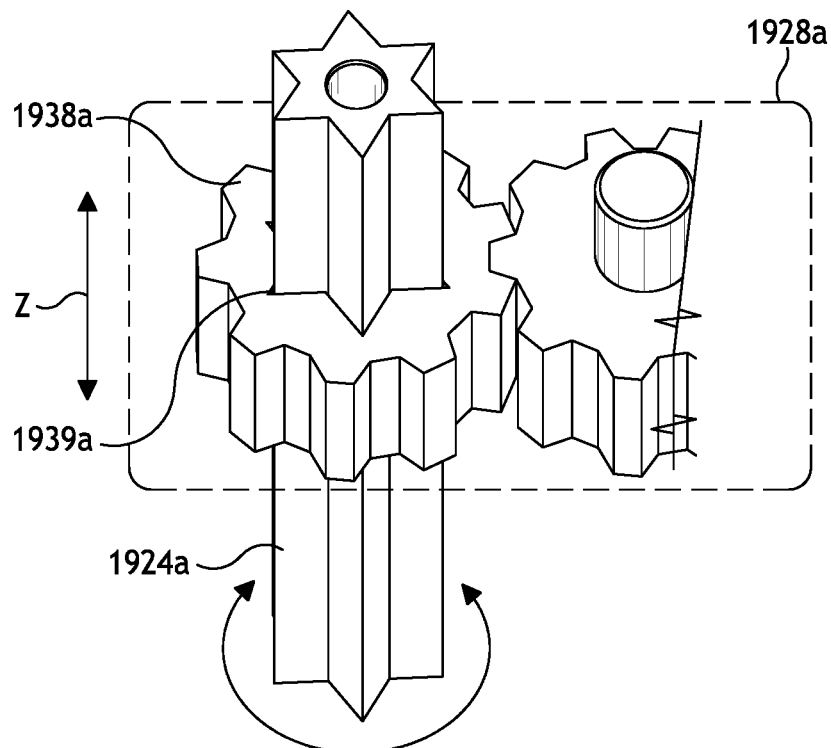
FIG. 19A illustrates an exemplary spline coupled to an activating mechanism that may incorporate some or all of the principles of the present disclosure.

In accordance with another aspect of the present disclosure, splines that operatively couple drive inputs of an instrument handle to an activating mechanism of a carriage may have various shapes and configurations in order to reduce the mass of the tool and minimize friction while possessing sufficient rigidity to efficiently transfer rotation. FIG. 19A, for example, illustrates a mechanical coupling component embodied as a spline drive gear 1938a of a structural layer 1928a rotationally and slidably coupled to a spline 1924a. The spline gear 1938a includes a passage 1939a that extends through the entirety of the gear body. In some embodiments, as illustrated, the passage 1939a has a shape that is complementary in shape to the cross section of the associated spline 1924a. In this way, the spline 1924a is configured to be received within the spline gear 1938a and allows the spline gear 1938a to slide along the length of the spline 1924a in a z-direction while retaining the ability for the spline 1924a to transfer rotational torque to the spline gear 1938a at any position along the length of the spline 1924a. In the illustrated embodiment, the spline 1924a and passage 1939a are star-shaped, i.e., the cross-section of each is a 6-pointed star.

Figure 19B:
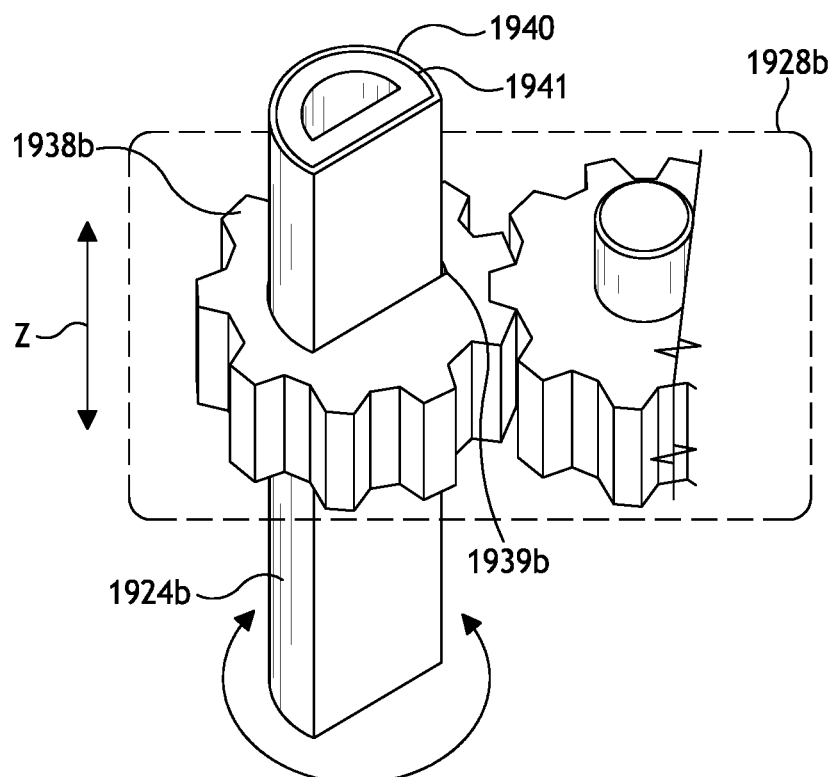
FIG. 19B illustrates another example spline coupled to an activating mechanism that may incorporate some or all of the principles of the present disclosure.

In the exemplary embodiment of FIG. 19B, a spline 1924b is shaped as a half circle, i.e. having a substantially round portion 1940 and a substantially flat edge 1941. The spline gear 1938b is secured to or otherwise included in the structural layer 1928b. Because of the complementary shapes of the spline 1924b and the spline gear 1938b, rotating the spline 1924b will correspondingly drive the spline gear 1938b in rotation.

Figure 19C:
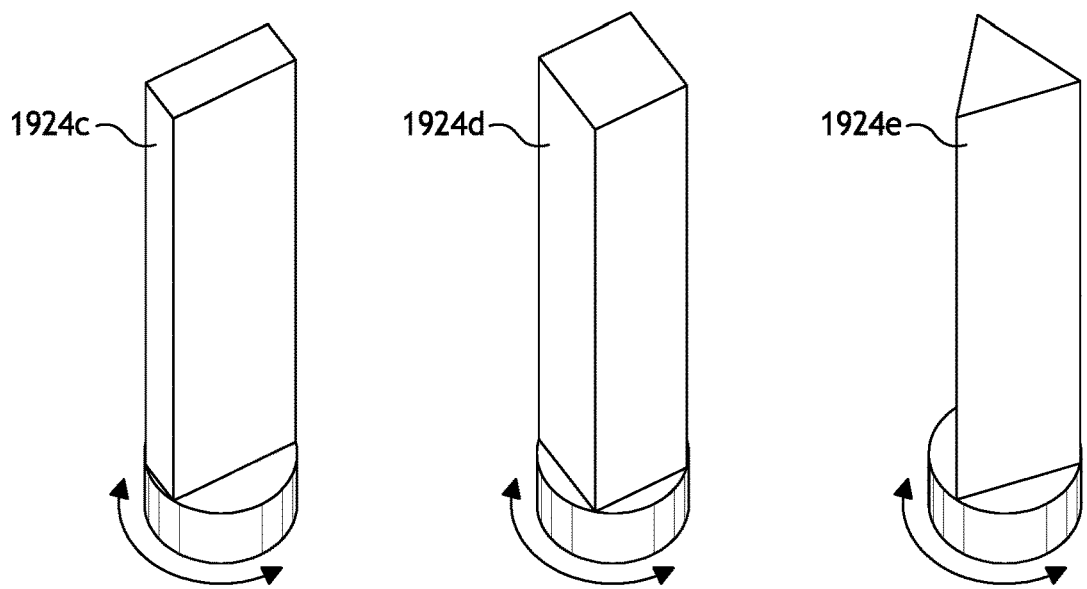
FIG. 19C illustrates an example spline that may incorporate some or all of the principles of the present disclosure.

While spline shapes are illustrated in FIGS. 19A and 19B as star-shaped and half-circle shaped, the shape of the spline and complementary spline gear passage are not limited to the examples shown. For example, the spline and spline gear passage may have other shapes including but not limited to those illustrated in FIG. 19C, e.g., splines with a rectangular cross section 1924c, splines with a square cross-section 1924d and splines with a triangular cross-section 1924e. Furthermore, splines may be solid, as illustrated in FIG. 19C, or may be hollow, as illustrated in FIGS. 19A and 19B, in order to reduce mass. A reduction of spline mass reduces the rotational inertia of the spline and facilitates changes to the rotational velocity of the drive assembly (drive input, drive output, spline, and spline gear).

The shape of the spline and complementary gear passage, e.g., splines 1924a,b, and complementary passages 1939a,b are chosen based on a variety of factors. In some embodiments, it is preferable to reduce the contact surface area between the spline and complementary gear passage to reduce friction between the two components when the carriage, carrying at least one spline gear, is translated along at least one spline. In some embodiments, it is preferable to have a non-circular cross-section that is less likely to strip or slip during the transfer of rotation from the spline to the spline gear.

The splines may be made of any suitable material with sufficient rigidity to transfer torque from a drive input to a spline gear via a spline gear passage, e.g. spline gear 1938a and passage 1939a. Generally, the more stiff or ridged (i.e., geometrically complex) the spline, the more torque the spline can transfer. In some embodiments a spline is composed of a metal material, for example and without limitation, stainless steel. In other embodiments, splines are composed of a plastic material. Splines may be formed from a variety of methods including but not limited to machining, extrusion, injection molding, and 3D printing.

In some embodiments, either the spline or spline passage, e.g. spline 1924a, spline passage 1939a, is coated to reduce friction. For example and without limitation, the surface of the spline may be coated with a friction reducing agent, including but not limited to polymer coatings such as baked on Krytox™, polytetrafluoroethylene (Teflon®), Xylon® and the like.

Figure 20:
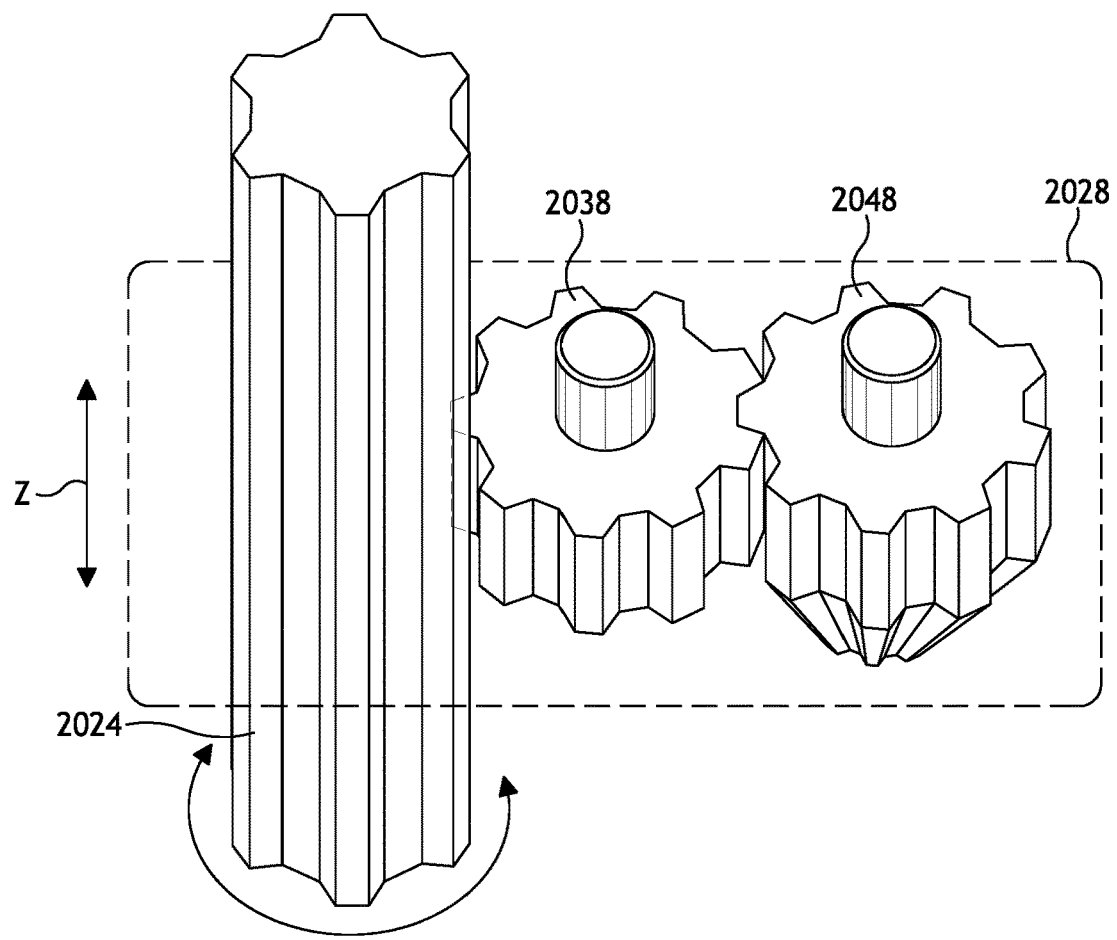
FIG. 20 illustrates an example spline coupled to an activating mechanism that may incorporate some or all of the principles of the present disclosure.

FIG. 20 depicts an example spline coupled to an activating mechanism that may incorporate some or all of the principles of the present disclosure. More specifically, illustrated is a spline 2024, an idler gear 2038, and a driven gear 2048. The idler and driven gears 2038, 2048 may be rotatably secured to or otherwise housed in a structural layer 2028. The idler gear 2038 is operatively coupled to the adjacent spline 2024 and an adjacent driven gear 2048 for transferring rotation from the spline 2024 to the driven gear 2048. More specifically, rather than including a drive gear that slides through a complementary shaped passage of a gear, e.g., passage 1939a,b, of gears 1938a,b, the idler gear 2038 defines elongated teeth that intermesh with corresponding elongated teeth of the adjacent spline 2024. The idler gear 2038 is able to slide along the axial length of the adjacent spline 2024 while retaining the ability to rotate in response to rotation of the spline 2024 at any position along the axial length of the spline 2024. In some cases, the idler gear 2038 may directly couple to the tool shaft. In other cases, rotation of the idler gear 2038 may correspondingly drive the driven gear 2048, and the driven gear 2048 may form part of an activating mechanism configured to drive a mechanical function of the surgical tool 1600 (FIG. 16A)

Structural Exoskeleton

Figures 21A, 21B:
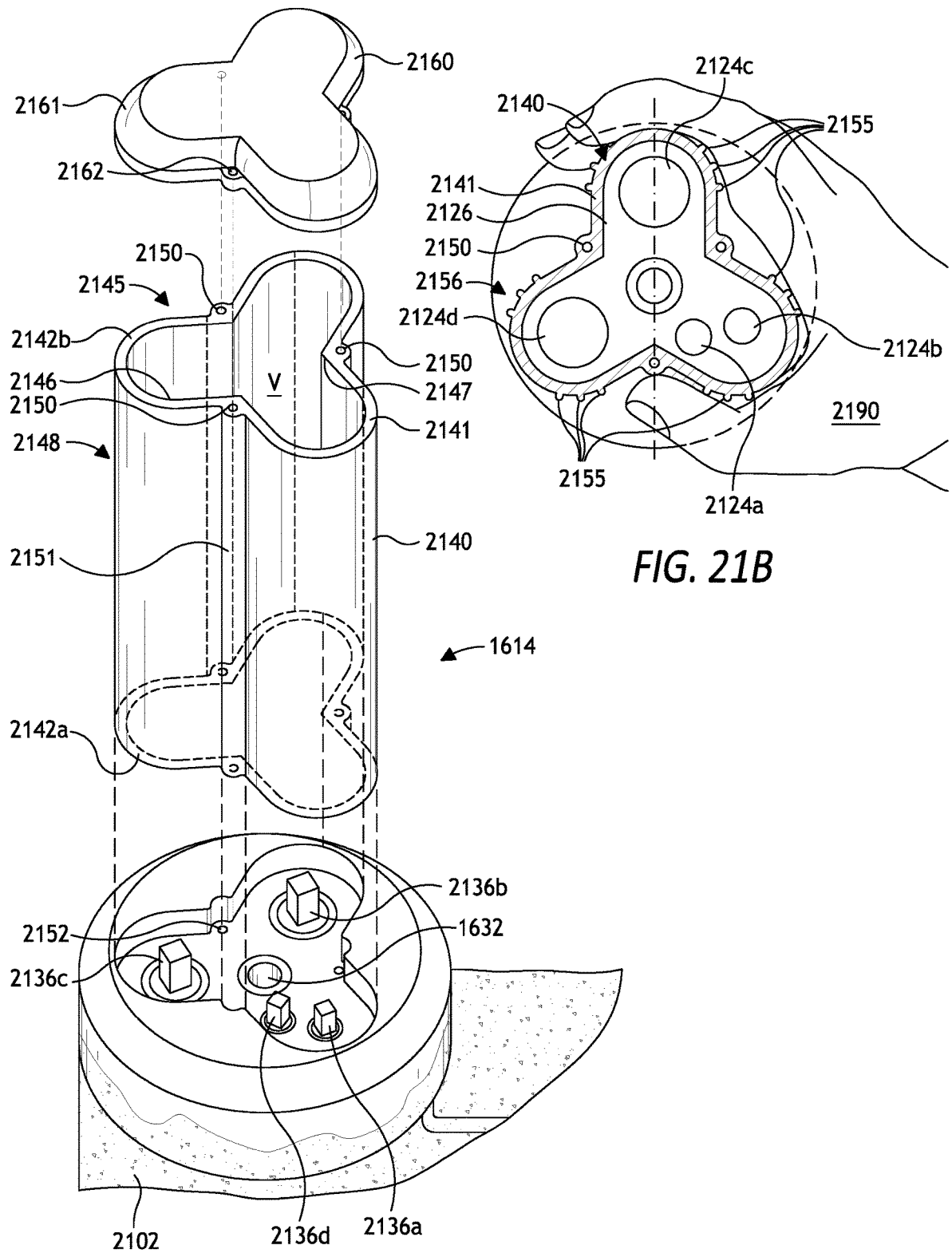
FIG. 21A illustrates an example surgical tool shroud releasably coupled to an example instrument driver, according to one or more embodiments.
FIG. 21B illustrates a top view of the surgical tool shroud of FIG. 21A.

FIGS. 21A and 21B are exploded isometric and end views, respectively of an alternative embodiment of the handle 1614 of FIG. 16A, according to one or more embodiments. As described herein, the shroud 1640 (FIG. 16A) of the handle 1614 may be configured to add structural benefits to the surgical tool 1600 (FIG. 16A), including but not limited to carriage guidance and stability. As illustrated in FIG. 21A, the handle 1614 is operatively coupled to an instrument driver 2102 at the first end 1618a of the handle 1614. The instrument driver 2102 includes one or more drive outputs that extend through the drive interface to mate with drive inputs 2136a-d provided at the first end 1618a of the handle 1614. The drive inputs 2136a-d are each configured to be operatively coupled to a corresponding spline (analogous to the spline 1624a-c of FIG. 16A) that extend along the longitudinal axis of the handle 1614 such that rotation of the drive inputs 2136a-d correspondingly rotate the associated spline. As described above, the central aperture 1632 is configured to receive the shaft 1602 (FIG. 16A) of the surgical tool 1600.

FIG. 21A also illustrates an alternative embodiment of the shroud 1640 of FIG. 16A, referenced in FIG. 21A at 2140.

The shroud 2140 is characterized as a rigid hollow exoskeleton with a continuous exoskeleton wall 2141 sized to receive a carriage 2126 (FIG. 21B) of a compatible (e.g., complementary-shaped) cross-section, as well as a lead screw, and splines coupled to drive inputs 2136a-d. The carriage 2126 may be similar to or the same as the carriage 1626 of FIG. 16A. In the illustrated embodiment, the shroud 2140 (alternately referred to herein as the "exoskeleton 2140") comprises a non-circular tubular structure having a distal end 2142a matable with the first end 1618a of the handle 1614 and a proximal end 2142b opposite the distal end 2142a.

The exoskeleton 2140 has a non-circular cross-section that prohibits rotation of a complementary shaped carriage 2126 received within the exoskeleton 2140. The exoskeleton 2140 may exhibit one or more non-circular features including, but not limited to, indentations 2145, edges 2146, corners 2147, bulges/lobes 2148, chambers, convexity, concavity, juts, projections, protrusions, and any combination thereof. Such non-circular features may prove advantageous in helping guide the similarly-shaped carriage 2126 as the carriage 2126 traverses between the distal end 2142a and the proximal end 2142b. More particularly, the non-circular features function to maintain the angular orientation of the carriage 2126, and assume any torsional loading applied to the carriage 2126 during operation. Additionally, the non-circular geometry of the exoskeleton 2140 prevents the tool from rolling on a flat surface. For example, if the surgical tool is placed on a planar surface, e.g., a table, on its side, the non-circular geometry prohibits the surgical tool from rolling across the planar surface and potentially falling off and damaging the surgical tool or items/persons nearby.

In some embodiments, the non-circular geometry of the exoskeleton 2140 may exhibit symmetry, i.e. may be symmetric in shape, including but not limited to line symmetry. For example, the exoskeleton 2140 exhibits symmetry in relation to the line of symmetry S. That is, the line of symmetry divides the cross-section of the exoskeleton 2140 into two identical halves (bilateral symmetry). While one line of symmetry S is illustrated, it is contemplated that an exoskeleton may have multiple lines of symmetry in relation to its cross-section. In other embodiments, however, the non-circular cross-section may be asymmetric in shape, i.e., exhibiting no symmetry. This can be seen, for example, in the non-circular cross-section of the exoskeleton 2540 of FIG. 25B. In some embodiments, the shape of the non-circular cross-section is designed to minimize the cross-sectional area of the handle 1614, thus potentially saving on manufacturing costs. In some embodiments, the non-circular cross-section includes indentations 2145 and bulges 2148 in relation to the position and size of the splines (discussed in greater detail below) and/or activating mechanisms of the carriage 2126.

As described above, the non-circular cross-section of the exoskeleton 2140 helps prevent the carriage 2126 from twisting or rotating within the exoskeleton 2140 upon assuming torsional loads during operation. That is, the configuration of the exoskeleton 2140 may be similar functionally to the guide rails 1644 discussed above in regard to FIGS. 16 and 18. Rather than including both the exoskeleton 2140 and the guide rails 1644, which provide substantially the same functionality, the complexity of the surgical tool can be reduced by using only the exoskeleton, thus saving costs, weight, and material. Once the carriage 2126 is aligned and inserted into the shaped hollow exoskeleton 2140, the carriage 2126 is rotationally fixed with respect to the exoskeleton 2140 as it advances and retracts between the distal and proximal ends 2142a,b.

As described above, the carriage 2126 may be coupled to a shaft having an end effector. The shaft and end effector may be similar in some respects to the shaft 1602 and end effector 1604 of FIG. 16A and, therefore, may be best understood with reference thereto.

The translation of the carriage 2126 within the exoskeleton 2140 advances and retracts the end effector relative to the handle 1614 and prohibits unwanted rotation of the shaft and end effector by nature of the complementary geometry of the exoskeleton 2140 and the carriage 2126. The carriage 2126 is also movably mounted to at least one spline, also housed within the exoskeleton 2140. In some embodiments, the carriage 2126 may also be movably mounted to a lead screw (e.g., the lead screw 1622 of FIG. 16A). Torsional loads resulting from rotation of the spline and/or the lead screw is transferred to the exoskeleton wall 2141, which provides stability to the end effector during functional operation.

In some embodiments, the exoskeleton 2140 includes at least one fastener bore 2150 extending at least partially between the distal and proximal ends 2142a,b. The fastener bore 2150 is configured to receive a mechanical fastener for securing the exoskeleton 2140 to the first end of the handle 1614. In some embodiments, the fastener bore 2150 is integrated into or otherwise defined by the exoskeleton wall 2141 of the exoskeleton 2140. In other embodiments, and as illustrated in the exemplary embodiment of FIG. 21A, the fastener bore 2150 comprises a through bore defined axially through an alignment feature 2151 of the exoskeleton 2140.

More specifically, the exoskeleton 2140 may include at least one sidewall projection 2151 that projects outwardly from the exoskeleton wall 2141 and extends longitudinally between the distal and proximal ends 2142a,b. In some embodiments, the sidewall projection 2151 may include or otherwise comprise a physical alignment feature for mating the exoskeleton 2140 to the first end 1618a of the handle 1614. That is, the first end 1618a of the handle 1614 includes at least one alignment pocket 2152 complementary in shape to the sidewall projection 2151 such that when the exoskeleton 2140 is mated to the first end 1618a, the alignment feature 2151 nests within the alignment pocket 2152. In this way, the exoskeleton 2140 and housed carriage 2126 can properly align with and couple to the various drive inputs 2136a,b, e.g., coupled via splines extending the length of the handle 1614. In some embodiments, as illustrated, the exoskeleton 2140 may include multiple alignment features 2151, and each alignment feature 2151 may be configured to fit into a corresponding alignment pocket 2152 of the handle 1614.

With continued reference to FIG. 21A, the proximal end 2142b of the exoskeleton 2140 may be configured to receive a cap 2160. The cap 2160 may be similar in shape to the cross-section of the exoskeleton 2140. In some embodiments, the cap 2160 may help provide a sealed interface at the proximal end 2142b and thereby substantially seal the interior volume V of the exoskeleton 2140 from the external environment, which may also prevent dust, debris, and fluid from migrating into the interior and potentially damaging the tool. In some embodiments, a gasket (not illustrated), e.g. a rubber gasket, may be placed between the cap 2160 and the exoskeleton 2140 to enhance the seal quality of the interior volume V. The cap 2160 may also help prevent removal of the carriage 2126 from the exoskeleton 2140. For example, if the tool is turned upside-down, having the cap 2160 secured to the proximal end 2142b will prevent the carriage 2126 from falling out of the hollow exoskeleton 2140.

In some embodiments, the cap 2160 may be coupled to the proximal end 2142b of the exoskeleton 2140 via a snap fit engagement. In other embodiments, or in addition thereto, the cap 2160 may define at least one aperture 2162 located to align with the fastener bore 2150 of the exoskeleton 2140 and configured to receive a mechanical fastener. The mechanical fastener may be used to secure the cap 2160 to the exoskeleton 2140 alone or the mechanical fastener may extend through both the aperture 2162 and the fastener bore 2150 to secure both the cap 2160 and the exoskeleton 2140 to the first end 1618a of the handle 1614.

The cap 2160 may also provide ergonomic features to enhance the handling experience of the surgical tool. For example, in some embodiments, the cap 2160 may define or otherwise provide a rounded peripheral edge 2161. The cap 2160 may include other features, not illustrated, such as a projection or knob for ergonomically accommodating placement of a user's hand.

The exoskeleton 2140 may also include structures and features for facilitating handling and/or enhancing the structural integrity. As depicted in FIG. 21B, for instance, the exoskeleton 2140 may define or otherwise provide a plurality of structural ribs 2155 extending outwardly from the exoskeleton wall 2141. The ribs 2155 may extend at least partially between the distal and proximal ends 2142a,b and/or circumferentially around the non-circular cross-section. In some embodiments, the ribs 2155 add support and rigidity to the exoskeleton 2140. That is, the placement of the ribs 2155 around the perimeter of the exoskeleton wall 2141 allows for the thickness of the exoskeleton wall 2141 to be minimized (saving weight and material) while still maintaining sufficient rigidity to withstand torsional loads applied to the carriage 1614 during translation or activation of a surgical tool function.

In some embodiments, an exterior coating 2156 may be applied to the outer surfaces of the exoskeleton 2140 to enhance the handling properties of the surgical tool. For example, the exoskeleton 2140 may be coated with a material having a high coefficient of friction, which may aid in preventing undesirable slippage when grasped by an operator's hand 2190. Several suitable materials with a high coefficient of friction may be used for the exterior coating such as, for example, a silicone elastomer. It is also contemplated herein to apply other types of coatings to the outer surfaces of the exoskeleton 2140 including, but not limited to, a hydrophobic coating.

In some embodiments, the exoskeleton 2140 may include a coating applied to its interior surfaces to enhance the sliding relationship between the carriage 1614 and the exoskeleton 2140. For example, the exoskeleton 2140 may be internally coated with a material having a low coefficient of friction. A low friction material allows to the carriage 1614 to smoothly slide along the guiding cross-section and thereby prevent binding.

The exoskeleton 2140 may be composed of a suitable material that imparts sufficient rigidity for translating the carriage 2126 subjected to forces of varying direction related to the operation of designed surgical tool functions. In some embodiments, the exoskeleton 2140 is made of a metal material such as, but not limited to, steel (e.g., stainless steel), aluminum, any alloy thereof, or any combination thereof. In other embodiments, the exoskeleton 2140 may be made of a polymeric or plastic material such as, but not limited to, urethane, polycarbonate, acrylonitrile butadiene styrene (ABS), and polyethylene, the polymer or plastic material may include a filled polymer including but not limited to glass or carbon fibers. In yet other embodiments, the exoskeleton 2140 may be made of a composite material, such as fiber glass or carbon fiber.

FIGS. 22A and 22B illustrate alternative embodiments of the handle 1614, of a surgical tool 1600 according to one or more additional embodiments. As illustrated, the handle 1614 includes a layered carriage 2226 similar in some respects to the carriage 1626 of FIGS. 16 and 18, and the carriage 2226 is movably coupled to at least one spline 2222. The carriage 2226 is received or otherwise surrounded by an exoskeleton 2240a (FIG. 22A) or exoskeleton 2240b (FIG. 22B). The exoskeleton 2240a,b may be configured to guide the carriage 2226 as is moves axially along the spline 2222 and assume torsional loading applied on the carriage 2226 during operation. Moreover, the exoskeleton 2240a,b may be configured to help maintain the angular orientation of the carriage 2226 as it translates along the spline 2222.

In FIG. 22A, the cross-section or geometry of the first exoskeleton 2240a is non-circular and complementary in shape to the cross-section or geometry of the carriage 2226, as generally described above with reference to FIGS. 21A-B. In the illustrated embodiment, for example, the geometry of the exoskeleton 2240a includes multiple (four) lobes extending from a centerline of the shroud 2240a, and the carriage 2226 similarly defines or otherwise provides multiple (four) lobes that match or otherwise mate with the lobes of the exoskeleton 2240a. The inner surface of the exoskeleton wall 2241 of the exoskeleton 2240a may be in sliding contact with the carriage 2226 and thereby operate to absorb any torsional loads assumed by the carriage 2226 during operation.

In FIG. 22B, the second exoskeleton 2240b is generally circular in shape and a filler material 2243 may be deposited between the carriage 2226 and the inner wall of the exoskeleton 2240b. In such embodiments, the filler material 2243 may define a bore 2245 configured to accommodate the general cross-sectional shape of the carriage 2226. Consequently, rather than the carriage 2226 being in sliding contact with the interior surface of the exoskeleton wall 2241 of the exoskeleton 2240b, the carriage 2226 may instead engage and slide against the filler material 2243. The filler material 2243 may comprise a variety of rigid or semi-rigid materials. In some embodiments, for instance, the filler material 2243 may comprise, but is not limited to, polymer materials, e./g., polycarbonate, polyurethane, closed or open cell foams, e.g., polyurethane, neoprene, Ethylene propylene diene monomer, chloroprene rubber, styrene-butadiene rubber, or any combination thereof. The filler material 2243 may also have a structure or frame, e.g., honeycomb.

Drive Patterns

Figure 23C:
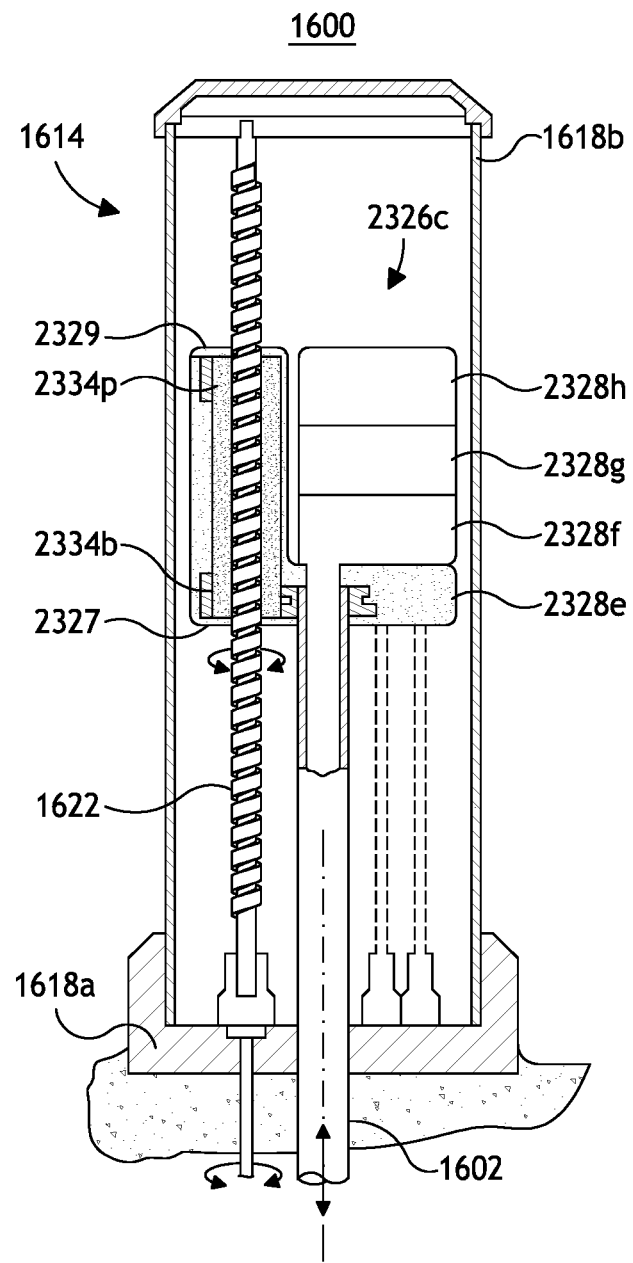
FIG. 23C illustrates a cross-sectional view of another example carriage mounted to a lead screw that may incorporate some or all of the principles of the present disclosure.

FIGS. 23A-23C are partial cross-sectional side views of alternative embodiments of the handle 1614 of FIG. 16A, according to one or more additional embodiments. As described herein, the mounting of a carriage to a lead screw for z-axis translation is configured to reduce the rotation of the carriage and minimize binding of the carriage while simultaneously increasing carriage stability. As illustrated, the handle 1614 includes a carriage 2326 similar in some respects to the carriage 1626 of FIG. 16A. For instance, the carriage 2326 is movable the between first and second ends 1618a,b of the handle 1614 along the longitudinal axis $A_1$ (i.e., z-axis translation), and the shaft 1602 extends distally from the carriage 2326. Accordingly, as the carriage 2326 moves along the longitudinal axis $A_1$, the carriage 2326 is thereby able to advance or retract an end effector (e.g., the end effector 1604 of FIG. 16A) attached to the distal end of the shaft 1602 relative to the handle 1614.

In the illustrated embodiment, the carriage 2326 includes a carriage nut 2334 mounted to a rotatable lead screw 2322, similar to the lead screw 1622 of FIG. 16A. The outer surface of the lead screw 2322 defines helical threading and the carriage nut 2334 defines corresponding internal helical threading (not shown) matable with the outer helical threading of the lead screw 2322. As a result, rotation of the lead screw 2322 causes the carriage nut 2234 to advance or retract the carriage 2326 along the longitudinal axis $A_1$ and correspondingly advance or retract the carriage 2326 and the shaft 2302 relative to the handle 1614.

FIG. 23A illustrates a single carriage nut 2334 located at or near a distal end 2327 of the carriage 2326. During operation of the handle 1614, such as activating various functions of the end effector 1604 (FIG. 16A), the carriage 2326 may experience various torsional and axial forces F that cause the carriage 2326 to rotate or shift in the direction R. Shifting the carriage 2326 in the direction R can bind or inhibit the movement of the carriage 2326 along the handle 1614. According to embodiments of the present disclosure, the carriage 2326 may be stabilized and rotation in the direction R minimized or eliminated by having portions of the carriage nut 2334 located at or near the distal and proximal ends of the carriage 2326. In such embodiments, the carriage 2326 may be mounted to the lead screw 2322 at two or more spaced-apart locations or otherwise spanning a substantial length of the carriage 2326, as described in greater detail below.

In FIG. 23B, the carriage 2326 includes at least two carriage nuts configured to increase the stability of the carriage 2326, i.e., minimize twisting and rotation of the carriage 2326 about the lead screw 2322. More specifically, the carriage 2326 may include a first carriage nut 2334a and a second carriage nut 2334b. The first carriage nut 2334a may be positioned at or near the distal end 2327 of the carriage 2326 and the second carriage nut 2334b is positioned at or near a proximal end 2329 of the carriage 2326. The carriage nuts 2334a, 2334b are each mounted to the rotatable lead screw 2322 and are each supported by the carriage 2326 in a spaced apart relationship generally located on opposite ends of the carriage 2326.

In embodiments where the carriage 2326 is composed of a plurality of layers, a carriage nut may be present on at least two layers for facilitating translation of the carriage in response to rotation of the lead screw 2322. In FIG. 23B, for example, the carriage 2326 includes four stacked layers, depicted as a first layer 2328a, a second layer 2328b, a third layer 2328c, and a fourth layer 2328d. While four layers are illustrated it is to be appreciated that the number of layers of the carriage 2326 may be more or less than four, without departing from the scope of the disclosure. The first layer 2328a may be alternately referred to as the "distal layer 2328a" and the fourth layer 2328d may be alternately referred to as the "proximal layer 2328d". In such embodiments, the first carriage nut 2334a may be coupled to the distal layer 2328a and the second carriage nut 2334b may be coupled to the proximal layer 2328d.

While not shown, it is contemplated herein to include additional carriage nuts coupled to the other layers, e.g., the second and third layers 2328b,c.

In some embodiments, as illustrated, the first carriage nut 2334a may be coupled to or otherwise encompass or span portions of two or more layers of the carriage 2326. In FIG. 23B, for instance, the first carriage nut 2334a is coupled to or otherwise supported by the distal layer 2328a and extends into the adjacent second layer 2328b. Accordingly, in some embodiments, the first carriage nut 2334a may extend across two layers 2328a, 2328b and the second carriage nut 2334b may be secured to a single layer 2328d.

In FIG. 23C, the carriage 2326 includes an elongated carriage nut 2334 that substantially extends from the distal end 2327 to the proximal end 2329 of the carriage 2326. Moreover, the carriage 2326 includes a platform layer 2328e that supports the other layers 2328f-h of the carriage 2326. In the illustrated embodiment, a portion of the platform layer 2328e extends generally between the distal and proximal ends 2327, 2329 of the carriage 2326, but may alternatively extend only a portion of the distance between the distal and proximal ends 2327, 2329, or may extend further than the distance between the distal and proximal ends 2327, 2329, without departing from the scope of the disclosure.

The carriage nut 2334 is mounted to the platform layer 2328e and is thus responsible for the translation of the coupled carriage layers 2328e-h along the lead screw 2322. In some embodiments, the carriage nut 2334 may extend along the entire axial length of the platform layer 2328e, but may alternatively extend along only a portion of the axial length of the platform layer 2328e. Although not illustrated, it is contemplated that a second layer in a stack of two or more layers may incorporate an elongated carriage nut, similar to the elongated nut 2334, having a proximal portion 2334p and a distal portion 2334d and supporting a first layer distally, and a third layer proximally.

Figure 24A:
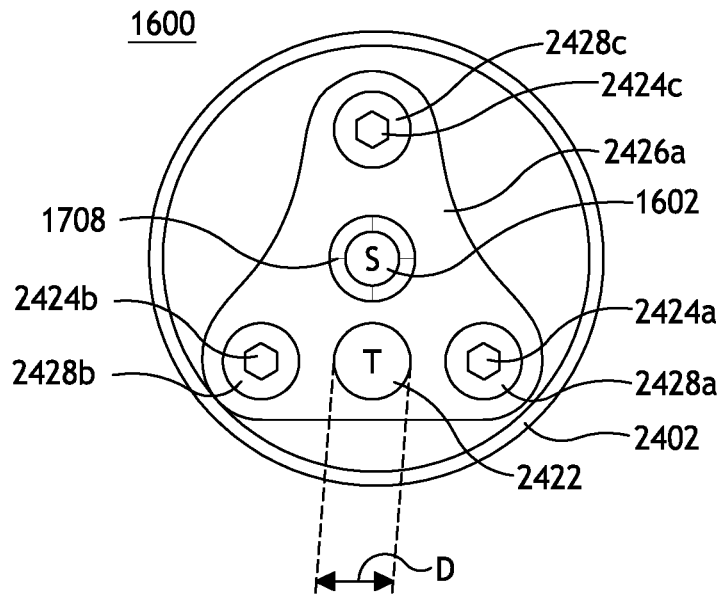
FIG. 24A illustrates a top view of an example carriage operatively coupled to a plurality of splines.
Figure 24B:
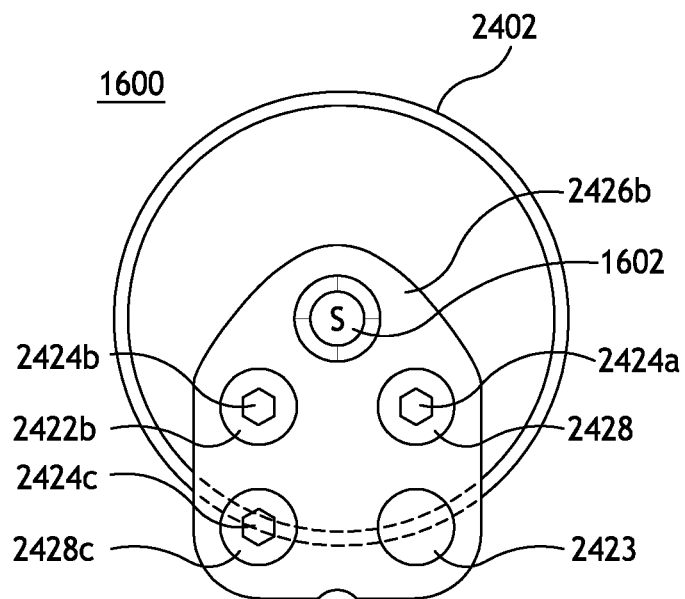
FIG. 24B illustrates a top view of another example carriage operatively coupled to a plurality of splines.

FIGS. 24A and 24B are top views of example embodiments of the surgical tool 1600, according to one or more embodiments of the disclosure. In accordance with another aspect of the present disclosure, the locations of high load splines and activating mechanisms may be optimized with respect to the carriage and exoskeleton to reduce torsional loads and minimize the cross-section of the handle. Certain functions of an associated end effector, triggered by the activating mechanics incorporated within a carriage, require high torsional loads. For example, surgical staplers often experience high torsional loads associated with the firing and closure functions. As described above in regard to FIG. 16A, the carriage rails 1644 located on the shroud 1640 can assume any torsional loading that would otherwise adversely affect the stability of the carriage 1612. However, placing high torsional splines and/or activating mechanisms near a load balancing member of the surgical tool 1600 helps reduce twisting loads and sliding fiction. That is, the centerline of splines are configured so that high torsional loading spline centerlines are as close to a load balancing member, e.g., translational lead screw centerline and/or the shaft axis, reducing the net torsional force on the system by optimizing spline placement.

This configuration may also provide a slimmer geometry to the surgical tool 1600, thus minimizing weight and enhancing ergonomic handling. Torsional loading of the carriage is managed by applying torque to the lead screw, other splines, or struts located adjacent to high-torque inputs. This configuration, as discussed below, can result in a non-circular cross-section of the carriage that balances loading and provides a slimmer geometric look to the surgical device.

As illustrated in FIGS. 24A-24B, carriages 2426a,b, respectively, are received within the surgical tool 1600, and each carriage 2462a,b exhibits a non-circular cross-section. Moreover, each carriage 2462a,b is movably mounted to a plurality of splines 2424a-c driven by the outputs of an instrument driver 2402. The carriages 2426a,b and the splines 2424a-c may be similar in some respects to the carriage 1626 and the splines 1624a-c of FIG. 16A, and the instrument driver 2402 may be similar in some respects to the instrument drivers 1102, 1200, 1702 of FIGS. 11, 12, and 17 respectively, and therefore may be best understood with reference thereto. The shaft 1602 is coupled to and extends distally from the carriage 2426a,b through the first end of the handle. In the illustrated embodiment, the shaft 1602 penetrates an aperture 1708 of the instrument driver 2402. The carriage 2426a includes a plurality of activating mechanisms 2428a-c, each supported by the carriage 2426a,b and each associated with a separate function of the end effector. The splines 2424a-c are each rotationally mounted to the first end of the handle and extend between the handle ends. Each spline 2424a-c is operatively coupled to one of the activating mechanisms 2428a-c, respectively, to drive the associated function of the end effector.

In FIG. 24A, the splines 2424a-c are arranged such that splines having the highest operating torsional load are located adjacent to a load balancing member 2422. The load balancing member 2422 comprises an elongated structure extending between the first end and second ends of the handle and has a diameter D. The load balancing member 2422 has sufficient stiffness to minimize twisting of the carriage 2426a during the operation of high load functions, such as closure and firing of the end effector. The load balancing member 2422 may be rod shaped and may exhibit any cross-sectional configuration. In some embodiments, the load balancing member 2422 comprises a strut, similar to the strut 1620 of FIG. 16A. The arrangement of splines 2424a-c in relation to a load balancing member 2422 based on their torque lends to design of the carriage 2426a to have a non-circular cross-section.

The end effector 1604 (FIG. 16A) arranged at the distal end of the shaft 1602 is capable of articulation, firing, and clamping, as generally described above. The first activating mechanism 2428a is driven by the first spline 2424a to perform a high torsional clamping function of the end effector 1604. The second activating mechanism 2428b is driven by the second spline 2424b to perform a high torsional firing function of the end effector 1604. The third activating mechanism 2428c is driven by the third spline 2424c to articulate the end effector 1604, wherein the articulation function does not require the torque values associated with either the clamping or firing functions, e.g., the torque of the articulation function is less than the torque required for clamping and/or firing. Each spline 2428a, 2428b associated with high torsional operations (via activating mechanisms 2428a,b, respectively) are placed adjacent to the load balancing member 2422 to minimize twisting of the carriage 2426a during operation.

In some embodiments, the load balancing member 2422 comprises a lead screw, similar in some respects to the lead screws 1622, 2222, and 2322, of FIGS. 16, 22A-22B, and 23A-23B, respectively. Accordingly, the load balancing member 2422 may alternatively be referred to herein as the "lead screw 2422," which facilitates translation of the carriage 2426a along the longitudinal axis of the handle ("the insertion axis") e.g., between the first and second ends. In the illustrated embodiment, the shaft 1602 occupies or is otherwise located at the central axis of the instrument driver 2402 as well as the center of the carriage 2426a. Here, the lead screw 2422 is positioned off-center in relation to the carriage 2426a and the instrument driver 2402. The lead screw 2422 is generally configured to have sufficient rigidity to provide the translation function of the carriage 2426a, wherein the rigidity characteristic may also be leveraged to resist twisting of the carriage 2426a during firing and/or clamping functions of the end effector 1604 (FIG. 16A). That is, due to a potentially larger cross-sectional size and/or stiffer material (e.g., the lead screw 2422 may be composed of a strong metal like stainless steel), placing the high torsional loading splines 2428a,b as close as possible to the load balancing lead screw 2422 aids in balancing the torsional loading on the carriage 2426a, and thus minimizing undesirable rotations of the carriage 2426a.

In FIG. 24B, a load balancing member may be embodied as an adjacent spline. That is, a first spline 2424a configured to perform a high torsional clamping function of the end effector 1604 (FIG. 16A) may be located adjacent to a load balancing member characterized and referred to herein as the second spline 2422b, which is configured to perform a high torsional firing function of the end effector 1604. In these embodiments, the first spline 2424a may be configured to rotate in a first direction (e.g., clockwise) and the load balancing member 2424b may be configured to rotate in a second direction (e.g., counter-clockwise) opposite the first direction. That is, the splines 2424a,b are configured such that when one or more or working simultaneously, the torsional load applied by one spline is equal and opposite to the torsional load applied by another spline. The load balancing member 2422b in FIG. 24B may have a diameter greater than the diameter of the first spline 2424a having a high operating torsional load. In other embodiments, the load balancing member 2422b has a stiffness that is greater than the stiffness of the spline having the highest operating torsional load.

Figure 25A:
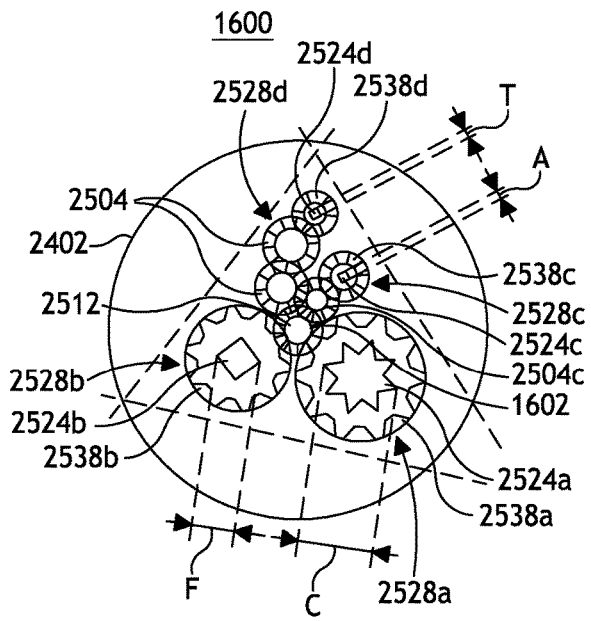
FIG. 25A illustrates a top view of a plurality of activating mechanisms coupled to a plurality of splines.
Figure 25B:
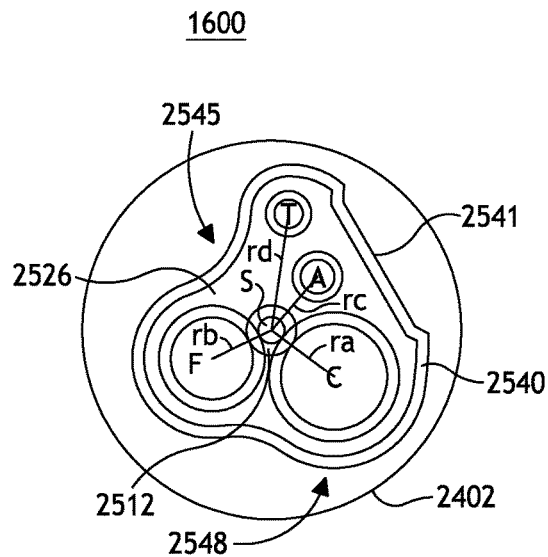
FIG. 25B illustrates a top view of an example carriage operatively coupled to the activating mechanisms and splines of FIG. 25A.

FIGS. 25A and 25B illustrate top cross-sectional views of another example embodiment of the surgical tool 1600, according to one or more additional embodiments. In accordance with another aspect of the present disclosure, the sizes as well as the locations of each spline coupled to the carriage may be optimized to reduce torsional loads experienced by the carriage and minimize the cross-sectional area of the carriage/handle. Rather than having splines of substantially the same diameter, the diameter of a spline may correspond to the torque value required by the associated function of that spline (coupled to an activating mechanism of the carriage). The more torque required to perform a function, the larger the diameter of the spline (imparting increased durability/stiffness), and the less torque required to perform a function, the smaller the diameter of the spline. The multiple sizing of the splines allows for creative compact designs of the carriage and activating mechanisms as well as providing a non-circular cross-section of the tool handle (e.g., carriage and shroud/exoskeleton).

As illustrated, the surgical tool 1600 may include activating mechanisms 2528a-d and a carriage 2526 substantially similar to the activating mechanisms 1638a-c and the carriage 1626, respectively, of FIG. 16A. Each activating mechanism 2528a-d is coupled to a separate spline 2524a-d, respectively, which are driven by the outputs of an instrument driver 2402. The splines 2524a-d, are each rotationally mounted to an end of the handle (e.g., the handle 1614 of FIG. 16A) and extend between the handle ends allowing the carriage 2526 that supports the drive mechanisms 2528a-d to traverse the length of the handle while activation of the associated end effector functions are decoupled from the z-axis translation.

Each activating mechanism 2428a-d and the one or more idle gears 2504 are supported by the carriage 2526 and associated with a separate function of the end effector. In the exemplary embodiment of FIGS. 25A-25B the surgical tool 1600 is a surgical stapler and the first spline 2524a drives the first activating mechanism 2528*a* to perform a high torsional clamping function of the associated end effector. The first spline 2524*a* has a first cross-sectional area and a diameter C. The first activating mechanism 2528*a* includes a drive gear 2538*a* that is directly or indirectly coupled to the shaft 1602. The second activating mechanism 2528*b* is driven by the second spline 2524*b* to perform a high torsional firing function of the end effector. The second spline 2524*b* has a second cross-sectional area and a diameter F. The second activating mechanism 2528*b* includes a drive gear 2538*b* coupled to the second spline 2524*b* for transmitting torque to the second activating mechanism. The third activating mechanism 2528*c* is driven by the third spline 2524*c* to articulate the end effector, wherein the articulation function does not require the torque values associated with first and second splines 2528*a,b*, e.g., the torque of the articulation function is less than the torque required for clamping and/or firing. The third spline 2524*c* has a third cross-sectional area and a diameter A. The third activating mechanism 2528*c* includes a drive gear 2538*c* coupled to the third spline 2524*c* for transmitting torque to the third activating mechanism. The fourth activating mechanism 2528*d* is driven by the fourth spline 2524*d* to axially translate the carriage 2526. The fourth spline 2528*d* has a fourth cross-sectional area and a diameter T. The fourth activating mechanism 2528*d* includes a drive gear 2538*d* that is coupled to the shaft 1602 via at least one idler gear 2504.

In some embodiments, the splines 2528*a-d* exhibit at least two different cross-sectional areas and/or diameters, e.g. diameters C, F, A, T. That is, the surgical tool 1600 includes at least one spline associated with a high torque function, e.g., clamping, having a large "high torsion" cross-section (e.g., corresponding to diameters C or F). The surgical tool 1600 also includes at least one spline associated with a low torque function, e.g. articulation, having a low torsion cross-section (e.g., corresponding to diameters A or T). In these embodiments, the high torsion cross-section of a spline associated with a high torque function is larger in area than the area of the low torsion cross-section spline associated with a low torque function. In this way, the higher torque functions are driven by stiffer splines with larger cross-sections and/or diameters while the other functions are driven by splines with a smaller cross-section and/or smaller diameter. Sizing the splines 2528*a-d* based on input torque requirements allows for a reduction in rotating mass of smaller load splines as well as the overall weight and cross-section of the surgical tool 1600.

In some embodiments, the cross-section of the tool handle with optimized spline size may be symmetric, i.e., similar to the non-circular cross-sectional shapes of the exoskeleton 2140 and 2240*a,b* of FIGS. 21A-22B, respectively. In other embodiments, and as illustrated in the exemplary embodiment of FIGS. 25A-25B, the non-circular cross-section of the exoskeleton 2540 with optimized spline size may be asymmetric in shape.

In some embodiments, each spline 2524*a-d* has a different cross-sectional area that is related to the input torque requirements of the associated end effector function. For example, the input torque Tc required for clamping is greater than the input torque Tf required for firing, which is greater than the input torque Tt required for translation, which is greater than the input torque Ta required for articulation of the end effector. Thus, Tc>Tf>Tt>Ta. Likewise, the cross-sectional area/diameter C of the first spline 2524*a* associated with clamping is greater than the cross-sectional area/diameter F of the second spline 2524*b* associated with firing, which is greater than the cross-sectional area/diameter T of the third spline 2524*c* associated with translation, which is greater than the cross-sectional area/diameter A of the fourth spline 2524*d* associated with articulation. Thus, in terms of diameter, C>F>T>A.

In some embodiments, and as illustrated in FIGS. 25A-25B, the plurality of splines 2524*a-d* and/or associated activating mechanisms 2524*a-b* are located in a planetary relationship with respect to the shaft 1602. In other words, the center of each spline 2524*a-d* is located at a distance (radius) ra-rd from the shaft 1602. In some embodiments, the distance from the shaft to the center of each spline is generally the same for each, such as is depicted in the exemplary embodiment of FIG. 22A. In other embodiments, and as illustrated in FIG. 25B, at least two radii extending from the shaft to the center of a spline, e.g., ra, rb, are different. In some further embodiments, at least at least three radii, extending from the shaft to the center of a spline, e.g., ra, rb rc, are different. In other words, the center of each spline 2524*a-d* is configured to be at least the radius of the spline plus the radius of the shaft 1602. In yet further embodiments, the distance from the shaft 1602 to the center of each spline is different. In each of these embodiments, the carriage 2526 can exhibit a cross-sectional shape that corresponds to the general shape of the spline arrangement.

In some embodiments, the splines 2524*a-d* may be arranged such that an outer cross-sectional contour 2541 of the exoskeleton 2540 corresponds with the placement and size of the interior splines 2524*a-d* and/or activating mechanisms 2528*a-d*. That is, the exoskeleton 2540 is organically shaped to the interior components (i.e., the carriage 2425, the splines 2524*a-d*, and/or the activating mechanisms 2528*a-d*) to reduce mass, provide carriage guidance, increase handle rigidity, minimize system twisting, and/or provide an ergonomic form factor for the surgical tool 1600. While the planetary arrangement is expressly discussed in regard to FIGS. 25A-25B, it is to be appreciated that other embodiments also illustrate the planetary arrangement including, but not limited to, those embodiments illustrated in FIGS. 21B, 22A-22B, and 24A-24B.

Figure 25C:
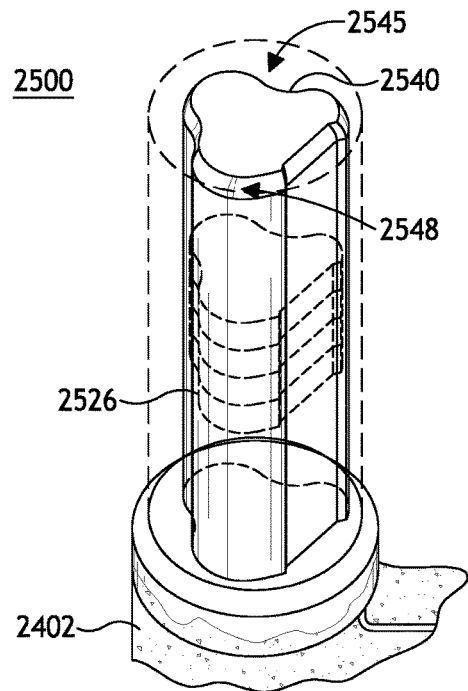
FIG. 25C illustrates an isometric view of a surgical tool handle and shroud configured to house the carriage of FIG. 25B.

FIG. 25C illustrates a transparent isometric view of the carriage 2526 of FIG. 25B spline within an organically shaped exoskeleton. As noted above, the sizing and arrangement of the splines 2524*a-d* and associated activating mechanisms 2528*a-d*, allows the external contour 2541 of the exoskeleton 2540 to conform to the interior position and sizing of the housed components. That is, the non-circular features of the exoskeleton 2540 correspond to and accommodate the position and sizing of the splines and activating mechanisms. For example, bulge/lobe 2548 relates to the size and position of the first spline 2524*a* (FIG. 25A) and the first activating mechanism 2528*a* (FIG. 25A). Furthermore, indentation 2545 corresponds to a portion of the surgical tool 1600 where internal components have been optimized to reduce the cross-sectional footprint of the handle. These non-circular features also function to maintain the angular position of the carriage 2526, assuming any torsional loading that would otherwise adversely affect the carriage.

4. Implementing Systems and Terminology.

Implementations disclosed herein provide systems, methods and apparatus for instruments for use with robotic systems. It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the terms "generally" and "substantially" are intended to encompass structural or numeral modification which do not significantly affect the purpose of the element or number modified by such term.

The headings used herein are intended as a matter of convenience for readers of this application and any resulting patent and are not intended to limit the scope of the disclosure.

To aid the Patent Office and any readers of this application and any resulting patent in interpreting the claims appended herein, applicants do not intend any of the appended claims or claim elements to invoke 35 U.S.C. 112(f) unless the words "means for" or "step for" are explicitly used in the particular claim.

The foregoing previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A surgical tool for a robotic instrument driver, comprising:
    a handle having a first end;
    at least one spline rotatably coupled to the handle and extending proximally from the first end along a longitudinal axis of the handle;
    a carriage movably mounted to the at least one spline and including a first layer and a second layer removably secured to each other in series along the longitudinal axis such that a proximal surface of the first layer engages and mates with a distal surface of the second layer, wherein the at least one spline extends through a portion of at least one of the first and second layers and the carriage translates along the at least one spline;
    an elongate shaft secured to and extending from one of the first or second layers and penetrating the first end, the shaft having an end effector arranged at a distal end thereof; and
    an activating mechanism coupled to one or both of the first and second layers and actuatable to operate a function of the end effector.

2. The surgical tool according to claim 1, further comprising:
    a drive input arranged at the first end and operatively coupled to the at least one spline such that rotation of the drive input correspondingly rotates the at least one spline; and
    an instrument driver arranged at an end of a robotic arm and releasably matable with the handle at the first end, the instrument driver providing a drive output matable with the drive input such that rotation of the drive output correspondingly rotates the drive input and thereby actuates the activating mechanism.

3. The surgical tool according to claim 1, wherein the at least one spline forms part of a plurality of splines, and wherein each spline is rotationally attached to the first end of the handle and configured to mechanically communicate with a drive output of a robotic instrument driver, each spline being coupled to a separate activating mechanism, and wherein rotation of the spline drives an associated function of the end effector.

4. The surgical tool according to claim 1, wherein the activating mechanism includes a drive gear coupled to or forming part of the at least one spline, and wherein rotation of the at least one spline correspondingly rotates the drive gear.

5. The surgical tool according to claim 4, wherein the drive gear defines a passage complementary in shape to a cross-section of the at least one spline, and wherein the at least one spline extends through the passage.

6. The surgical tool according to claim 1, wherein the activating mechanism includes a drive gear arranged adjacent to and in sliding contact with the at least one spline, and wherein rotation of the associated spline rotates the gear of the activating mechanism.

7. The surgical tool according to claim 6, wherein the drive gear defines gear teeth that intermesh with gear teeth defined by the at least one spline.

8. The surgical tool according to claim 1 wherein the carriage comprises three or more layers.

9. The surgical tool according to claim 1, further comprising:
    a guide rail extending proximally from the first end; and
    one or more notches defined in the carriage and sized to receive the guide rail, wherein the guide rail slides within the one or more notches as the carriage moves along the at least one spline.

10. The surgical tool according to claim 9, wherein the guide rail assumes torsional loading of the carriage and thereby minimizes rotation of the carriage with respect to the handle.

11. The surgical tool according to claim 9, wherein the one or more notches are defined on an outer periphery of one or both of the first and second layers.

12. The surgical tool according to claim 9, wherein the one or more notches comprises a first notch and a second notch, and wherein the first notch and the second notch are located on circumferentially opposite sides of the carriage.

13. The surgical tool according to claim 1, further comprising a lead screw extending from the first end, wherein the carriage is movably mounted to the lead screw at a carriage nut secured to the carriage, and wherein rotation of the lead screw moves the carriage and the carriage nut axially toward and away from the first end and thereby moves the end effector distally or proximally.

14. The surgical tool according to claim 1, wherein the first and second layers are removably secured to each other using one or more mechanical fasteners.

15. The surgical tool according to claim 14, wherein the first and second layers each include coaxially aligned holes that receive the one or more mechanical fasteners.

16. The surgical tool according to claim 1, wherein the function of the end effector is selected from the group consisting of articulation of the end effector, clamping of jaws of the end effector, displacing a cutting element of the end effector, displacing the end effector, and any combination thereof.

17. The surgical tool according to claim 1, further comprising a second end opposite the first end of the handle, wherein the at least one spline extends between the first and second ends and wherein the carriage is configured to translate between the first and second ends.

18. A method, comprising:
 locating a robotic surgical tool adjacent a patient, the robotic surgical tool comprising:
  a handle having a first end;
  at least one spline rotatably coupled to the handle and extending proximally from the first end along a longitudinal axis of the handle;
  a carriage movably mounted to the at least one spline and including a first layer and a second layer removably secured to each other in series along the longitudinal axis such that a proximal surface of the first layer engages and mates with a distal surface of the second layer, wherein the at least one spline extends through a portion of at least one of the first and second layers;
  an elongate shaft secured to and extending from one of the first or second layers the carriage and penetrating the first end, the shaft having an end effector arranged at a distal end thereof; and
  an activating mechanism coupled to one or both of the first and second layers;
 rotating the at least one spline by actuating a drive input arranged at the first end and operatively coupled to the at least one spline; and
 actuating the activating mechanism as the at least one spline rotates and thereby operating a function of the end effector.

19. The method of claim 18, further comprising removably securing the first and second layers to each other using one or more mechanical fasteners.

20. The method of claim 18, further comprising advancing the carriage distally and proximally along the at least one spline.

21. The method of claim 18, further comprising guiding the carriage toward and away from the first end with at least a guide rail extending from the first end.

* * * * *